United States Patent
Meegalla et al.

(10) Patent No.: US 9,688,642 B2
(45) Date of Patent: Jun. 27, 2017

(54) SUBSTITUTED PYRAZINES AS GPR40 AGONISTS

(71) Applicant: Janssen Pharmaceutica NV, Beerse (BE)

(72) Inventors: Sanath Meegalla, Garnet Valley, PA (US); Hui Huang, Blue Bell, PA (US); Mark R. Player, Phoenixville, PA (US)

(73) Assignee: Janssen Pharmaceutica NV, Beerse (BE)

( * ) Notice: Subject to any disclaimer, the term of this patent is extended or adjusted under 35 U.S.C. 154(b) by 48 days.

(21) Appl. No.: 14/794,907

(22) Filed: Jul. 9, 2015

(65) Prior Publication Data
US 2016/0009662 A1    Jan. 14, 2016

Related U.S. Application Data

(60) Provisional application No. 62/022,257, filed on Jul. 9, 2014.

(51) Int. Cl.
| | |
|---|---|
| *A61K 31/4965* | (2006.01) |
| *C07D 241/10* | (2006.01) |
| *C07D 241/12* | (2006.01) |
| *C07D 241/18* | (2006.01) |
| *C07D 241/20* | (2006.01) |
| *C07D 401/04* | (2006.01) |
| *C07D 403/04* | (2006.01) |
| *C07D 405/12* | (2006.01) |
| *C07D 409/04* | (2006.01) |
| *C07D 409/14* | (2006.01) |
| *C07D 413/04* | (2006.01) |

(52) U.S. Cl.
CPC ......... *C07D 241/12* (2013.01); *C07D 241/18* (2013.01); *C07D 241/20* (2013.01); *C07D 401/04* (2013.01); *C07D 403/04* (2013.01); *C07D 405/12* (2013.01); *C07D 409/04* (2013.01); *C07D 409/14* (2013.01); *C07D 413/04* (2013.01)

(58) Field of Classification Search
CPC .................. A61K 31/4965; C07D 241/10
USPC ........................ 514/252.1; 544/336
See application file for complete search history.

(56) References Cited

U.S. PATENT DOCUMENTS 6,958,353 B2 * 10/2005 Konno ................. C07D 231/12
                                                                     514/255.05

FOREIGN PATENT DOCUMENTS

| WO | WO 2014/078608 A1 | 5/2014 |
| WO | WO 2014/082918 A1 | 6/2014 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report of the International Searching Authority relating to corresponding International Patent Application No. PCT/US2015/039692, filed Jul. 9, 2015. Date of Mailing: Sep. 30, 2015.
Written Opinion of the International Searching Authority relating to corresponding International Patent Application No. PCT/US2015/039692, filed Jul. 9, 2015. Date of Mailing: Sep. 30, 2015.
Briscoe et al., "The Orphan G Protein-coupled Receptor GPR40 is Activated by Medium and Long Chain Fatty Acids.", J. Biol. Chem., 2003, pp. 11303-11311, vol. 278.
Edfalk et al., "Gpr40 is Expressed in Enteroendocrine Cells and Mediates Free Fatty Acid Stimulation of Incretin Secretion.", Diabetes, 2008, pp. 2280-2287, vol. 57.
Itoh et al., "Free fatty acids regulate insulin secretion from pancreatic β cells through GPR40", Nature, Mar. 13, 2003, pp. 173-176, vol. 422.
Kotarsky et al., "A human cell surface receptor activated by free fatty acids and thiazolidinedione drugs.", Biochem. Biophys. Res. Commun., 2003, pp. 406-410, vol. 301.

* cited by examiner

Primary Examiner — Douglas M Willis

(57) ABSTRACT

Disclosed are compounds, compositions and methods for treating of disorders that are affected by the modulation of the GPR40 receptor. Such compounds are represented by Formula (I) as follows:

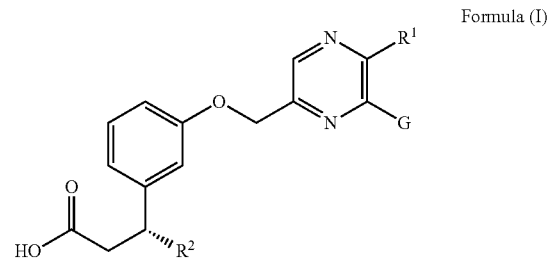

wherein $R^1$, G, and $R^2$ are defined herein.

19 Claims, No Drawings

SUBSTITUTED PYRAZINES AS GPR40 AGONISTS

CROSS-REFERENCE TO RELATED APPLICATIONS

This application claims the benefit of U.S. Provisional Application No. 62/022,257, filed on Jul. 9, 2014, which is incorporated by reference herein in it's entirety.

FIELD OF THE INVENTION

The present invention relates to novel compounds which are GPR40 agonists and are useful for the treatment of disorders that are affected by the modulation of the GPR40 receptor. The invention also relates to pharmaceutical compositions comprising one or more of such compounds, to processes to prepare such compounds and compositions, and to the use of such compounds or pharmaceutical compositions for the treatment of various diseases, syndromes and disorders, including Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, that are related to GPR40 modulation.

BACKGROUND OF THE INVENTION

Diabetes is a rapidly expanding, devastating disease that currently affects over 371 million people in the world, with associated healthcare costs exceeding 470 billion dollars in the USA alone. There are two main types of diabetes. Type 1 diabetes affects ~10% of the patients and is characterized by complete insulinopenia due to autoimmune destruction of the insulin-secreting pancreatic beta cells. Treatment of Type 1 diabetes requires insulin therapy. Type 2 diabetes affects ~90% of the patients and is a polygenic syndrome with not only a hereditary component but also a strong environmental influence. It is caused by insulin resistance and defective insulin secretion. In most individuals, the pancreatic beta cell compensates for obesity-associated insulin resistance by expanding its functional mass and secretion of insulin. In a subset of ~20% of obese subjects, beta cell compensation fails and Type 2 diabetes develops. Two major classes of type 2 diabetes drugs are insulin sensitizers (e.g. metformin, thiazolidinediones) and insulin secretagogues (e.g. sulfonylureas, glinides, glucagon-like peptide-1 (GLP-1)-based drugs). Most of the recently approved drugs belong to the latter category and are based on the GLP-1 mechanism, either by pharmacologically enhancing GLP-1 levels (GLP-1 agonists) or by inhibiting the degradation of endogenous GLP-1 (dipeptidyl-peptidase 4 inhibitors). One advantageous feature of these drugs is that they only stimulate insulin secretion when blood glucose levels are elevated (as opposed to sulfonylureas and glinides), thus minimizing the risk of iatrogenic hypoglycemia. A decade ago, the discovery of the G-protein-coupled receptor GPR40 as a fatty acid receptor specifically expressed in beta cells and which stimulates glucose-dependent insulin secretion, sparked interest in the pharmaceutical industry as a potential therapeutic target to enhance insulin secretion in type 2 diabetes, in a manner similar to GLP-1-based drugs. GPR40, also known as free fatty acid receptor 1 (FFAR1), is one of a family of G-protein coupled receptors that, through receptor deorphanization studies, was shown to be endogenously activated by medium- to long-chain saturated and unsaturated fatty acids ($\sim C_{12-20}$) (Brisco, et al., 2003, J. Biol. Chem., vol. 278: pgs 11303-11311; Itoh, et al., 2003, Nature, vol. 422, pgs 173-176; Kotarsky et al., 2003, Biochem. Biophys. Res. Commun., vol. 301, pgs 406-410). In humans and rodents, although present in brain and enteroendocrine cells, its expression is particularly high in pancreatic beta cells and enteroendocrine cells in the gut. Operating primarily through $G\alpha_{q/11}$ signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (Edfalk, et al., 2008, Diabetes, vol. 57, pgs 2280-2287). Thus, in addition to directly promoting GSIS from islet beta cells, GPR40 activation in enteroendocrine cells provides an indirect means of stimulating GSIS through the actions of released incretins.

Because of the glucose dependency of GPR40-mediated effects on insulin secretion, selective activation of this receptor provides a unique potential therapeutic mechanism by which to treat the diabetic state with minimal risk of hypoglycemic incidents. Given the relatively restricted tissue expression pattern of GPR40, selective GPR40 agonists may offer the additional advantage of providing an improved safety profile relative to the aforementioned therapeutic agents.

Thus, GPR40 agonists of the present invention may provide therapeutic benefit for the treatment of diabetes, particularly Type 2 diabetes, as well as diseases, syndromes and disorders, including obesity, obesity-related disorders, impaired glucose tolerance, insulin resistance, metabolic syndrome, other cardiovascular risk factors such as hypertension and and cardiovascular risk factors related to unmanaged cholesterol and/or lipid levels, osteoporosis, inflammation, and eczema.

SUMMARY OF THE INVENTION

The present invention is directed to compounds of Formula (I)

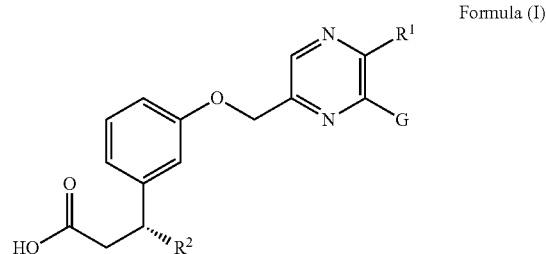

Formula (I)

wherein $R^1$ is selected from the group consisting of phenyl, pyridin-4-yl, and thiophenyl; wherein $R^1$ is optionally independently substituted with one or two substituents that are $C_{1-4}$alkyl, methoxy, fluoro, cyano, or trifluoromethyl; provided that phenyl of $R^1$ is substituted with no more than one methoxy substituent;

G is selected from the group consisting of $C_{1-6}$alkyl; $C_{1-6}$alkoxy; $C_{3-7}$cycloalkyl; 2,2,6,6-tetramethyltetrahydro-2H-pyran-4-yloxy; oxetan-3-yloxy; $C_{2-6}$alk-1-en-1-yl; 3,3,3-trifluoropropyloxy; 1,1,1-trifluoroprop-2-yl; ($C_{1-6}$alkyl)thiophen-2-yl; phenyl optionally substituted with one to two $C_{1-4}$alkyl substituents; $(C_{1-6}$alkyl)amino; di$(C_{1-6}$alkyl)amino; heterocyclyl wherein said heterocyclyl is attached to the core pyrazine ring via a nitrogen atom and said heterocyclyl is optionally spirofused to a $C_{3-7}$cycloalkyl group; ring g1

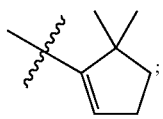

g1

$C_{3-7}$cycloalkyloxy; and $C_{3-7}$cycloalkyl-methoxy;

wherein $C_{3-7}$cycloalkyloxy and the $C_{3-7}$cycloalkyl portion of $C_{3-7}$cycloalkyl-methoxy are optionally substituted with one to four methyl substituents;

$R^2$ is $C_{3-5}$cycloalkyl, $C_{1-6}$alkyl, or cyano;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of GPR40, such as Type II diabetes mellitus, using a compound of Formula (I).

The present invention also is also directed to the use of any of the compounds described herein in the preparation of a medicament wherein the medicament is prepared for treating a disease or condition that is affected by the agonism of GPR40, selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, in a subject in need thereof.

The present invention is also directed to the preparation of substituted pyrazine derivatives that act as selective agonists of the GPR40 receptor.

Exemplifying the invention are methods of treating a disorder modulated by GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, comprising administering to a subject in need thereof a therapeutically effective amount of any of the compounds or pharmaceutical compositions described above.

In another embodiment, the present invention is directed to a compound of Formula (I) for use in the treatment of a disorder affected by the agonism of GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

In another embodiment, the present invention is directed to a composition comprising a compound of Formula (I) for the treatment of a disorder affected by the agonism of GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}$alkyl$)_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.
The term "formyl" refers to the group —C(=O)H.
The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

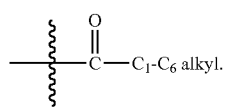

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR40 agonist" is intended to encompass a compound that interacts with GPR40 to substantially increase its catalytic activity, thereby increasing the concentrations of its substrate(s).

The term "GPR40-modulated" is used to refer to the condition of being affected by the modulation of the GPR40 receptor, including but not limited to, the state of being mediated by the GPR40 receptor, for the treatment of a disease or condition such as Type II diabetes or impaired glucose tolerance.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitably examples include, but are not limited to Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema; more preferably, Type II diabetes mellitus and impaired glucose tolerance.

As used herein unless otherwise noted, the term "cardiovascular risk factors" shall mean any cardiovascular disease, disorder or condition in which obesity or diabetes (preferably, Type II diabetes) has a role in the initiation or exacerbation of said disorder or condition. Suitable examples include, but are not limited to, hypertension, atherosclerosis and cardiac fibrosis.

As used herein, unless otherwise noted, the term "affect" or "affected" (when referring to a disease, syndrome, condition or disorder that is affected by agonism of GPR40) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of GPR40 receptor. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt form thereof are useful for treating or ameliorating diseases, syndromes, conditions, or disorders such as Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

More particularly, the compounds of Formula (I), or an enantiomer, diastereomer, solvate or pharmaceutically acceptable salt form thereof are useful for treating or ameliorating Type II diabetes mellitus or impaired glucose tolerance, comprising administering to a subject in need thereof a therapeutically effective amount of a compound of Formula (I), or an enantiomer, diastereomer, solvate or pharmaceutically acceptable salt form thereof as herein defined.

Embodiments of the present invention include a compound of Formula (I)

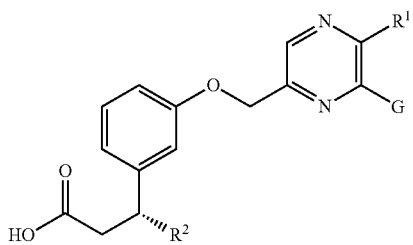

Formula (I)

wherein
a) $R^1$ is selected from the group consisting of phenyl and pyridin-4-yl; wherein $R^1$ is independently substituted with one or two substituents that are methoxy and fluoro; provided that phenyl of $R^1$ is substituted with no more than one methoxy substituent;

b) $R^1$ is 2-fluoro-5-methoxyphenyl or 5-fluoro-2-methoxy-pyridin-4-yl;
c) G is selected from the group consisting of $C_{1-6}$alkyl; $C_{1-6}$alkoxy; 2,2,6,6-tetramethyltetrahydro-2H-pyran-4-yloxy; $C_{2-6}$alk-1-en-1-yl; 3,3,3-trifluoropropyloxy; ($C_{1-6}$alkyl)thiophen-2-yl; phenyl optionally substituted with one to two $C_{1-4}$alkyl substituents; heterocyclyl wherein said heterocyclyl is attached to the core pyrazine ring via a nitrogen atom and said heterocyclyl is optionally spiro-fused to a $C_{3-7}$cycloalkyl group; ring g1

$C_{3-7}$cycloalkyloxy; and $C_{3-7}$cycloalkyl-methoxy;
wherein said $C_{3-7}$cycloalkyloxy and the $C_{3-7}$cycloalkyl portion of $C_{3-7}$cycloalkyl-methoxy are optionally substituted with one to four methyl substituents;
d) G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)thiophen-2-yl; phenyl optionally substituted with one to two $C_{1-4}$alkyl substituents; heterocyclyl wherein said heterocyclyl is selected from the group consisting of piperidin-1-yl and azetidin-1-yl, and said heterocyclyl is optionally spirofused to a $C_{3-7}$cycloalkyl; ring g1

$C_{3-7}$cycloalkyloxy; and $C_{3-7}$cycloalkyl-methoxy;
wherein said $C_{3-7}$cycloalkyloxy and the $C_{3-7}$cycloalkyl portion of $C_{3-7}$cycloalkyl-methoxy are optionally substituted with one to four methyl substituents;
e) $R^2$ is $C_{3-5}$cycloalkyl;
f) $R^2$ is cyclopropyl;
and any combination of embodiments a) through f) above, provided that it is understood that combinations in which different embodiments of the same substituent would be combined are excluded;
or an enantiomer, diastereomer, or pharmaceutically acceptable salt form thereof.

An embodiment of the present invention includes a compound of Formula (I)

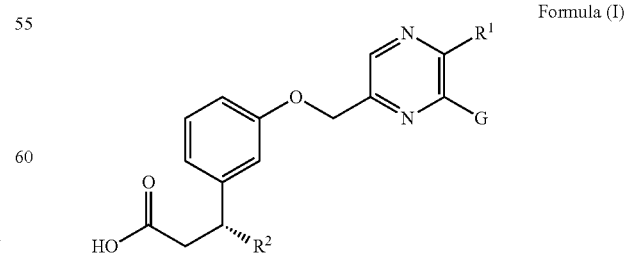

Formula (I)

wherein
$R^1$ is selected from the group consisting of phenyl and pyridin-4-yl; wherein $R^1$ is independently substituted with one or two substituents that are methoxy and fluoro; provided that phenyl of R¹ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-6}$alk-1-en-1-yl; 3,3,3-trifluoropropyloxy; ($C_{1-6}$ alkyl)thiophen-2-yl; phenyl optionally substituted with one to two $C_{1-4}$alkyl substituents; heterocyclyl wherein said heterocyclyl is attached to the core pyrazine ring via a nitrogen atom and said heterocyclyl is optionally spirofused to a $C_{3-7}$cycloalkyl group; ring g1

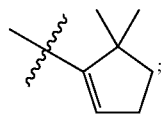

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents;

R² is $C_{3-5}$cycloalkyl;

or an enantiomer, diastereomer, or pharmaceutically acceptable salt form thereof.

An embodiment of the present invention includes a compound of Formula (I)

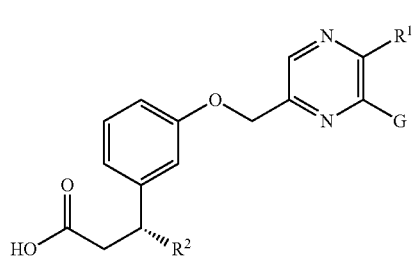

wherein

R¹ is selected from the group consisting of phenyl and pyridin-4-yl; wherein R¹ is independently substituted with one or two substituents that are methoxy and fluoro; provided that phenyl of R¹ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)thiophen-2-yl; phenyl optionally substituted with one to two $C_{1-4}$alkyl substituents; heterocyclyl wherein said heterocyclyl is selected from the group consisting of piperidin-1-yl and azetidin-1-yl and said heterocyclyl is optionally spirofused to a $C_{3-7}$cycloalkyl; ring g1

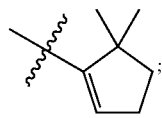

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents;

R² is $C_{3-5}$cycloalkyl;

or an enantiomer, diastereomer, or pharmaceutically acceptable salt form thereof.

An embodiment of the present invention includes a compound of Formula (I)

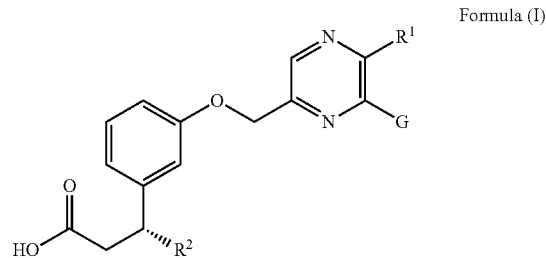

wherein

R¹ is selected from the group consisting of phenyl and pyridin-4-yl; wherein R¹ is independently substituted with one or two substituents that are methoxy and fluoro; provided that phenyl of R¹ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)thiophen-2-yl; phenyl optionally substituted with one to two $C_{1-4}$alkyl substituents; heterocyclyl wherein said heterocyclyl is selected from the group consisting of piperidin-1-yl and azetidin-1-yl and said heterocyclyl is optionally spirofused to a $C_{3-7}$cycloalkyl; ring g1

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents;

R² is cyclopropyl;

or an enantiomer, diastereomer, or pharmaceutically acceptable salt form thereof.

An embodiment of the present invention includes a compound of Formula (I)

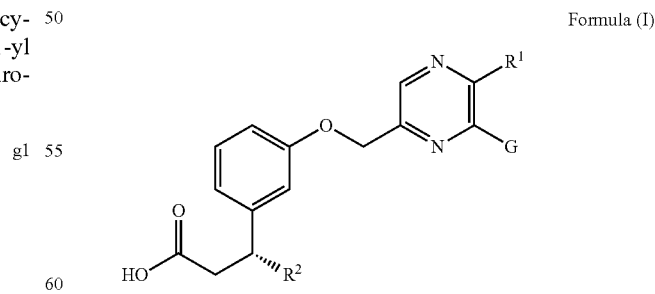

wherein

R¹ is 2-fluoro-5-methoxyphenyl or 5-fluoro-2-methoxypyridin-4-yl;

G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)

thiophen-2-yl; phenyl optionally substituted with one to two $C_{1-4}$alkyl substituents; heterocyclyl wherein said heterocyclyl is azetidinyl and said azetidinyl is optionally spirofused to a $C_{3-7}$cycloalkyl group to form 2-azaspiro[3.3]heptan-2-yl; ring g1

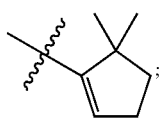

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents;

$R^2$ is cyclopropyl;

or an enantiomer, diastereomer, or pharmaceutically acceptable salt form thereof.

An embodiment of the present invention includes a compound of Formula (I)

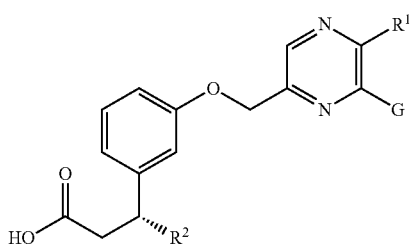

Formula (I)

wherein $R^1$ is 2-fluoro-5-methoxyphenyl or 5-fluoro-2-methoxy-pyridin-4-yl;

G is selected from the group consisting of 2,2-dimethylpropyl, isobutyl, n-butyl, 2,2-dimethylpropyloxy, 2-azaspiro[3.3]heptan-2-yl, cyclohexyloxy, 2-methyl prop-1-enyl, 3,5-dimethylphenyl, isobutyloxy, cyclopentyloxy, 5,5-dimethyl cyclopenten-1-yl, (2,2,3,3-tetramethyl cyclopropyl)methoxy, phenyl, cyclobutyloxy, 3-methylphenyl, cyclopropylmethoxy, 3-isopropylphenyl, 4-isopropylphenyl, (2,2,6,6-tetramethyl tetrahydropyran-4-yl)oxy, cycloheptyloxy, 5-methylthien-2-yl, isopropyloxy, 3,3,3-trifluoropropyloxy, 3-methylthien-2-yl, isopropyl(methyl)amino, isopropyl, dimethylamino, cyclopropyl, 2,2,2-trifluoro-1-methyl-ethyl, oxetan-3-yloxy, (3,3-dimethylcyclobutyl)methoxy, 5-(t-butyl)thien-2-yl, 2,2-dimethylpropylamino, morpholin-4-yl, and cyclopropylmethoxy;

$R^2$ is cyclopropyl;

or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, wherein the substituents selected from one or more of the variables defined herein (e.g. $R^1$, $R^2$, and G) are independently selected to be any individual substituent or any subset of substituents from those exemplified in the listing in Table 1, below.

TABLE 1

Compounds of Formula (I)

| Cpd No. | $R^1$ | $R^2$ | G |
|---|---|---|---|
| 1 | 2-fluoro-5-methoxyphenyl | cyclopropyl | 2,2-dimethylpropyl |
| 2 | 5-fluoro-2-methoxypyridin-4-yl | cyclopropyl | isobutyl |
| 3 | 2-fluoro-5-methoxyphenyl | cyclopropyl | n-butyl |
| 4 | 2-fluoro-5-methoxyphenyl | cyclopropyl | 2,2-dimethylpropyloxy |
| 5 | 2-fluoro-5-methoxyphenyl | cyclopropyl | isobutyl |
| 6 | 2-fluoro-5-methoxyphenyl | cyclopropyl | 2-azaspiro[3.3]heptan-2-yl |
| 7 | 2-fluoro-5-methoxyphenyl | cyclopropyl | cyclohexyloxy |
| 8 | 2-fluoro-5-methoxyphenyl | cyclopropyl | 2-methyl prop-1-enyl |
| 9 | 5-fluoro-2-methoxypyridin-4-yl | cyclopropyl | cyclohexyloxy |
| 10 | 2-fluoro-5-methoxyphenyl | cyclopropyl | 3,5-dimethylphenyl |
| 11 | 5-fluoro-2-methoxypyridin-4-yl | cyclopropyl | 2-methyl prop-1-enyl |
| 12 | 5-fluoro-2-methoxy-4-pyridyl | cyclopropyl | isobutyloxy |
| 13 | 2-fluoro-5-methoxyphenyl | cyclopropyl | cyclopentyloxy |
| 14 | 2-fluoro-5-methoxyphenyl | cyclopropyl | isobutyloxy |
| 15 | 5-fluoro-2-methoxypyridin-4-yl | cyclopropyl | 5,5-dimethyl cyclopenten-1-yl |
| 16 | 5-fluoro-2-methoxypyridin-4-yl | cyclopropyl | cyclopentyloxy |
| 17 | 2-fluoro-5-methoxyphenyl | cyclopropyl | (2,2,3,3-tetramethyl cyclopropyl) methoxy |
| 18 | 2-fluoro-5-methoxyphenyl | cyclopropyl | phenyl |
| 19 | 2-fluoro-5-methoxyphenyl | cyclopropyl | cyclobutyloxy |
| 20 | 2-fluoro-5-methoxyphenyl | cyclopropyl | 3-methylphenyl |
| 21 | 2-fluoro-5-methoxyphenyl | cyclopropyl | cyclopropyl methoxy |

TABLE 1-continued

Compounds of Formula (I)

Formula (I)

| Cpd No. | R¹ | R² | G |
|---|---|---|---|
| 22 | 2-fluoro-5-methoxy-phenyl | cyclopropyl | piperidin-1-yl |
| 23 | 2-fluoro-5-methoxy-phenyl | cyclopropyl | 3-isopropylphenyl |
| 24 | 2-fluoro-5-methoxy-phenyl | cyclopropyl | 3,3,5,5-tetramethyl cyclohexyloxy |
| 25 | 2-fluoro-5-methoxy-phenyl | cyclopropyl | 4-isopropylphenyl |
| 26 | 2-fluoro-5-methoxy-phenyl | cyclopropyl | (2,2,6,6-tetramethyl tetrahydropyran-4-yl)oxy |
| 27 | 2-fluoro-5-methoxy-phenyl | cyclopropyl | cycloheptyloxy |
| 28 | 5-fluoro-2-methoxy-pyridin-4-yl | cyclopropyl | 5-methylthien-2-yl |
| 29 | 2-fluoro-5-methoxy-phenyl | cyclopropyl | isopropyloxy |
| 30 | 2-fluoro-5-methoxy-phenyl | cyclopropyl | 5,5-dimethyl cyclopenten-1-yl |
| 31 | 2-methoxy-pyridin-4-yl | cyclopropyl | 5,5-dimethyl cyclopenten-1-yl |
| 32 | 2-fluoro-5-methoxy-phenyl | cyclopropyl | 3,3,3-trifluoropropyloxy |
| 33 | 2-fluoro-5-methoxy-phenyl | cyclopropyl | 3-methylthien-2-yl |
| 34 | 2-fluoro-5-methoxy-phenyl | cyclopropyl | isopropyl(methyl)amino |
| 35 | 3-methoxy phenyl | cyclopropyl | 5,5-dimethyl cyclopenten-1-yl |
| 36 | 2-fluoro-5-methoxy-phenyl | cyclopropyl | 5-methylthien-2-yl |
| 37 | 2-fluoro-5-methoxy-phenyl | cyclopropyl | isopropyl |
| 38 | 2-fluoro-5-methoxy-phenyl | cyclopropyl | dimethylamino |
| 39 | 2-fluoro-5-methoxy-phenyl | cyclopropyl | cyclopropyl |
| 40 | 2-fluoro-5-methoxy-phenyl | cyclopropyl | 2,2,2-trifluoro-1-methyl-ethyl |
| 41 | 2-fluoro-5-methoxy-phenyl | cyclopropyl | oxetan-3-yloxy |
| 42 | 2-fluoro-5-methoxy-phenyl | cyclopropyl | (3,3-dimethylcyclobutyl) methoxy |
| 43 | 2-fluoro-5-methoxy-phenyl | cyclopropyl | 5-(t-butyl)thien-2-yl |
| 44 | 2-fluoro-5-methoxy-phenyl | cyclopropyl | 2,2-dimethylpropyl amino |
| 45 | 2-fluoro-5-methoxy-phenyl | cyclopropyl | morpholin-4-yl |
| 46 | 2-fluoro-3-methoxy-phenyl | cyclopropyl | 5,5-dimethyl cyclopenten-1-yl |
| 47 | 5-fluoro-2-methoxy-pyridin-4-yl | cyclopropyl | 2,2-dimethylpropyloxy |
| 48 | 5-fluoro-2-methoxy-pyridin-4-yl | cyclopropyl | cyclopropyl methoxy |

Further embodiments of the present invention are directed to a compound of Formula (I)

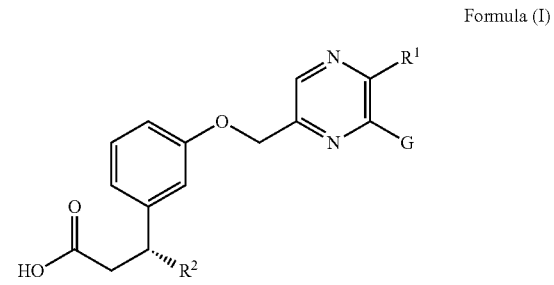

Formula (I)

selected from the group consisting of

Cpd 1, (3S)-3-cyclopropyl-3-[3-[[6-(2,2-dimethylpropyl)-5-(2-fluoro-5-methoxy-phenyl)pyrazin-2-yl]methoxy]phenyl]propanoic acid;

Cpd 2, (3S)-3-cyclopropyl-3-[3-[[5-(5-fluoro-2-methoxy-4-pyridyl)-6-isobutyl-pyrazin-2-yl]methoxy]phenyl]propanoic acid;

Cpd 3, (3S)-3-[3-[[6-butyl-5-(2-fluoro-5-methoxy-phenyl)pyrazin-2-yl]methoxy]phenyl]-3-cyclopropyl-propanoic acid;

Cpd 4, (3S)-3-cyclopropyl-3-[3-[[6-(2,2-dimethylpropoxy)-5-(2-fluoro-5-methoxy-phenyl)pyrazin-2-yl]methoxy] phenyl]propanoic acid;

Cpd 5, (3S)-3-cyclopropyl-3-[3-[[5-(2-fluoro-5-methoxy-phenyl)-6-isobutyl-pyrazin-2-yl]methoxy]phenyl]propanoic acid;

Cpd 6, (3S)-3-[3-[(6-[2-azaspiro[3.3]heptan-2-yl]-5-(2-fluoro-5-methoxyphenyl)pyrazin-2-yl)methoxy]phenyl]-3-cyclopropylpropanoic acid;

Cpd 7, (3S)-3-[3-[[6-(cyclohexoxy)-5-(2-fluoro-5-methoxy-phenyl)pyrazin-2-yl]methoxy]phenyl]-3-cyclopropyl-propanoic acid;

Cpd 8, (3S)-3-cyclopropyl-3-[3-[[5-(2-fluoro-5-methoxy-phenyl)-6-(2-methylprop-1-enyl)pyrazin-2-yl]methoxy]phenyl]propanoic acid;

Cpd 9, (3S)-3-[3-[[6-(cyclohexoxy)-5-(5-fluoro-2-methoxy-4-pyridyl)pyrazin-2-yl]methoxy]phenyl]-3-cyclopropyl-propanoic acid;

Cpd 10, (3S)-3-cyclopropyl-3-[3-[[6-(3,5-dimethylphenyl)-5-(2-fluoro-5-methoxy-phenyl)pyrazin-2-yl]methoxy]phenyl]propanoic acid;

Cpd 11, (3S)-3-cyclopropyl-3-[3-[[5-(5-fluoro-2-methoxy-4-pyridyl)-6-(2-methylprop-1-enyl)pyrazin-2-yl]methoxy]phenyl]propanoic acid;

Cpd 12, (3S)-3-cyclopropyl-3-[3-[[5-(5-fluoro-2-methoxy-4-pyridyl)-6-isobutoxy-pyrazin-2-yl]methoxy]phenyl]propanoic acid;

Cpd 13, (3S)-3-[3-[[6-(cyclopentoxy)-5-(2-fluoro-5-methoxy-phenyl)pyrazin-2-yl]methoxy]phenyl]-3-cyclopropyl-propanoic acid;

Cpd 14, (3S)-3-cyclopropyl-3-[3-[[5-(2-fluoro-5-methoxy-phenyl)-6-isobutoxy-pyrazin-2-yl]methoxy]phenyl]propanoic acid;

Cpd 15, (3S)-3-cyclopropyl-3-[3-[[6-(5,5-dimethylcyclopenten-1-yl)-5-(5-fluoro-2-methoxy-4-pyridyl)pyrazin-2-yl]methoxy]phenyl]propanoic acid;

Cpd 16, (3S)-3-[3-[[6-(cyclopentoxy)-5-(5-fluoro-2-methoxy-4-pyridyl)pyrazin-2-yl]methoxy]phenyl]-3-cyclopropyl-propanoic acid;

Cpd 17, (3S)-3-cyclopropyl-3-[3-[[5-(2-fluoro-5-methoxy-phenyl)-6-[(2,2,3,3-tetramethylcyclopropyl)methoxy]pyrazin-2-yl]methoxy]phenyl]propanoic acid;

Cpd 18, (3S)-3-cyclopropyl-3-[3-[[5-(2-fluoro-5-methoxy-phenyl)-6-phenyl-pyrazin-2-yl]methoxy]phenyl]propanoic acid;

Cpd 19, (3S)-3-[3-[[6-(cyclobutoxy)-5-(2-fluoro-5-methoxy-phenyl)pyrazin-2-yl]methoxy]phenyl]-3-cyclopropyl-propanoic acid;

Cpd 20, (3S)-3-cyclopropyl-3-[3-[[5-(2-fluoro-5-methoxy-phenyl)-6-(m-tolyl)pyrazin-2-yl]methoxy]phenyl]propanoic acid;

Cpd 21, (3S)-3-cyclopropyl-3-[3-[[6-(cyclopropyl-methoxy)-5-(2-fluoro-5-methoxy-phenyl)pyrazin-2-yl]methoxy]phenyl]propanoic acid;

Cpd 22, (3S)-3-cyclopropyl-3-[3-[[5-(2-fluoro-5-methoxy-phenyl)-6-(1-piperidyl)pyrazin-2-yl]methoxy]phenyl]propanoic acid;

Cpd 23, (3S)-3-cyclopropyl-3-[3-[[5-(2-fluoro-5-methoxy-phenyl)-6-(3-isopropylphenyl)pyrazin-2-yl]methoxy]phenyl]propanoic acid;

Cpd 24, (3S)-3-cyclopropyl-3-[3-[[5-(2-fluoro-5-methoxy-phenyl)-6-(3,3,5,5-tetramethylcyclohexoxy)pyrazin-2-yl]methoxy]phenyl]propanoic acid;

Cpd 25, (3S)-3-cyclopropyl-3-[3-[[5-(2-fluoro-5-methoxy-phenyl)-6-(4-isopropylphenyl)pyrazin-2-yl]methoxy]phenyl]propanoic acid;

Cpd 26, (3S)-3-cyclopropyl-3-[3-[[5-(2-fluoro-5-methoxy-phenyl)-6-(2,2,6,6-tetramethyltetrahydropyran-4-yl)oxy-pyrazin-2-yl]methoxy]phenyl]propanoic acid;

Cpd 27, (3S)-3-[3-[[6-(cycloheptoxy)-5-(2-fluoro-5-methoxy-phenyl)pyrazin-2-yl]methoxy]phenyl]-3-cyclopropyl-propanoic acid;

Cpd 28, (3S)-3-cyclopropyl-3-[3-[[5-(5-fluoro-2-methoxy-4-pyridyl)-6-(5-methyl-2-thienyl)pyrazin-2-yl]methoxy]phenyl]propanoic acid;

Cpd 29, (3S)-3-cyclopropyl-3-[3-[[5-(2-fluoro-5-methoxy-phenyl)-6-isopropoxy-pyrazin-2-yl]methoxy]phenyl]propanoic acid;

Cpd 30, (3S)-3-cyclopropyl-3-[3-[[6-(5,5-dimethylcyclopenten-1-yl)-5-(2-fluoro-5-methoxy-phenyl)pyrazin-2-yl]methoxy]phenyl]propanoic acid;

Cpd 31, (3S)-3-cyclopropyl-3-[3-[[6-(5,5-dimethylcyclopenten-1-yl)-5-(2-methoxy-4-pyridyl)pyrazin-2-yl]methoxy]phenyl]propanoic acid;

Cpd 32, (3S)-3-cyclopropyl-3-[3-[[5-(2-fluoro-5-methoxy-phenyl)-6-(3,3,3-trifluoropropoxy)pyrazin-2-yl]methoxy]phenyl]propanoic acid;

Cpd 33, (3S)-3-cyclopropyl-3-[3-[[5-(2-fluoro-5-methoxy-phenyl)-6-(3-methyl-2-thienyl)pyrazin-2-yl]methoxy]phenyl]propanoic acid;

Cpd 34, (3S)-3-cyclopropyl-3-[3-[[5-(2-fluoro-5-methoxy-phenyl)-6-[isopropyl(methyl)amino]pyrazin-2-yl]methoxy]phenyl]propanoic acid;

Cpd 35, (3S)-3-cyclopropyl-3-[3-[[6-(5,5-dimethylcyclopenten-1-yl)-5-(3-methoxyphenyl)pyrazin-2-yl]methoxy]phenyl]propanoic acid;

Cpd 36, (3S)-3-cyclopropyl-3-[3-[[5-(2-fluoro-5-methoxy-phenyl)-6-(5-methyl-2-thienyl)pyrazin-2-yl]methoxy]phenyl]propanoic acid;

Cpd 37, (3S)-3-cyclopropyl-3-[3-[[5-(2-fluoro-5-methoxy-phenyl)-6-isopropyl-pyrazin-2-yl]methoxy]phenyl]propanoic acid;

Cpd 38, (3S)-3-cyclopropyl-3-[3-[[6-(dimethylamino)-5-(2-fluoro-5-methoxy-phenyl)pyrazin-2-yl]methoxy]phenyl]propanoic acid;

Cpd 39, (3S)-3-cyclopropyl-3-[3-[[6-cyclopropyl-5-(2-fluoro-5-methoxy-phenyl)pyrazin-2-yl]methoxy]phenyl]propanoic acid;

Cpd 40, (3S)-3-cyclopropyl-3-[3-[[5-(2-fluoro-5-methoxy-phenyl)-6-(2,2,2-trifluoro-1-methyl-ethyl)pyrazin-2-yl]methoxy]phenyl]propanoic acid;

Cpd 41, (3S)-3-cyclopropyl-3-[3-[[5-(2-fluoro-5-methoxy-phenyl)-6-(oxetan-3-yloxy)pyrazin-2-yl]methoxy]phenyl]propanoic acid;

Cpd 42, (3S)-3-cyclopropyl-3-[3-[[6-[(3,3-dimethylcyclobutyl)methoxy]-5-(2-fluoro-5-methoxy-phenyl)pyrazin-2-yl]methoxy]phenyl]propanoic acid;

Cpd 43, (3S)-3-[3-[[6-(5-tert-butyl-2-thienyl)-5-(2-fluoro-5-methoxy-phenyl)pyrazin-2-yl]methoxy]phenyl]-3-cyclopropyl-propanoic acid;

Cpd 44, (3S)-3-cyclopropyl-3-[3-[[6-(2,2-dimethylpropylamino)-5-(2-fluoro-5-methoxy-phenyl)pyrazin-2-yl]methoxy]phenyl]propanoic acid;

Cpd 45, (3S)-3-cyclopropyl-3-[3-[[5-(2-fluoro-5-methoxy-phenyl)-6-morpholinopyrazin-2-yl]methoxy]phenyl]propanoic acid;

Cpd 46, (3S)-3-cyclopropyl-3-[3-[[6-(5,5-dimethylcyclopenten-1-yl)-5-(2-fluoro-3-methoxy-phenyl)pyrazin-2-yl]methoxy]phenyl]propanoic acid;

Cpd 47, (3S)-3-cyclopropyl-3-[3-[[6-(2,2-dimethylpropoxy)-5-(5-fluoro-2-methoxy-4-pyridyl)pyrazin-2-yl]methoxy]phenyl]propanoic acid; and Cpd 48, (3S)-3-cyclopropyl-3-[3-[[6-(cyclopropyl-methoxy)-5-(5-fluoro-2-methoxy-4-pyridyl)pyrazin-2-yl]methoxy]phenyl]propanoic acid;

or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glutamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As GPR40 agonists, the compounds of Formula (I) are useful in methods for treating or preventing a disease, a syndrome, a condition or a disorder in a subject, including an animal, a mammal and a human in which the disease, the syndrome, the condition or the disorder is affected by the modulation, including agonism, of the GPR40 receptor. Such methods comprise, consist of and/or consist essentially of administering to a subject, including an animal, a mammal, and a human, in need of such treatment or prevention, a therapeutically effective amount of a compound, salt or solvate of Formula (I).

In another embodiment, the present invention is directed to a compound of Formula (I) for use in the treatment of a disorder affected by the agonism of GPR40 receptor selected from the group consisting of Type 2 diabetes mellitus, obesity, obesity related disorders, impaired glucose tolerance, insulin resistance, metabolic syndrome, other cardiovascular risk factors such as hypertension and cholesterol/lipids, osteoporosis, inflammation and eczema; preferably, Type II diabetes mellitus, metabolic syndrome, and impaired glucose tolerance; more preferably, Type II diabetes mellitus or impaired glucose tolerance.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
ADDP azodicarboxylic dipiperidide
aq. aqueous
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DEAD diethyl azodicarboxylate
DIBAL diisobutylaluminum hydride
DIPEA or DIEA diisopropyl-ethyl amine
DMA dimethylaniline
DMAP 4-dimethylaminopyridine
DME dimethoxyethane
DMF N,N-dimethylformamide
DMSO dimethylsulfoxide
DPPA diphenylphosphoryl azide
dppf 1,1'-bis(diphenylphosphino)ferrocene
EA ethyl acetate
EDCI 1-ethyl-3-(3-dimethylaminopropyl) carbodiimide
ESI electrospray ionization
EtOAc or EA ethyl acetate
EtOH ethanol
GCMS gas chromatography-mass spectrometry
h or hr(s) hour or hours
HEK human embryonic kidney
HPLC high performance liquid chromatography
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NIS N-iodosuccinimide
NMM N-methylmorpholine
NMP N-methylpyrrolidone
NMR nuclear magnetic resonance
PCC pyridinium chlorochromate
PE petroleum ether
RP reverse-phase
rt or RT room temperature
$R_t$ retention time
Sec second or seconds
SEM-Cl 2-(trimethylsilyl)ethoxymethyl chloride
TBAF tetrabutylammonium fluoride
TBDMS t-butyldimethylsilyl
TBP tributyl phosphate
TEA or $Et_3N$ triethylamine
TFA trifluoroacetic acid
THF tetrahydrofuran
TIPS triisopropylsilyl
TLC thin layer chromatography
TMS tetramethylsilane
Ts 4-toluenesulfonyl General Schemes Scheme A illustrates a method for the preparation of certain compounds of Formula (I) of the present invention.

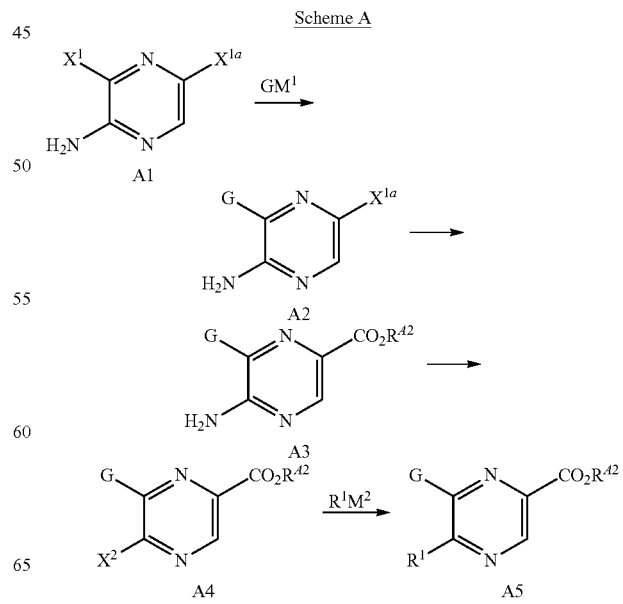

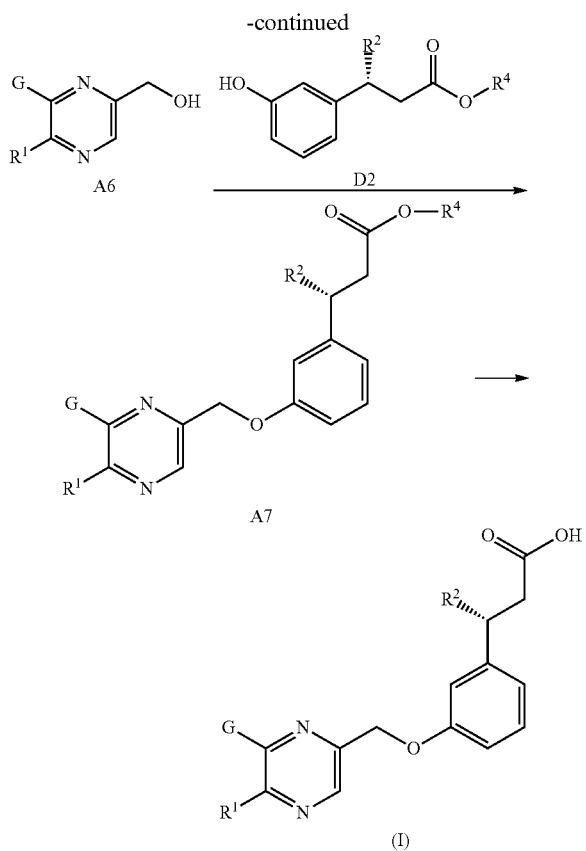

A compound of formula A1, wherein $X^1$ and $X^{1a}$ are independently a halide, preferably chloro or bromo, is either commercially available or may be prepared according to the methods described in the scientific literature. A compound of formula A1 may be reacted with a suitably substituted compound of formula G-M¹, under suitable coupling conditions, to yield the corresponding compound of formula A2. A compound of formula G-M¹ may be (a) a boronic acid to form a compound of formula G-B(OH)₂; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected aryldialkylsilyl such as 2-(hydroxymethyl)phenyl-dimethylsilyl, and the like (f) a suitably selected organo zinc reagent such as G-ZnX wherein X is a halide such as chloro, bromo, or iodo.

For example, a compound of formula G-M¹, wherein M¹ is preferably —B(OH)₂ or a boronic ester, may be reacted with a compound of formula A1 under Suzuki coupling conditions, more particularly in the presence of a suitably selected palladium catalyst such as palladium (II) acetate, palladium (II) chloride, bis(acetonitrile)-dichloro-palladium (II), allylpalladium (II) chloride dimer, tris(dibenzylidineacetone)dipalladium (0) (Pd₂(dba)₃), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ((dppf)PdCl₂.DCM), tetrakis(triphenylphosphine) palladium(0) (Pd(PPh₃)₄), (1,1'-bis(di-tert-butylphosphino)ferrocene palladium (II) chloride, and the like; optionally in the presence of a suitably selected ligand such as triphenylphosphine, tributylphosphine, tri-o-tolyl-phosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, Ru-Phos, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, water, 1,4-dioxane, and the like, or a combination thereof; at a temperature in the range of from about room temperature to about 180° C.

A compound of formula A3, wherein in $R^{42}$ is an alkyl group such as methyl, ethyl or tert-butyl, may be obtained from a compound of formula A2 via a transition metal catalyzed carbonylation. The preferred reaction conditions for this transformation include a transition metal, preferably palladium; a carbonylating agent such as CO; at a pressure of about 1 to about 200 psi; in the presence of an alcohol such as MeOH or EtOH; at a temperature ranging from about room temperature to about 200° C.; and in the presence of a tertiary amine. More preferably, a compound of formula A2 may be reacted with CO in the presence of a Pd catalyst such as Pd(OAc)₂ or Cl₂Pd(PPh₃)₂; in the presence of MeOH; at a pressure between about 20 to 50 psi; in the presence of a tertiary amine such as Et₃N; to obtain a compound of formula A3 wherein $R^{24}$ is methyl. One of ordinary skill in the art will recognize that this transformation may be achieved under a variety of changes to the reaction conditions. For example, a compound of formula A2 wherein $X^{1a}$ is bromo, may undergo a metal-halogen exchange, such as a lithium-bromine exchange, with a protected or unprotected amine. The resulting organometallic intermediate may be reacted with a carbonylating agent such as methylcyanoformate and the like, to obtain a compound of formula A3. Furthermore, this reaction may be used to obtain an intermediate possessing a carboxylic acid, aldehyde, or hydroxymethyl group, useful for subsequent conversion by conventional methods to a compound of formula A3.

A compound of formula A3 may be converted to a compound of formula A4 wherein $X^2$ is a halide. The preferred method for this transformation includes, but is not limited to, the non-aqueous diazotization of the amino group of a compound of formula A3 using a reagent such as tert-butyl nitrite or isoamyl nitrite, followed by the interception of the resulting diazonium salt with an appropriate halogen source such as I₂/CH₂I₂, Cu₂Br₂, Cu₂Cl₂, and the like, to give a compound of formula A4 wherein $X^2$ is iodo, bromo or chloro respectively. It is also understood that this transformation may be effected using standard aqueous Sandmeyer conditions.

The methodologies previously described for the conversion of a compound of formula A1 to a compound of formula A2 may be applied to the conversion of a compound of formula A4 to a compound of formula A5. The ester group of a compound of formula A5 may then be reduced to its corresponding hydroxymethyl group to obtain a compound of formula A6. One of ordinary skill in the art will recognize that there are a variety of reagents and reaction conditions available for this transformation. A preferred set of reaction conditions includes the treatment of a compound of formula A5 in a suitable solvent such as diethyl ether, THF or DCM;

with a hydride source such as LAH or DIBAL-H, or the like; at a temperature of about −78° C. to room temperature. The alcohol of formula A6 may be coupled with a compound of formula D2 under standard Mitsunobu conditions to obtain a compound of formula A7. A preferred method for this transformation includes, but is not limited to, the coupling of a compound of formula A6 with a compound of formula D2 (wherein $R^4$ is methyl, ethyl, or t-butyl); using $PPh_3$ in the presence of a coupling agent such as DEAD; in a suitable aprotic solvent such as THF; at a suitable temperature ranging from about 0° C. to room temperature. Alternatively, the alcohol of a compound of formula A6 may be converted to a leaving group such as a halide, mesylate, or tosylate, which may then be reacted with a compound of formula D2; in the presence of a suitable base such as $Na_2CO_3$, $K_2CO_3$, or $Cs_2CO_3$; in a suitable solvent such as THF, DMF or DMSO; at a suitable temperature. Preferred reaction conditions include, but are not limited to, treatment of a compound of formula A6 with $SOCl_2$; in a solvent such as DCM; at about room temperature; to obtain the corresponding benzyl chloride. The benzyl chloride may then be reacted with a compound of formula D2; in the presence of a suitable base such as $Cs_2CO_3$; in a suitable solvent such as DMF; at about room temperature; to yield a compound of formula A7.

In the final step, the ester functionality of a compound of formula A7 may undergo a conventional saponification to obtain a compound of formula (I). One of ordinary skill in the art will recognize that there are a variety of reagents and reaction conditions available for this conversion. A preferred method for this transformation includes treatment of a compound of formula A7 with an aqueous base such as NaOH, LiOH, and the like; in a solvent such as THF, MeOH, and the like, or a combination thereof; at about room temperature.

Scheme B illustrates an alternative method for the preparation of certain compounds of formula (I) of the present invention.

Scheme B

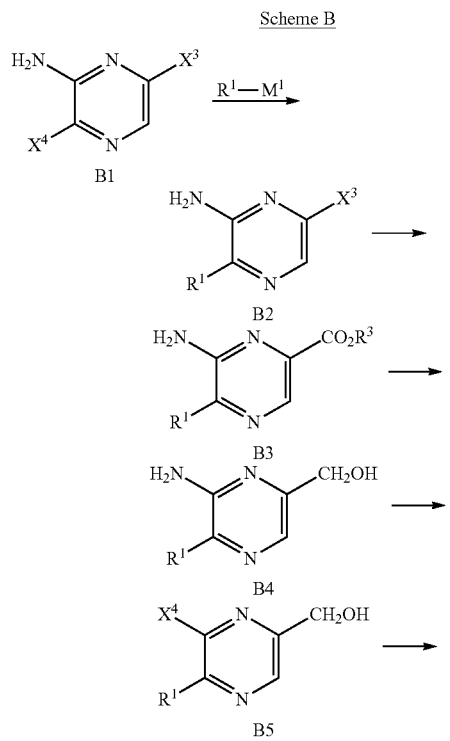

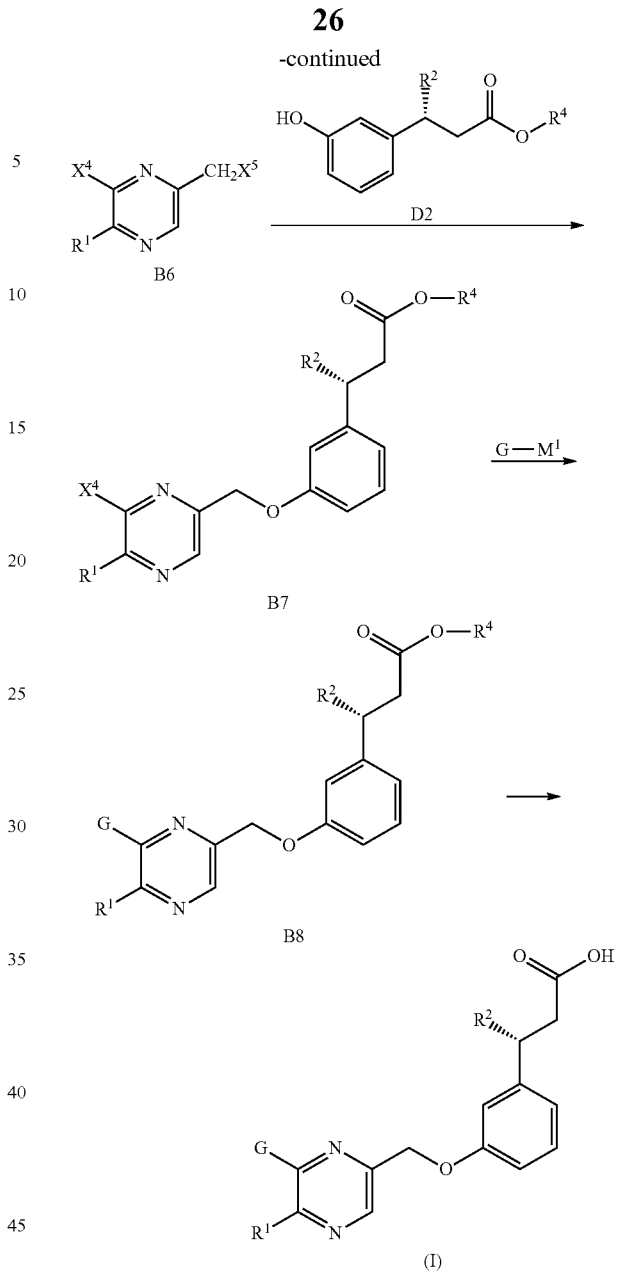

A compound of formula B1, wherein $X^3$ and $X^4$ are independently chloro, bromo, or iodo, is either commercially available or may be prepared according to the methods described in the scientific literature. A compound of formula B2 may be obtained from a compound of formula B1 by reaction with a suitably substituted compound of formula $R^1$-$M^1$ using the methods described in Scheme A for the conversion of a compound of A1 to a compound of formula A2. The remaining halide, $X^3$, of a compound of formula B2 may be useful for the introduction of an ester group of formula —$CO_2R^3$, wherein $R^3$ is methyl, ethyl, or t-butyl, using the method described for the conversion of a compound of formula A2 to a compound of formula A3, to yield a compound of formula B3.

The ester function of a compound of formula B3 may be reduced to its corresponding alcohol of formula B4. The alcohol of formula B4 may then be subjected to diazotization, followed by a Sandmeyer-type reaction as previously described in Scheme A, to obtain a compound of formula B5

(wherein $X^4$ is a halide, preferably chloro, bromo, or iodo). A compound of formula B5 may then be converted to a compound of formula B7 either by a direct coupling with a compound of formula D2, or via an activated intermediate of formula B6 (wherein $X^5$ is a leaving group, preferably chloro, bromo, or iodo). The G group may then be installed as previously described, utilizing substituent $X^4$ of a compound of formula B7 as a synthetic handle. Upon introduction of G, saponification of the ester to its corresponding acid affords a compound of formula (I).

One of ordinary skill in the art will recognize that the sequence of synthetic steps may be modified. For example, a G substituent may be introduced using a compound of formula B5, and the resulting product may then be converted to a compound of formula B8 via coupling to a compound of formula D2. The ester functionality of a compound of formula B8 may then be saponified using standard methods to furnish a compound of formula (I).

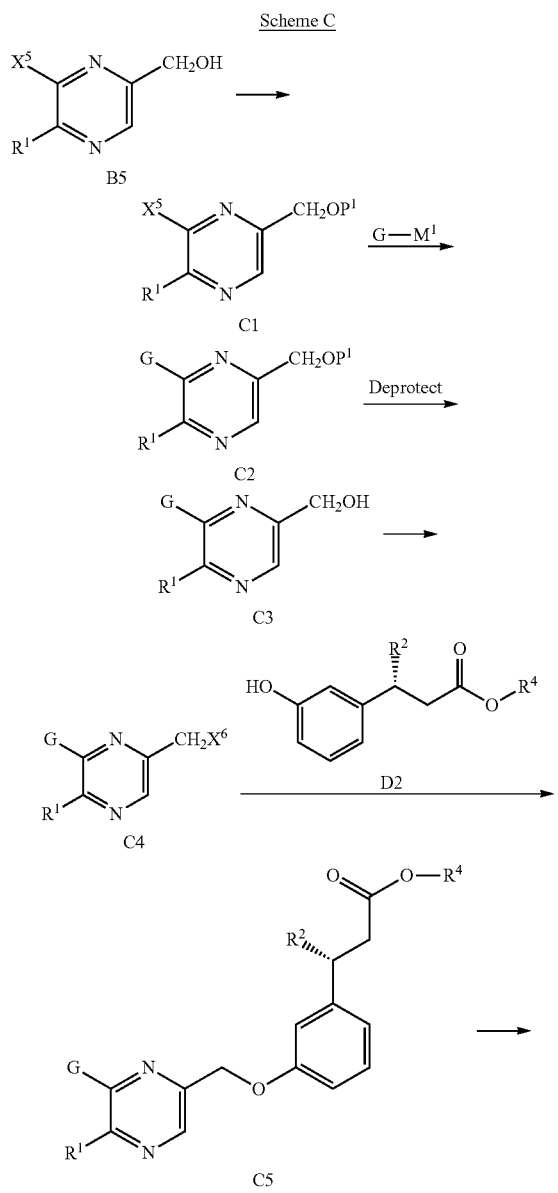

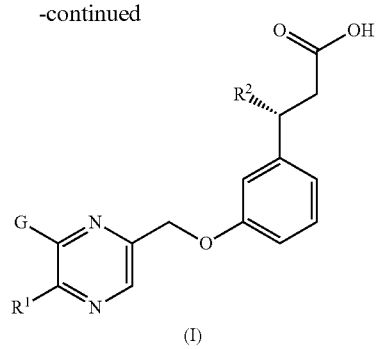

Scheme C is an alternative route to a compound of formula (I) via a protected alcohol of formula C1, wherein $P^1$ is a conventional alcohol protecting group. For example, the hydroxy group of a compound of formula B5 may be protected as a TBDMS-ether. The resulting product of formula C1 (wherein $X^5$ is chloro, bromo, or iodo) may be reacted with an organometallic reagent of formula G-$M^1$, such as G-ZnX, using standard Negishi coupling methodology to introduce substituent G. The protecting group $P^1$ may then be removed to unmask the hydroxy functional group of a compound of formula C3. For example, a TBDMS group may be removed using a fluoride source, or an acid such as TFA. The resulting compound of formula C3 may then be coupled with a compound of formula D2 either via an activated intermediate C4 wherein $X^6$ is a leaving group, or directly using Mitsunobu-type coupling methodology, as described for the conversion of a compound of formula B5 to B7 (Scheme B). Saponification via conventional methods yields a compound of formula (I).

Additionally, certain substituents of the present invention may contain functional groups which may be further elaborated at an appropriate later stage. For example, a compound of formula C5 wherein G is an alkenyl group, may be reduced to its corresponding alkyl group using a suitable reduction method such as a transition metal-catalyzed hydrogenation. Alternatively, an alkenyl functional group may be hydrolyzed to yield an alcohol or a diol using methods known to those of skill in the art.

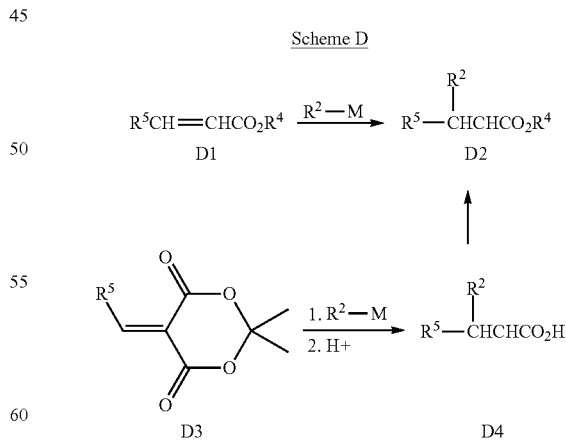

A compound of formula D2 may be prepared as shown in Scheme D. An acrylic ester of formula D1, wherein $R^5$ is 3-hydroxyphenyl, may be used as a substrate for a conjugate addition reaction with a compound of formula $R^2$-M, wherein M is a metal, to obtain a compound of formula D2.

The starting acrylate of formula D1 is either commercially available or may be prepared according to the methods described in the scientific literature. A compound of formula $R^2$-M may be (a) a boronic acid to form a compound of formula $R^2$—$B(OH)_2$; (b) a suitably selected boronic ester such as pinacolatoboryl, neopentylglycolatoboryl, and the like; (c) a suitably selected copper reagent or (d) a suitably selected Grignard reagent. One of ordinary skill in the art will understand that a catalyst, optionally in the presence of a ligand, may be required with the use of certain available reagents. In addition, with the use of certain other organometallic reagents, such as a Grignard reagent or an organo copper reagent, the free hydroxyl group may need to be protected with an appropriate hydroxyl protecting group, which may be removed at a later stage in the synthetic sequence. A preferred method for this transformation includes treatment of a compound of formula D1 with a compound of $R^2$-M wherein M is a boronic acid; in the presence of an Rh catalyst; with a suitable ligand such as BINAP. When optically pure BINAP is employed, an enantiomerically enriched compound of formula D2 may be prepared. A compound of formula D2 may be subjected to chiral separation to obtain an optically pure enantiomer. When a compound of formula D3 is employed in place of the acrylate starting material of formula D1, it is necessary to esterify the resultant carboxylic acid of formula D4 to obtain the desired compound of formula D2. One of ordinary skill in the art will recognize that in certain instances, substituent $R^5$ may be interchanged with substituent $R^2$.

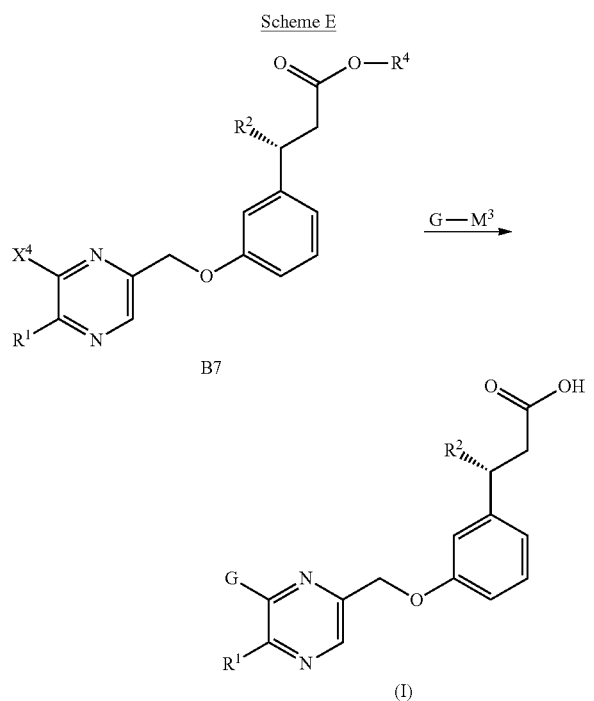

Scheme E illustrates the preparation of compounds of the present invention wherein substituent G connects to the pyrazine core of formula (I) via a heteroatom. A compound of formula B7 may be reacted with a metal alkoxide of formula G-$M^3$ to obtain a compound of formula (I). A preferred method for this transformation includes, but is not limited to, the reaction of a metal alkoxide such as sodium alkoxide; in a suitable solvent such as the parent alcohol of the alkoxide, THF, or DMF; at a temperature of about room temperature to about 200° C. For example, a compound of formula B7 may be treated with sodium isopropoxide; in refluxing isopropyl alcohol; to obtain a compound of formula (I) wherein G is isopropyloxy. Similarly, a compound of formula B7 may be treated with an amine or an aminometal salt to introduce a G-substituent that is $C_{1-6}$alkylamino or di($C_{1-6}$)alkylamino, or a heterocyclyl wherein said heterocyclyl is attached to the core pyrazine ring via a nitrogen atom. More specifically, a compound of formula B7 may be reacted with piperidine; in a solvent such as DMF or the like; at a temperature of about room temperature to about 150° C.; to obtain, upon subsequent saponification, a compound of formula (I) wherein G is piperidin-1-yl. One of ordinary skill in the art will recognize that such reactions involving the formation of a C—O or C—N bond may also be carried out utilizing other conventional organometallic protocols.

SPECIFIC EXAMPLES

Example 1

(3S)-3-(3-(((6-(Cycloheptyloxy)-5-(2-fluoro-5-methoxyphenyl)pyrazin-2-yl)methoxy)phenyl)-3-cyclopropylpropanoic acid (Cpd. 27)

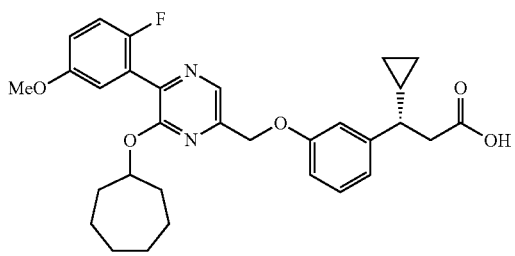 [SMILES: COc1ccc(F)c(-c2ncc(COc3cccc([C@@H](CC(=O)O)C4CC4)c3)nc2OC2CCCCCC2)c1]

A. 6-Bromo-3-(2-fluoro-5-methoxyphenyl)pyrazin-2-amine, 1a

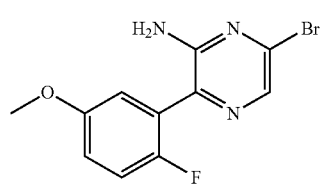

A mixture of 3,6-dibromopyrazin-2-amine (8.5 g, 34 mmol), (2-fluoro-5-methoxyphenyl)boronic acid (5.1 g, 30 mmol), $Pd(PPh_3)_4$ (3.1 g, 2.7 mmol), $Na_2CO_3$ (2M aqueous solution, 33 mL, 67 mmol), toluene (132 mL) and methanol (33 mL) was stirred for 72 h at 50° C. under $N_2$. The reaction mixture was allowed to cool to RT and treated with 500 mL of $H_2O$. The resulting mixture was extracted with EtOAc (3×500 mL). The organic layers were combined, dried ($Na_2SO_4$) and concentrated. The residue obtained was purified by flash chromatography on silica gel (EtOAc/petroleum ether 1:5-1:2 v/v) to obtain the title compound 1a. Mass Spectrum (LCMS, ESI pos.): Calcd. for $C_{11}H_9BrFN_3O$: 298.0 (M+H)$^+$; found: 298.0.

B. Methyl 6-amino-5-(2-fluoro-5-methoxyphenyl)pyrazine-2-carboxylate, 1b

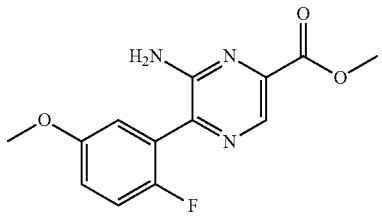

1b

6-Bromo-3-(2-fluoro-5-methoxyphenyl)pyrazin-2-amine (1a) (7.8 g, 26 mmol), Pd(dppf)Cl$_2$ (0.96 g, 1.3 mmol), triethylamine (5.3 g, 52 mmol) in methanol (150 mL) was stirred at 110° C. overnight under a 60 atm CO atmosphere. The resulting mixture was allowed to cool to RT, the vessel was depressurized, and the mixture was concentrated. The residue obtained was purified by column chromatography on silica gel, eluting with EtOAc/petroleum ether (1:3-1:1 v/v), to obtain the title compound 1b. Mass Spectrum (LCMS, ESI pos.): Calcd. for C$_{13}$H$_{12}$FN$_3$O$_3$: 278.1 (M+H)$^+$; found: 278.1.

C. (6-Amino-5-(2-fluoro-5-methoxyphenyl)pyrazin-2-yl)methanol, 1c

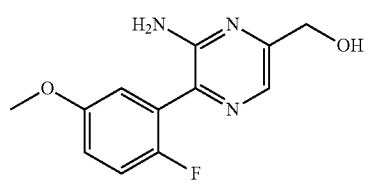

1c

To a solution of methyl 6-amino-5-(2-fluoro-5-methoxyphenyl)pyrazine-2-carboxylate (1b) (5.3 g, 19 mmol) in THF (100 mL), LiAlH$_4$ (2.2 g, 58 mmol) was added in several batches at 0° C. The resulting solution was stirred for 1 h at RT. The reaction was then quenched by the addition of 10% aq. NaOH solution (2.2 mL) and extracted with EtOAc (3×200 mL). The organic layers were combined, dried (Na$_2$SO$_4$) and concentrated. The residue obtained was purified by column chromatography on silica gel, eluting with EtOAc/petroleum ether (1:1-2:1 v/v) to obtain the title compound 1c. Mass Spectrum (LCMS, ESI pos.): Calcd. for C$_{12}$H$_{12}$FN$_3$O$_2$: 250.1 (M+H)$^+$; found: 250.1.

D. (6-Chloro-5-(2-fluoro-5-methoxyphenyl)pyrazin-2-yl)methanol, 1d

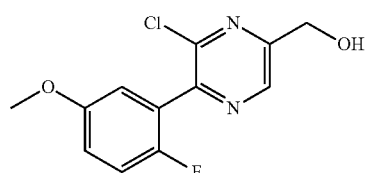

1d

A solution of [6-amino-5-(2-fluoro-5-methoxyphenyl)pyrazin-2-yl]methanol (1c) (3.1 g, 12 mmol), CuCl (2.5 g, 25 mmol), CuCl$_2$ (5.0 g, 37 mmol) in ACN (50 mL) was stirred for 10 min at RT and treated with 3-methylbutyl nitrite (7.2 g, 61 mmol) dropwise with stirring. The resulting solution was stirred overnight at RT. The reaction was then quenched by the addition of 200 mL of satd. NH$_4$Cl (aq) solution and extracted with EtOAc (3×200 mL). The organic layers were combined, dried (Na$_2$SO$_4$) and concentrated. The residue obtained was purified by column chromatography on silica gel, eluting with EtOAc/petroleum ether (1:2-1:1 v/v) to obtain the title compound. Mass Spectrum (LCMS, ESI pos.): Calcd. for C$_{12}$H$_{10}$ClFN$_2$O$_2$: 269.0 (M+H)$^+$; found: 269.1.

E. 3-Chloro-5-(chloromethyl)-2-(2-fluoro-5-methoxyphenyl)pyrazine, 1e

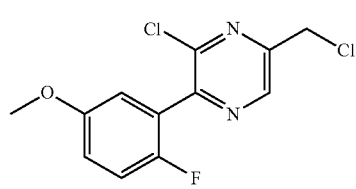

1e

To a solution of [6-chloro-5-(2-fluoro-5-methoxyphenyl)pyrazin-2-yl]methanol (1d) (1.32 g, 4.91 mmol) in dichloromethane (50 mL) and DMF (5 mL) was added thionyl chloride (1.17 g, 9.83 mmol) dropwise. The resulting solution was stirred for 30 min at 0° C. The reaction was then quenched by the addition of 100 mL of saturated NaHCO$_3$ (aq.) solution and extracted with dichloromethane (2×100 mL). The organic layers were combined, dried over anhydrous sodium sulfate and concentrated to obtain the title compound 1e.

F. (S)-Ethyl 3-cyclopropyl-3-(3-hydroxyphenyl)propanoate, 1f

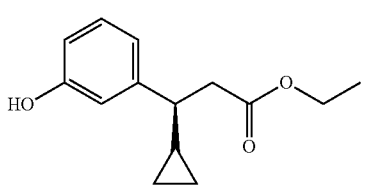

1f-(S)

I. Ethyl 3-cyclopropylacrylate, 1f-a

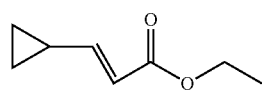

1f-a

To a solution of cyclopropanecarbaldehyde (20.4 g, 285 mmol) in THF (230 mL) at 0° C. under argon was added ethyl 2-(triphenylphosphoranylidene)acetate (107 g, 292 mmol) portion wise. The mixture was stirred at RT for 16 h, before the solvent was removed. The crude solid material obtained was suspended in heptane, sonicated and filtered. The filtrate was concentrated and purified by distillation under reduced pressure to afford compound 1f-a. $^1$H-NMR (400 MHz, CDCl$_3$) δ (ppm): 6.42 (dd, J=15.7, 10.1 Hz, 1H), 5.89 (d, J=15.7 Hz, 1H), 4.17 (q, J=7.1 Hz, 2H), 1.51-1.67 (m, 1H), 1.29 (t, J=7.1 Hz, 3H), 0.90-1.02 (m, 2H), 0.59-0.72 (m, 2H).

II. Ethyl 3-cyclopropyl-3-(3-hydroxyphenyl)propanoate, 1f-b

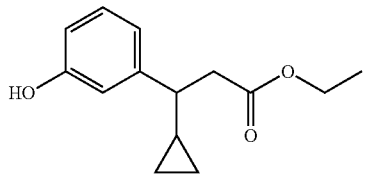

1f-b

To a mixture of chloro(1,5-cyclooctadiene)rhodium (I) dimer (1.79 g, 3.63 mmol) in 1,4-dioxane (50 mL) under argon was added 1 N aq. NaOH (109 mL, 109 mmol), (3-hydroxyphenyl)boronic acid (20.0 g, 145 mmol) and a solution of ethyl 3-cyclopropylacrylate (1f-a) (10.2 g, 72.5 mmol) in 1,4-dioxane (50 mL) at rt. The mixture obtained was stirred at 50° C. for 16 h. The reaction mixture was allowed to cool to RT, poured into 1:1 EtOAc/H$_2$O (100 mL), and was acidified with 2 N HCl (aq.) until the pH of the aqueous layer was ~4. The aqueous layer was extracted with EtOAc (2×50 mL). The combined organic layers were dried (Na$_2$SO$_4$) and filtered. After the removal of the solvents, the crude material was purified by flash column chromatography (0-30% EtOAc/heptane) to give the title compound 1f-b. $^1$H-NMR (400 MHz, CDCl$_3$) δ (ppm): 7.16 (t, J=7.8 Hz, 1H), 6.80 (d, J=8.1 Hz, 1H), 6.65-6.75 (m, 2H), 4.87 (s, 1H), 3.99-4.14 (m, 2H), 2.63-2.80 (m, 2H), 2.26-2.37 (m, 1H), 1.17 (t, J=7.1 Hz, 3H), 0.93-1.08 (m, 1H), 0.51-0.63 (m, 1H), 0.37-0.49 (m, 1H), 0.27 (dq, J=9.5, 4.9 Hz, 1H), 0.15 (dq, J=9.5, 4.9 Hz, 1H).

III. (S)-Ethyl 3-cyclopropyl-3-(3-hydroxyphenyl) propanoate, 1f-(S) and (R)-Ethyl 3-cyclopropyl-3-(3-hydroxyphenyl)propanoate, 1f-(R)

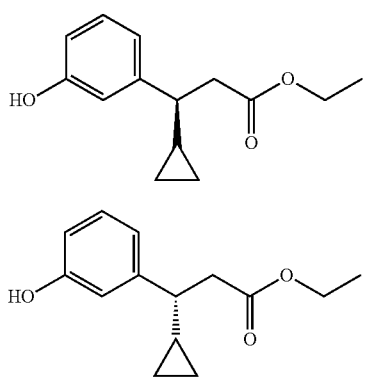

1f-(S)

1f-(R)

The racemic mixture of ethyl 3-cyclopropyl-3-(3-hydroxyphenyl)propanoate (1f-b) (29.4 g) was purified by chiral SFC (supercritical fluid chromatography) with 90% CO$_2$, 10% i-PrOH), yielding (S)-ethyl 3-cyclopropyl-3-(3-hydroxyphenyl)propanoate (1f-(S)) ([α]$_D^{20}$=+35.7) and (R)-ethyl 3-cyclopropyl-3-(3-hydroxyphenyl)propanoate (1f-(R)).

G. (3S)-Ethyl 3-(3-((6-chloro-5-(2-fluoro-5-methoxyphenyl)pyrazin-2-yl)methoxy)phenyl)-3-cyclopropylpropanoate, 1g

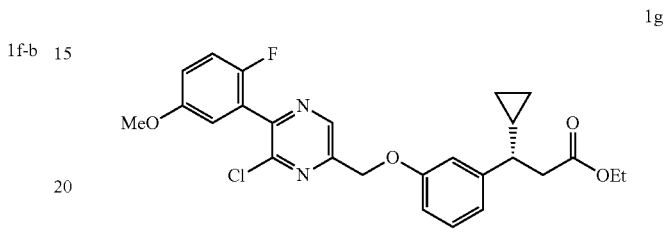

1g

A mixture of 3-chloro-5-(chloromethyl)-2-(2-fluoro-5-methoxyphenyl)pyrazine (1e) (1.4 g, 4.9 mmol), ethyl (3S)-3-cyclopropyl-3-(3-hydroxyphenyl)propanoate (1f-(S)) (1.2 g, 5.0 mmol) and Cs$_2$CO$_3$ (3.2 g, 9.8 mmol) in ACN (20 mL) was stirred for 2 h at 50° C. The reaction mixture was then quenched by the addition of 30 mL of water. The resulting solution was extracted with ethyl acetate (3×50 mL). The separated organic layers were combined, dried (Na$_2$SO$_4$) and concentrated. The resulting residue was purified by column chromatography on silica gel with EtOAc/petroleum ether (1:10-1:5 v/v) to obtain the title compound 1g. Mass Spectrum (LCMS, ESI pos.): Calcd. for C$_{26}$H$_{26}$ClFN$_2$O$_4$: 485.2 (M+H)$^+$; found: 485.2.

H. (3S)-3-(3-((6-(Cycloheptyloxy)-5-(2-fluoro-5-methoxyphenyl)pyrazin-2-yl)methoxy)phenyl)-3-cyclopropylpropanoic acid, Cpd 27

To a solution of cycloheptanol (340 mg, 2.98 mmol) in THF (2 mL), Na (69.0 mg, 3.00 mmol) was added. The resulting mixture was stirred at 75° C. overnight in a sealed tube. A solution of ethyl (3S)-3-(3-[[6-chloro-5-(2-fluoro-5-methoxyphenyl)pyrazin-2-yl]methoxy]phenyl)-3-cyclopropylpropanoate (1g) (140 mg, 0.30 mmol) in THF (1 mL) was then added and the resulting solution was stirred for 2 h at 75° C. The reaction mixture was allowed to cool to RT, treated dropwise with 2 mL of water, adjusted to pH 6 with 1M HCl, and extracted with EtOAc (3×10 mL). The organic layers were combined, dried (Na$_2$SO$_4$), and concentrated. The residue obtained was purified by reversed phase Prep-HPLC (water/CH$_3$CN as mobile phase) to obtain the title compound 27. $^1$H-NMR (300 MHz, DMSO-d$_6$) δ (ppm): 8.41 (s, 1H), 7.20-7.26 (m, 2H), 6.90-7.07 (s, 2H), 6.86-6.88 (m, 3H), 5.26-5.28 (m, 1H), 5.20 (s, 2H), 3.77 (s, 3H), 2.49-2.67 (m, 2H), 2.25-2.32 (m, 1H), 1.72-1.95 (m, 2H), 1.65-1.70 (m, 2H), 1.41-1.55 (m, 8H), 0.89-1.01 (m, 1H), 0.47-0.50 (m, 1H), 0.21-0.30 (m, 2H), 0.09-0.10 (m, 1H). Mass Spectrum (LCMS, ESI pos.): Calcd. for C$_{31}$H$_{35}$FN$_2$O$_5$: 535.3 (M+H)$^+$; found: 535.4.

Example 2

(3S)-3-Cyclopropyl-3-(3-((5-(5-fluoro-2-methoxy-pyridin-4-yl)-6-(5-methylthiophen-2-yl)pyrazin-2-yl)methoxy)phenyl)propanoic acid (Cpd. 28)

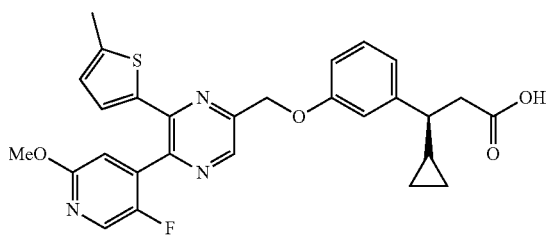 [SMILES: COc1cc(-c2ncc(COc3cccc([C@@H](CC(=O)O)C4CC4)c3)nc2-c2ccc(C)s2)c(F)cn1]

A. 6-Chloro-3-(5-fluoro-2-methoxypyridin-4-yl)pyrazin-2-amine, 2a

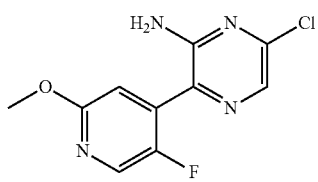

A mixture of 3-bromo-6-chloropyrazin-2-amine (14.0 g, 67.2 mmol), (5-fluoro-2-methoxypyridin-4-yl)boronic acid (14.8 g, 86.6 mmol), Pd(dppf)Cl$_2$ (3.90 g, 5.33 mmol), Cs$_2$CO$_3$ (54.5 g, 167 mmol) in water (50 mL) and 1,4-dioxane (200 mL) was stirred for 1 h at 90° C. under N$_2$. The reaction mixture was allowed to cool to RT, then treated with 200 mL of H$_2$O, and extracted with EtOAc (3×300 mL). The combined organic layers were dried (Na$_2$SO$_4$) and concentrated. The residue obtained was purified by flash column chromatography on silica gel (EtOAc/petroleum ether 1:2-1:1 v/v) to obtain the title compound 2a. Mass Spectrum (LCMS, ESI pos.): Calcd. for C$_{10}$H$_8$ClFN$_4$O: 255.0 (M+H)$^+$; found: 255.0.

B. Methyl 6-amino-5-(5-fluoro-2-methoxypyridin-4-yl)pyrazine-2-carboxylate, 2b

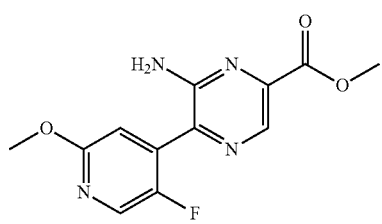

A mixture of 6-chloro-3-(5-fluoro-2-methoxypyridin-4-yl)pyrazin-2-amine (2a) (11 g, 44 mmol), Pd(dppf)Cl$_2$ (2.7 g, 3.7 mmol), triethylamine (9.5 g, 94 mmol) in methanol (200 mL) was stirred overnight at 110° C. under a 60 atm CO atmosphere. The reaction mixture was allowed to cool to RT, the reaction vessel was depressurized, and the reaction mixture was concentrated. The resulting residue was purified by column chromatography on silica gel eluting with EtOAc/petroleum ether (1:1 v/v) to obtain the title compound 2b. Mass Spectrum (LCMS, ESI pos.): Calcd. for C$_{12}$H$_{11}$FN$_4$O$_3$: 279.1 (M+H)$^+$; found: 279.1.

C. (6-Amino-5-(5-fluoro-2-methoxypyridin-4-yl)pyrazin-2-yl)methanol, 2c

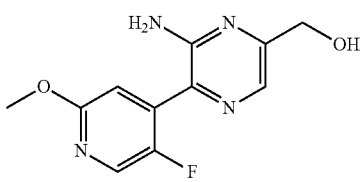

To a solution of methyl 6-amino-5-(5-fluoro-2-methoxypyridin-4-yl)pyrazine-2-carboxylate, 2b (10.5 g, 37.7 mmol) in THF (200 mL) was added LiAlH$_4$ (1.77 g, 46.6 mmol) portion-wise with stirring at 0° C. The resulting solution was stirred for 1 h at 0° C. and the reaction was quenched by the addition of 2 mL of water. The resulting mixture was concentrated. The residue obtained was purified by flash column chromatography (DCM/methanol 10:1 v/v) to obtain the title compound 2c. Mass Spectrum (LCMS, ESI pos.): Calcd. for C$_{11}$H$_{11}$FN$_4$O$_2$: 251.1 (M+H)$^+$; found: 251.1.

D. (6-Chloro-5-(5-fluoro-2-methoxypyridin-4-yl)pyrazin-2-yl)methanol, 2d

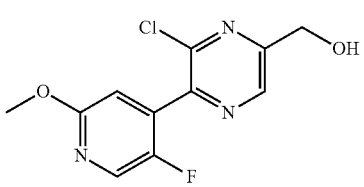

A mixture of (6-amino-5-(5-fluoro-2-methoxypyridin-4-yl)pyrazin-2-yl)methanol (2d) (3.0 g, 12 mmol), CuCl (2.4 g, 24 mmol) and CuCl$_2$ (4.8 g, 36 mmol) in ACN (150 mL) was stirred for 30 min. To the mixture was added isopentyl nitrite (8.2 g, 70 mmol). The resulting solution was stirred overnight at room temperature and treated with 150 mL of satd. NH$_4$Cl (aq.) solution. The resulting mixture was extracted with EtOAc (3×200 mL). The combined organic layers were dried (Na$_2$SO$_4$) and concentrated. The residue obtained was purified by flash column chromatography on silica gel (EtOAc/petroleum ether 1:3 v/v) to obtain the title compound 2d. Mass Spectrum (LCMS, ESI pos.): Calcd. for C$_{11}$H$_9$ClFN$_3$O$_2$: 270.0 (M+H)$^+$; found: 270.0.

E. 3-Chloro-5-(chloromethyl)-2-(5-fluoro-2-methoxypyridin-4-yl)pyrazine, 2e

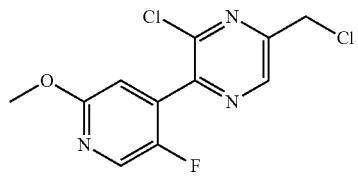

2e

To a stirred solution of [6-chloro-5-(5-fluoro-2-methoxypyridin-4-yl)pyrazin-2-yl]methanol (2d) (1.2 g, 4.4 mmol) and DMF (2 mL) in dichloromethane (20 mL) was added $SOCl_2$ (1.1 g, 8.9 mmol) dropwise. The resulting solution was stirred for 1 h at 0° C., treated with 5 mL of saturated $NaHCO_3$ (aq) solution, and extracted with dichloromethane (20 mL). The combined DCM layers were dried ($Na_2SO_4$) and filtered. The filtrate was concentrated to obtain the title compound 2e.

F. (3S)-Methyl 3-(3-((6-Chloro-5-(5-fluoro-2-methoxypyridin-4-yl)pyrazin-2-yl)methoxy)phenyl)-3-cyclopropylpropanoate, 2f

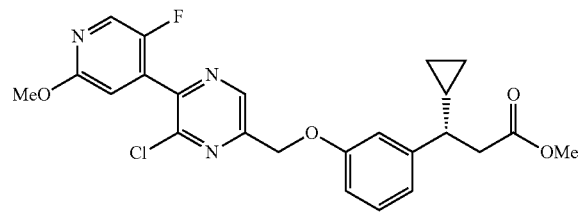

2f

A mixture of 3-chloro-5-(chloromethyl)-2-(5-fluoro-2-methoxypyridin-4-yl)pyrazine (2e) (1.20 g, 4.17 mmol), methyl (3S)-3-cyclopropyl-3-(3-hydroxyphenyl)propanoate (2f-1) (920 mg, 4.18 mmol, commercially available, cat. # PB05716, Synnovator, Inc.) and $Cs_2CO_3$ (2.74 g, 8.41 mmol) in ACN (20 mL) was stirred overnight at room temperature. The reaction mixture was then quenched by the addition of 20 mL of water. The resulting mixture was extracted with EtOAc (3×50 mL). The organic layers were combined, dried ($Na_2SO_4$) and concentrated. The residue obtained was purified by flash column chromatography on silica gel (EtOAc/petroleum ether 1:9 v/v) to obtain the title compound 2f. $^1$H-NMR (400 MHz, $CDCl_3$) δ (ppm): 8.87 (s, 1H), 8.14 (s, 1H), 7.26-7.30 (m, 1H), 7.16-7.24 (m, 1H), 6.72-6.92 (m, 4H), 5.28 (s, 2H), 4.09-4.16 (m, 1H), 3.97 (s, 2H), 3.61 (s, 3H), 2.71-2.77 (m, 2H), 2.35-2.38 (m, 1H), 2.05 (s, 1H), 1.24-1.28 (m, 1H), 1.00-1.04 (m, 1H), 0.57-0.61 (m, 1H), 0.42-0.46 (m, 1H), 0.23-0.29 (m, 1H), 0.12-0.19 (m, 1H). Mass Spectrum (LCMS, ESI pos.): Calcd. for $C_{24}H_{23}ClFN_3O_4$: 472.1 (M+H)$^+$; found: 472.1.

G. (3S)-Methyl 3-cyclopropyl-3-(3-((5-(5-fluoro-2-methoxypyridin-4-yl)-6-(5-methylthiophen-2-yl)pyrazin-2-yl)methoxy)phenyl)propanoate, 2g

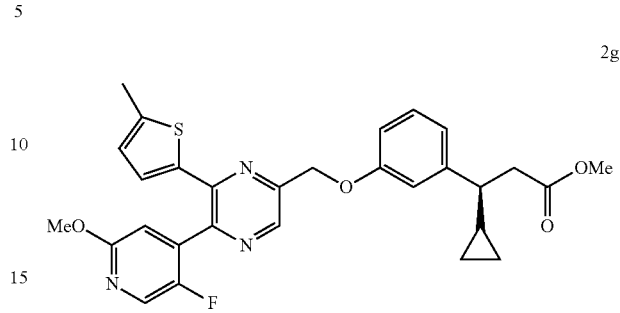

2g

A mixture of (3S)-methyl 3-(3-((6-chloro-5-(5-fluoro-2-methoxypyridin-4-yl)pyrazin-2-yl)methoxy)phenyl)-3-cyclopropylpropanoate (2f) (100 mg, 0.210 mmol), (5-methylthiophen-2-yl)boronic acid (45 mg, 0.32 mmol), Pd(dppf)$Cl_2$ (7.8 mg, 0.010 mmol) and $Cs_2CO_3$ (173 mg, 0.530 mmol) in 1,4-dioxane (8 mL) and water (2 mL) was stirred for 2 h hour at 80° C. under $N_2$. The reaction mixture was allowed to cool to RT and concentrated. The residue obtained was purified by flash column chromatography on silica gel (EtOAc/petroleum ether 1:10-1:5 v/v) to obtain the title compound 2g. Mass Spectrum (LCMS, ESI pos.): Calcd. for $C_{29}H_{28}FN_3O_4S$: 534.2 (M+H)$^+$; found: 534.1.

H. (3S)-3-Cyclopropyl-3-(3-((5-(5-fluoro-2-methoxypyridin-4-yl)-6-(5-methylthiophen-2-yl)pyrazin-2-yl)methoxy)phenyl)propanoic acid, Cpd 28

A mixture of (3S)-methyl 3-cyclopropyl-3-(3-((5-(5-fluoro-2-methoxypyridin-4-yl)-6-(5-methylthiophen-2-yl)pyrazin-2-yl)methoxy)phenyl)propanoate (2g) (78 mg, 0.15 mmol), LiOH (38 mg, 1.6 mmol), THF (4 mL), water (2 mL), and methanol (1 mL) was stirred overnight at RT. The resulting mixture was concentrated. The pH value of the resulting solution was then adjusted to 4-5 with 1 N HCl. The solids formed were collected by filtration to give the title compound 28. $^1$H-NMR (300 MHz, DMSO-$d_6$) δ (ppm): 11.90-12.05 (br, 1H), 8.77 (s, 1H), 8.28 (s, 1H), 7.24 (t, J=7.8 Hz, 1H), 7.15 (d, J=4.8 Hz, 1H), 7.03 (s, 1H), 6.88-6.96 (m, 2H), 6.70-6.74 (m, 2H), 5.32 (s, 2H), 3.91 (s, 3H), 2.62-2.65 (m, 2H), 2.57 (s, 3H), 2.24-2.33 (m, 1H), 0.99-1.03 (m, 1H), 0.49-0.51 (m, 1H), 0.20-0.32 (m, 2H), 0.09-0.15 (m, 1H). Mass Spectrum (LCMS, ESI pos.): Calcd. for $C_{28}H_{26}FN_3O_4S$: 520.2 (M+H)$^+$; found: 520.1.

Example 3

(3S)-3-Cyclopropyl-3-(3-((5-(5-fluoro-2-methoxypyridin-4-yl)-6-isobutoxypyrazin-2-yl)methoxy)phenyl)propanoic acid (Cpd. 12)

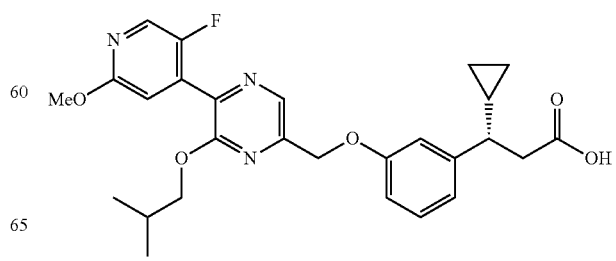

To a solution 2-methylpropan-1-ol (50 mg, 0.67 mmol), in THF (10 mL) was added 60% sodium hydride in mineral oil (35 mg, 0.88 mmol) at 0° C. The resulting mixture was stirred for 10 min at RT and (3S)-methyl 3-(3-((6-chloro-5-(5-fluoro-2-methoxypyridin-4-yl)pyrazin-2-yl)methoxy)phenyl)-3-cyclopropylpropanoate (20 (100 mg, 0.21 mmol) was added. The resulting mixture was heated at reflux overnight. The reaction mixture was allowed to cool to RT and treated with 1 N HCl (0.5 mL) and concentrated. The residue obtained was purified by flash column chromatography on silica gel (EtOAc/petroleum ether 1:1-2:1 v/v) to obtain the title compound 12. $^1$H-NMR (300 MHz, DMSO-$d_6$) δ (ppm): 8.48 (s, 1H), 8.28 (s, 1H), 7.21 (t, J=7.8 Hz, 1H), 7.03 (d, J=4.5 Hz, 1H), 6.87-6.94 (m, 3H), 5.22 (s, 2H), 4.14 (d, J=6.3 Hz, 1H), 3.89 (s, 3H), 2.52-2.55 (m, 2H), 2.43-2.47 (m, 1H), 1.95-1.97 (m, 1H), 0.88-0.90 (m, 7H), 0.44-0.46 (m, 1H), 0.23-0.27 (m, 2H), 0.01-0.10 (m, 1H). Mass Spectrum (LCMS, ESI pos.): Calcd. for $C_{27}H_{30}FN_3O_5$: 496.2 (M+H)$^+$; found: 496.2.

Example 4

(3S)-3-Cyclopropyl-3-(3-((5-(2-fluoro-5-methoxyphenyl)-6-(4-isopropylphenyl)pyrazin-2-yl)methoxy)phenyl)propanoic acid (Cpd. 25)

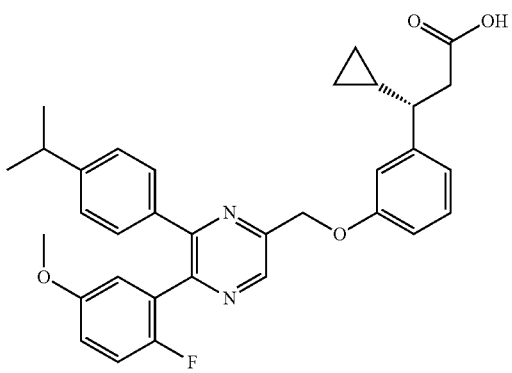 [SMILES: COc1ccc(F)c(-c2ncc(COc3cccc([C@@H](CC(=O)O)C4CC4)c3)nc2-c2ccc(C(C)C)cc2)c1]

A. Methyl (3S)-3-(3-[[6-chloro-5-(2-fluoro-5-methoxyphenyl)pyrazin-2-yl]methoxy]phenyl)-3-cyclopropylpropanoate, 4a

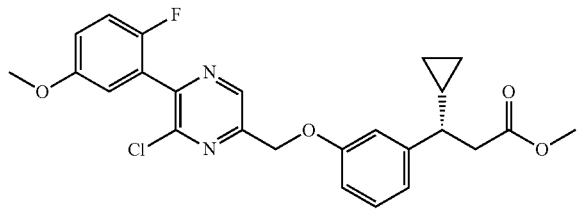

The title compound 4a was prepared according to the methods described in Example 1, substituting methyl 3-cyclopropylacrylate for ethyl 3-cyclopropylacrylate in Step F. Mass Spectrum (LCMS, ESI pos.): Calcd. for $C_{25}H_{24}ClFN_2O_4$: 471.1 (M+H)$^+$; found: 471.1, 473.1.

B. (3S)-Methyl 3-cyclopropyl-3-(3-((5-(2-fluoro-5-methoxyphenyl)-6-(4-isopropylphenyl)pyrazin-2-yl)methoxy)phenyl)propanoate, 4b

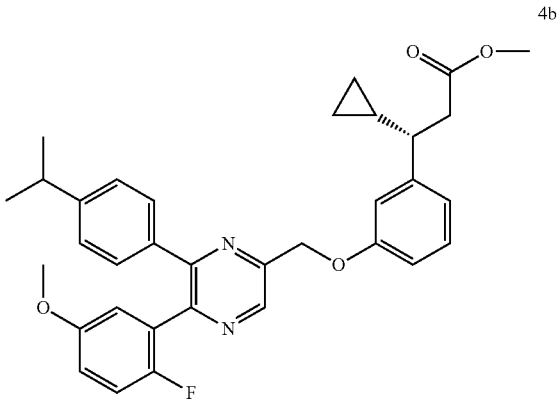 [SMILES: COC(=O)C[C@H](c1cccc(OCc2cnc(-c3cc(OC)ccc3F)c(-c3ccc(C(C)C)cc3)n2)c1)C1CC1]

A mixture of methyl (3S)-3-(3-[[6-chloro-5-(2-fluoro-5-methoxyphenyl)pyrazin-2-yl]methoxy]phenyl)-3-cyclopropylpropanoate (4a) (80 mg, 0.17 mmol), water (0.2 mL), [4-(propan-2-yl)phenyl]boronic acid (56 mg, 0.34 mmol), Pd(dppf)Cl$_2$ (12 mg, 0.020 mmol) and Cs$_2$CO$_3$ (138 mg, 0.420 mmol) in dioxane (0.8 mL) was stirred for 2 h at 95° C. under N$_2$. The reaction mixture was allowed to cool to RT. treated with 10 mL of water, and extracted with EtOAc (3×10 mL). The combined organic layers were dried (Na$_2$SO$_4$), filtered, and concentrated. The residue obtained was purified by column chromatography on silica gel (EtOAc/petroleum ether, 1:100-1:20 v/v) to give the title compound 4a. Mass Spectrum (LCMS, ESI pos.): Calcd. for $C_{34}H_{35}FN_2O_4$: 555.3 (M+H)$^+$; found: 555.1.

C. (3S)-3-Cyclopropyl-3-(3-((5-(2-fluoro-5-methoxyphenyl)-6-(4-isopropylphenyl)pyrazin-2-yl)methoxy)phenyl)propanoic acid, Cpd. 25

A mixture of (3S)-methyl 3-cyclopropyl-3-(3-((5-(2-fluoro-5-methoxyphenyl)-6-(4-isopropylphenyl)pyrazin-2-yl)methoxy)phenyl)propanoate (4b) (70 mg, 0.13 mmol), LiOH.H$_2$O (53 mg, 1.3 mmol) in THF (4 mL), methanol (1 mL) and water (1 mL) was stirred overnight at RT. The resulting mixture was concentrated to remove most of the organic solvents and diluted with 4 mL of water. The pH of the solution was adjusted to 4-5 with 2 N HCl. The formed solids were collected by filtration to give the title compound 25. $^1$H-NMR (300 MHz, DMSO-$d_6$) δ (ppm): 12.15 (brs, 1H), 8.86 (s, 1H), 7.35-7.38 (m, 2H), 7.14-7.26 (m, 3H), 6.87-7.13 (m, 6H), 5.35 (s, 2H), 3.74 (s, 3H), 2.81-2.95 (m, 1H), 2.59-2.73 (m, 2H), 2.19-2.32 (m, 1H), 1.18 (d, J=6.9 Hz, 6H), 0.90-1.05 (m, 1H), 0.44-0.54 (m, 1H), 0.21-0.40 (m, 2H), 0.02-0.18 (m, 1H). Mass Spectrum (LCMS, ESI pos.): Calcd. for $C_{33}H_{33}FN_2O_4$: 541.2 (M+H)$^+$; found: 541.2.

Example 5

(3S)-3-Cyclopropyl-3-(3-((5-(2-fluoro-5-methoxyphenyl)-6-(3,3,5,5-tetramethylcyclohexyloxy)pyrazin-2-yl)methoxy)phenyl)propanoic acid (Cpd. 24)

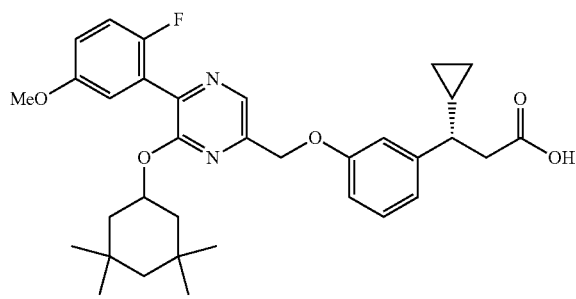 [SMILES: COc1ccc(F)c(-c2ncc(COc3cccc([C@@H](CC(=O)O)C4CC4)c3)nc2OC2CC(C)(C)CC(C)(C)C2)c1]

A. 3,3,5,5-Tetramethylcyclohexanol, 5a

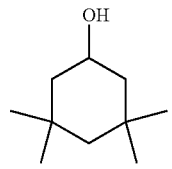

To a solution of 3,3,5,5-tetramethylcyclohexan-1-one (1.00 g, 6.48 mmol), in THF (10 mL) was added NaBH$_4$ (497 mg, 13.1 mmol) in portions followed by methanol (10 mL). The resulting solution was stirred for 2 h at RT and then treated with water (15 mL). The resulting solution was extracted with of EtOAc (3×10 mL). The combined organic layers were dried (Na$_2$SO$_4$) and concentrated. The residue obtained was purified by column chromatography on silica gel (EtOAc/petroleum (1:5 v/v)) to give the title compound 5a. $^1$H-NMR (300 MHz, CDCl$_3$) δ (ppm): 3.88-3.97 (m, 1H), 1.71-1.77 (m, 2H), 1.36-1.37 (m, 1H), 1.20-1.25 (m, 1H), 0.97-1.05 (m, 8H), 0.89-0.95 (m, 6H).

B. Sodium 3,3,5,5-tetramethylcyclohexanolate, 5b

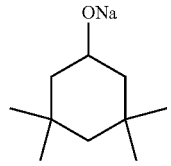

To a solution of 3,3,5,5-tetramethylcyclohexan-1-ol (5a) (100 mg, 0.640 mmol) in THF (2 mL) was added Na (15.0 mg, 0.650 mmol). The resulting solution was stirred overnight at 100° C., allowed to cool to RT and used in the next step directly.

C. (3S)-3-Cyclopropyl-3-(3-((5-(2-fluoro-5-methoxyphenyl)-6-(3,3,5,5-tetramethylcyclohexyloxy)pyrazin-2-yl)methoxy)phenyl)propanoic acid, Cpd 24

To a solution of methyl (3S)-3-(3-[[6-chloro-5-(2-fluoro-5-methoxyphenyl)pyrazin-2-yl]methoxy]phenyl)-3-cyclopropylpropanoate (4a) (96 mg, 0.20 mmol) in THF (2 mL), was added sodium 3,3,5,5-tetramethylcyclohexanolate (5b) in THF (0.5 mL). The resulting solution was stirred overnight at 75° C. and allowed to cool to RT. The pH of the solution was adjusted to ~4 with 0.5 N HCl. The resulting mixture was concentrated. The residue obtained was purified by column chromatography on silica gel (EtOAc/petroleum ether (1:1 v/v)) to give the title compound 24. $^1$H-NMR (300 MHz, DMSO-d$_6$) δ (ppm): 8.42 (s, 1H), 7.18-7.26 (m, 2H), 7.02-7.05 (m, 2H), 6.85-6.93 (m, 3H), 5.35-5.42 (m, 1H), 5.21 (s, 2H), 3.77 (s, 3H), 2.50-2.63 (m, 2H), 2.25-2.28 (m, 1H), 1.80-1.83 (m, 2H), 1.21-1.26 (m, 5H), 1.05 (s, 6H), 0.89 (s, 6H), 0.40-0.56 (m, 1H), 0.20-0.40 (m, 2H), 0.02-0.11 (m, 1H). Mass Spectrum (LCMS, ESI pos.): Calcd. for C$_{34}$H$_{41}$FN$_2$O$_5$: 577.3 (M+H)$^+$; found: 577.3.

Example 6

(3S)-3-Cyclopropyl-3-(3-((6-(3,5-dimethylphenyl)-5-(2-fluoro-5-methoxyphenyl)pyrazin-2-yl)methoxy)phenyl)propanoic acid (Cpd. 10)

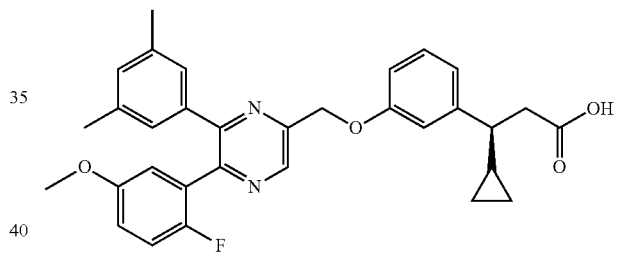

A. (3S)-Methyl 3-cyclopropyl-3-(3-((6-(3,5-dimethylphenyl)-5-(2-fluoro-5-methoxyphenyl)pyrazin-2-yl)methoxy)phenyl)propanoate, 6a

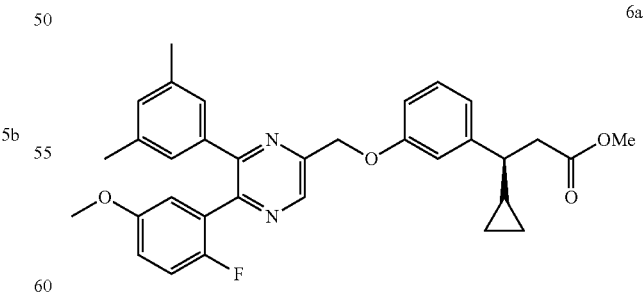

A mixture of methyl (3S)-3-(3-[[6-chloro-5-(2-fluoro-5-methoxyphenyl)pyrazin-2-yl]methoxy]phenyl)-3-cyclopropylpropanoate (4a) (80 mg, 0.17 mmol), (3,5-dimethylphenyl)boronic acid (31 mg, 0.21 mmol), Pd(dppf)Cl$_2$ (6.2 mg, 0.01 mmol) and Cs$_2$CO$_3$ (139 mg, 0.43 mmol) in 1,4-dioxane (1.6 mL) and water (0.4 mL) was stirred for 1 h at 80° C. under N₂. The resulting mixture was allowed to cool to RT and concentrated. The residue obtained was purified on silica gel eluting with EtOAc/petroleum ether (1:10-1:2 v/v) to give the title compound. Mass Spectrum (LCMS, ESI pos.): Calcd. for $C_{33}H_{33}FN_2O_4$: 541.2 (M+H)⁺; found: 541.2.

B. (3S)-3-Cyclopropyl-3-(3-((6-(3,5-dimethylphenyl)-5-(2-fluoro-5-methoxyphenyl)pyrazin-2-yl)methoxy)phenyl)propanoic acid, Cpd. 10

The title compound was prepared from compound 6a following the procedure described in Example 2, Step H. ¹H-NMR (300 MHz, DMSO-d₆) δ (ppm): 8.87 (s, 1H), 7.23 (t, J=7.8 Hz, 1H), 7.12-7.14 (m, 1H), 6.95-7.05 (m, 6H), 6.87-6.92 (m, 2H), 5.35 (s, 2H), 3.75 (s, 3H), 2.59-2.62 (m, 2H), 2.27-2.30 (m, 1H), 2.16 (s, 6H), 0.91-1.05 (m, 1H), 0.45-0.48 (m, 1H), 0.21-0.29 (m, 2H), 0.08-0.10 (m, 1H). Mass Spectrum (LCMS, ESI pos.): Calcd. for $C_{32}H_{31}FN_2O_4$: 527.2 (M+H)⁺; found: 527.1.

Example 7

(3S)-3-Cyclopropyl-3-(3-((6-cyclopropyl-5-(2-fluoro-5-methoxyphenyl)pyrazin-2-yl)methoxy)phenyl)propanoic acid (Cpd. 39)

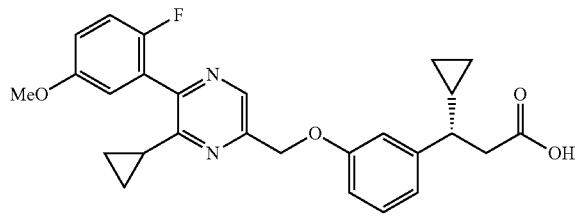 [SMILES: COc1ccc(F)c(-c2ncc(COc3cccc([C@@H](CC(=O)O)C4CC4)c3)nc2C2CC2)c1]

The title compound was prepared from compound 1g and cyclopropyl boronic acid following the procedure described in Example 2, Steps G-H. ¹H-NMR (300 MHz, DMSO-d₆) δ (ppm): 12.00 (br, 1H), 8.63 (s, 1H), 7.19-7.34 (m, 2H), 6.97-7.13 (m, 2H), 6.92 (s, 1H), 6.86-6.91 (m, 2H), 5.21 (s, 2H), 3.79 (s, 3H), 2.64-2.91 (m, 2H), 2.25-2.30 (m, 1H), 1.89-1.93 (m, 1H), 0.98-1.04 (m, 5H), 0.48-0.51 (m, 1H), 0.22-0.32 (m, 2H), 0.08-0.12 (m, 1H). Mass Spectrum (LCMS, ESI pos.): Calcd. for $C_{27}H_{27}FN_2O_4$: 463.2 (M+H)⁺; found: 463.2.

Example 8

(3S)-3-Cyclopropyl-3-(3-((5-(2-fluoro-5-methoxyphenyl)-6-(3,3,3-trifluoropropoxy)pyrazin-2-yl)methoxy)phenyl)propanoic acid (Cpd. 32)

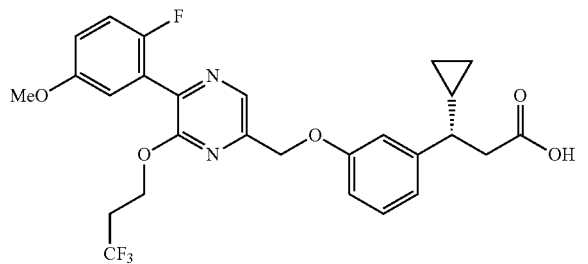 [SMILES: COc1ccc(F)c(-c2ncc(COc3cccc([C@@H](CC(=O)O)C4CC4)c3)nc2OCCC(F)(F)F)c1]

The title compound was prepared from compound 1g and 3,3,3-trifluoropropan-1-ol following an adaptation of the procedure described in Example 3 treating the alcohol with NaH at RT for 30 min and heating at 75° C. for 1 h rather than treating the alcohol with NaH at 0° C. for 10 min. and refluxing overnight. ¹H-NMR (300 MHz, DMSO-d₆) δ (ppm): 8.52 (s, 1H), 7.20-7.26 (m, 2H), 7.04-7.19 (m, 2H), 6.93 (s, 1H), 6.86-6.90 (m, 2H), 5.23 (s, 2H), 4.55 (t, J=5.7 Hz, 2H), 3.76 (s, 3H), 2.69-2.81 (m, 2H), 2.56-2.61 (m, 2H), 2.24-2.32 (m, 1H), 0.97-1.03 (m, 1H), 0.44-0.49 (m, 1H), 0.22-0.29 (m, 2H), 0.01-0.10 (m, 1H). Mass Spectrum (LCMS, ESI pos.): Calcd. for $C_{27}H_{26}F_4N_2O_5$: 535.2 (M+H)⁺; found: 535.2.

Example 9

(3S)-3-Cyclopropyl-3-(3-((5-(2-fluoro-5-methoxyphenyl)-6-((2,2,3,3-tetramethylcyclopropyl)methoxy)pyrazin-2-yl)methoxy)phenyl)propanoic acid (Cpd. 17)

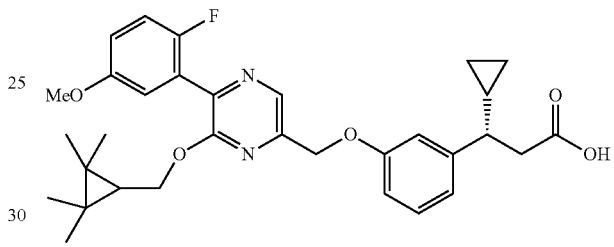

A. (2,2,3,3-Tetramethylcyclopropyl)methanol, 9a

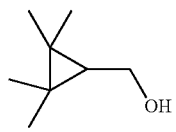

9a

To a solution of tetramethylcyclopropane-1-carboxylic acid (1.0 g, 7.0 mmol) in THF (10 mL) was added BH₃ (1 N in THF, 28 mL, 28.0 mmol) dropwise with stirring at 0° C. The resulting solution was stirred for 3 h at 0° C. The reaction was then quenched by the addition of 1 mL of methanol. The resulting mixture was concentrated. The residue obtained was purified by column chromatography on silica gel (EtOAc/petroleum ether (1:5 v/v)) to obtain the title compound 9a. ¹H-NMR (300 MHz, CDCl₃) δ (ppm): 3.75-3.89 (m, 2H), 1.07-1.09 (m, 6H), 0.95-1.00 (m, 6H), 0.53-0.58 (m, 1H).

B. (3S)-3-Cyclopropyl-3-(3-((5-(2-fluoro-5-methoxyphenyl)-6-((2,2,3,3-tetramethylcyclopropyl)methoxy)pyrazin-2-yl)methoxy)phenyl)propanoic acid, Cpd 17

The title compound 17 was prepared from compound 1g and compound 9a following an adaptation of the procedure described in Example 3, refluxing for 2 h rather than overnight. ¹H-NMR (300 MHz, DMSO-d₆) δ (ppm): 8.44 (s, 1H), 7.19-7.28 (m, 2H), 7.04-7.07 (m, 2H), 6.98 (s, 1H), 6.86-6.93 (m, 2H), 5.21 (s, 2H), 4.39 (d, J=7.8 Hz, 2H), 3.78

(s, 3H), 2.61-2.64 (m, 2H), 2.23-2.28 (m, 1H), 0.98-1.02 (m, 13H), 0.63-0.69 (m, 1H), 0.45-0.51 (m, 1H), 0.23-0.29 (m, 2H), 0.09-0.11 (m, 1H). Mass Spectrum (LCMS, ESI pos.): Calcd. for $C_{32}H_{37}FN_2O_5$: 549.3 (M+H)$^+$; found: 549.3.

Example 10

(3S)-3-Cyclopropyl-3-(3-((5-(2-fluoro-5-methoxyphenyl)-6-(2,2,6,6-tetramethyl-tetrahydro-2H-pyran-4-yloxy)pyrazin-2-yl)methoxy)phenyl)propanoic acid (Cpd. 26)

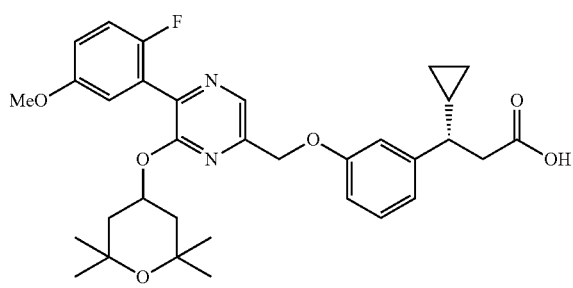 [SMILES: COc1ccc(F)c(-c2ncc(COc3cccc([C@@H](CC(=O)O)C4CC4)c3)nc2OC2CC(C)(C)OC(C)(C)C2)c1]

A. 2,2,6,6-Tetramethyl-tetrahydro-2H-pyran-4-ol, 10a

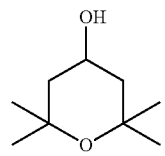

10a

A solution of 2,2,6,6-tetramethyloxan-4-one (190 mg, 1.22 mmol) and NaBH$_4$ (93 mg, 2.5 mmol) in THF (4 mL) and methanol (2 mL) was stirred for 1 h at RT. The reaction was then quenched by the addition of 0.1 mL of water. The resulting mixture was concentrated. The residue obtained was purified by column chromatography on silica gel (EtOAc/petroleum ether (1:5-1:3 v/v)) to give the compound 10a. $^1$H-NMR (300 MHz, CDCl$_3$) δ (ppm): 3.88-3.97 (m, 1H), 1.71-1.77 (m, 2H), 1.36-1.37 (m, 1H), 1.20-1.25 (m, 1H), 0.97-1.05 (m, 6H), 0.89-0.95 (m, 6H).

B. (3S)-3-Cyclopropyl-3-(3-((5-(2-fluoro-5-methoxyphenyl)-6-(2,2,6,6-tetramethyl-tetrahydro-2H-pyran-4-yloxy)pyrazin-2-yl)methoxy)phenyl) propanoic acid, Cpd 26

The title compound 26 was prepared from compound 1g and compound 10a following an adaptation of the procedure described in Example 3, refluxing for 2 h rather than overnight. $^1$H-NMR (300 MHz, DMSO-d$_6$) δ (ppm): 8.46 (s, 1H), 7.18-7.27 (m, 2H), 7.03-7.07 (m, 2H), 6.85-6.92 (m, 3H), 5.53-5.55 (m, 1H), 5.23 (s, 2H), 3.77 (s, 3H), 2.50-2.61 (m, 2H), 2.26-2.28 (m, 1H), 2.00-2.06 (m, 2H), 1.24-1.36 (m, 8H), 1.12 (s, 6H), 0.95-0.98 (m, 1H), 0.45-0.48 (m, 1H), 0.13-0.29 (m, 2H), 0.09-0.11 (m, 1H). Mass Spectrum (LCMS, ESI pos.): Calcd. for $C_{33}H_{39}FN_2O_6$: 579.3 (M+H)$^+$; found: 579.3.

Example 11

(3S)-3-[3-[(6-[2-Azaspiro[3.3]heptan-2-yl]-5-(2-fluoro-5-methoxyphenyl)pyrazin-2-yl)methoxy]phenyl]-3-cyclopropylpropanoic acid (Cpd. 6)

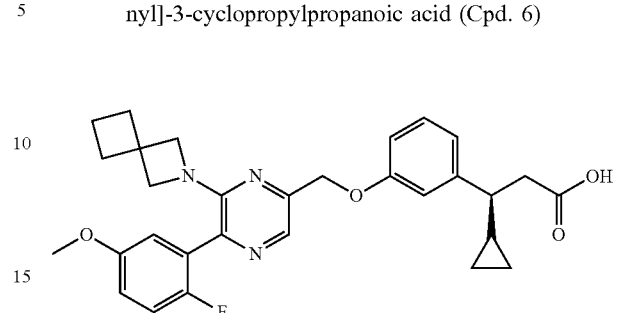

A. Ethyl (3S)-3-[3-[(6-[2-azaspiro[3.3]heptan-2-yl]-5-(2-fluoro-5-methoxyphenyl)pyrazin-2-yl)methoxy] phenyl]-3-cyclopropylpropanoate, 11a

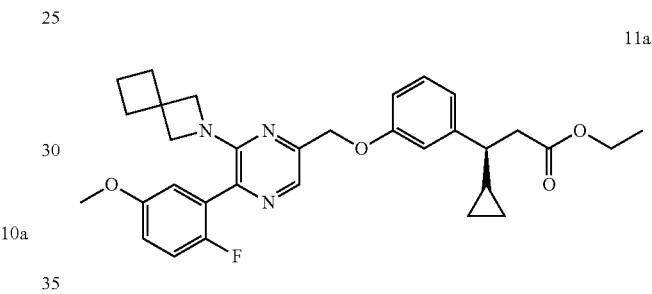

11a

A mixture of compound 1g (80 mg, 0.16 mmol), 2-azaspiro[3.3]heptane (77 mg, 0.41 mmol), Pd(OAc)$_2$ (5.0 mg, 0.020 mmol), BINAP (26 mg, 0.04 mmol) and Cs$_2$CO$_3$ (202 mg, 0.620 mmol) in toluene (3 mL) was stirred for 4 h at 110° C. The reaction mixture was allowed to cool to RT and treated with 5 mL of saturated NH$_4$Cl solution before extraction with EtOAc (3×10 mL). The organic layers were combined and concentrated. The residue obtained was purified by column chromatography on silica gel (EtOAc/petroleum ether (2:8 v/v)) to obtain the title compound 11a. Mass Spectrum (LCMS, ESI pos.): Calcd. for $C_{32}H_{36}FN_3O_4$: 546.3 (M+H)$^+$; found: 546.3.

B. (3S)-3-[3-[(6-[2-Azaspiro[3.3]heptan-2-yl]-(2-fluoro-5-methoxyphenyl)pyrazin-2-yl)methoxy]phenyl]-3-cyclopropylpropanoic acid, Cpd 6

A mixture of compound 11a (80 mg, 0.15 mmol) and LiOH.H$_2$O (62 mg, 1.5 mmol) in tetrahydrofuran (2 mL) and water (1 mL) was stirred overnight at RT. The reaction mixture was concentrated to remove the organic solvents and the resulting solution was diluted with 5 mL of water and the pH of the solution was adjusted to 5 with 1N HCl. The resulting solids were collected by filtration to give the title compound 6. $^1$H-NMR (300 MHz, DMSO-d$_6$) δ (ppm): 12.01 (s, 1H), 8.09 (s, 1H), 7.19-7.26 (m, 2H), 6.85-7.07 (m, 5H), 5.09 (s, 2H), 3.77 (s, 3H), 3.65 (s, 4H), 2.63-67 (m, 2H), 2.24-2.27 (m, 1H), 2.01-2.06 (m, 4H), 1.66-1.74 (m, 2H), 0.98-1.01 (m, 1H), 0.47-0.50 (m, 1H), 0.21-0.30 (m, 2H), 0.09-0.12 (m, 1H). Mass Spectrum (LCMS, ESI pos.): Calcd. for $C_{30}H_{32}FN_3O_4$: 518.2 (M+H)$^+$; found: 518.1.

Example 12

(3S)-3-((6-Cyclobutoxy-5-(2-fluoro-5-methoxyphenyl)pyrazin-2-yl)methoxy)phenyl)-3-cyclopropyl-propanoic acid (Cpd. 19)

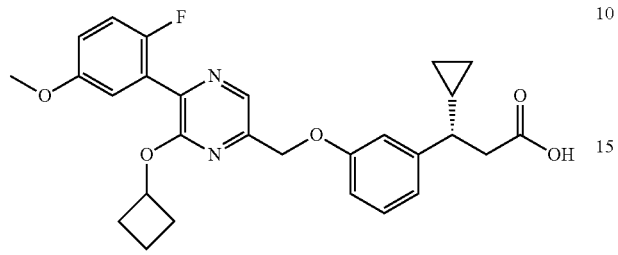

The title compound 19 was prepared from compound 1g and cyclobutanol following an adaptation of the procedure described in Example 3 treating the alcohol with NaH at RT for 30 min and heating at 75° C. for 1 h rather than treating the alcohol with NaH at 0° C. for 10 min. and refluxing overnight. $^1$H-NMR (300 MHz, DMSO-d$_6$) δ (ppm): 12.00 (br, 1H), 8.45 (s, 1H), 7.20-7.29 (m, 2H), 7.04-7.08 (m, 2H), 6.97 (s, 1H), 6.86-6.93 (m, 2H), 5.17-5.22 (m, 3H), 3.78 (s, 3H), 2.64-2.67 (m, 2H), 2.25-2.38 (m, 3H), 1.95-2.02 (m, 2H), 1.60-1.77 (m, 2H), 0.95-1.10 (m, 1H), 0.48-0.51 (m, 1H), 0.22-0.30 (m, 2H), 0.07-0.09 (m, 1H). Mass Spectrum (LCMS, ESI pos.): Calcd. for C$_{28}$H$_{29}$FN$_2$O$_5$: 493.2 (M+H)$^+$; found: 493.2.

Example 13

(3S)-3-Cyclopropyl-3-(3-((5-(2-fluoro-5-methoxyphenyl)-6-phenylpyrazin-2-yl)methoxy)phenyl)propanoic acid (Cpd. 18)

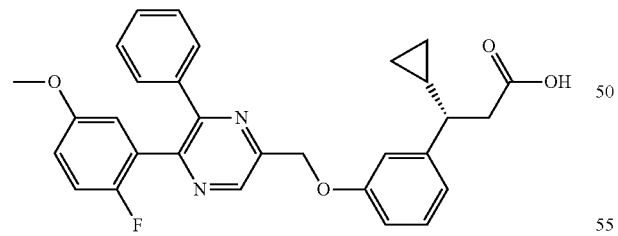

The title compound was prepared from compound 1g and phenyl boronic acid following the procedure described in Example 2, steps G-H). $^1$H-NMR (400 MHz, DMSO-d$_6$) δ (ppm): 8.86 (s, 1H), 7.31-7.44 (m, 5H), 7.24 (t, J=7.8 Hz, 1H), 7.13-7.16 (m, 1H), 6.88-7.06 (m, 5H), 5.37 (s, 2H), 3.75 (s, 3H), 2.59-2.73 (m, 2H), 2.19-2.32 (m, 1H), 0.90-1.05 (m, 1H), 0.44-0.54 (m, 1H), 0.21-0.40 (m, 2H), 0.02-0.18 (m, 1H). Mass Spectrum (LCMS, ESI neg.): Calcd. for C$_{30}$H$_{27}$FN$_2$O$_4$: 497.2 (M–H)$^-$; found: 497.2.

Example 14

(S)-3-cyclopropyl-3-(3-((5-(2-fluoro-5-methoxyphenyl)-6-(m-tolyl)pyrazin-2-yl)methoxy)phenyl)propanoic acid (Cpd. 20)

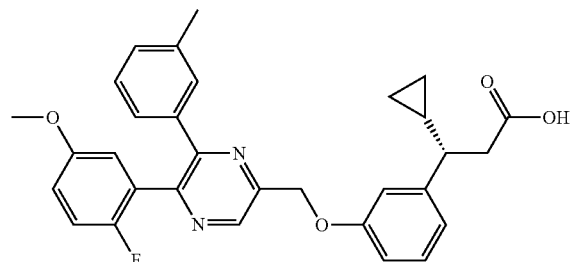

A. Methyl 6-bromo-5-(2-fluoro-5-methoxyphenyl)pyrazine-2-carboxylate, 14a

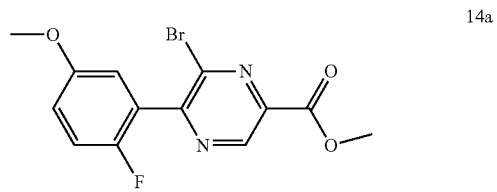

To a suspension of methyl 6-amino-5-(2-fluoro-5-methoxyphenyl)pyrazine-2-carboxylate (1b) (1.6 g, 5.7 mmol) in CH$_2$Br$_2$ (40 mL) at 0° C. was added TMSBr (1.9 mL, 14 mmol) followed by iso-amylnitrite (6.9 mL, 58 mmol). The mixture was stirred for 3 h at 0° C., followed by 2 h at room temperature. To the resulting turbid reaction mixture was added ~15 mL of a 10% aqueous sodium bicarbonate solution with stirring. The phases were separated and the organic phase was dried (magnesium sulfate) and concentrated. The residue obtained was purified by column chromatography on silica gel (heptane/EtOAc (1:0-1:1)) to give the title compound 14a. Mass Spectrum (LCMS, ESI pos.): Calcd. for C$_{13}$H$_{10}$BrFN$_2$O$_3$: 340.9 (M+H)$^+$; found: 341.0.

B. (6-Bromo-5-(2-fluoro-5-methoxyphenyl)pyrazin-2-yl)methanol, 14b

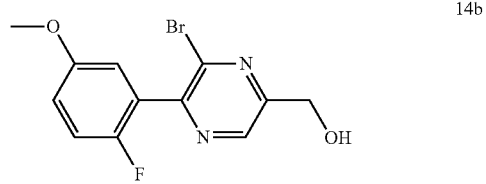 [SMILES: COc1ccc(F)c(-c2ncc(CO)nc2Br)c1]

To a solution of methyl 6-bromo-5-(2-fluoro-5-methoxyphenyl)pyrazine-2-carboxylate (14a) (226 mg, 0.662 mmol) in THF (3 mL), 1M DIBAL-H in THF (5.3 mL, 5.3 mmol) was added at −78° C. After stirring 1 h at −78° C. the reaction mixture was treated with ethanol (3 ml) and saturated potassium sodium tartrate (3 mL). The aqueous layer was extracted with ethyl acetate (3×20 mL). The combined organic layers were dried (Na$_2$SO$_4$) and concentrated. The residue obtained was purified by column chromatography on silica gel (heptane/EtOAc 5:1) to give the title compound 14b. Mass Spectrum (LCMS, ESI pos.): Calcd. for $C_{12}H_{10}BrFN_2O$: 312.9 (M+H)$^+$; found: 313.0.

C. (S)-Ethyl 3-(3-((6-bromo-5-(2-fluoro-5-methoxyphenyl)pyrazin-2-yl)methoxy)phenyl)-3-cyclopropylpropanoate, 14c

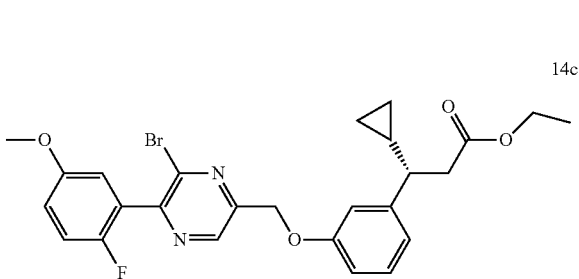 [SMILES: CCOC(=O)C[C@H](c1cccc(OCc2cnc(-c3cc(OC)ccc3F)c(Br)n2)c1)C1CC1]

To a stirred mixture of (6-bromo-5-(2-fluoro-5-methoxyphenyl)pyrazin-2-yl)methanol (14b) (182 mg, 0.580 mmol), ethyl (3S)-3-cyclopropyl-3-(3-hydroxyphenyl)propanoate (1f) (136 mg, 0.580 mmol) and PS-PPh$_3$ (0.451 mg, 0.871 mmol) in DCM (5 mL), DEAD (0.138 mL, 0.871 mmol) was added dropwise at 0° C. The resulting mixture was stirred at RT overnight and filtered. The filtrate was concentrated and the residue obtained was purified by column chromatography on silica gel (0-50% EtOAc/heptane) to obtain the title compound 14c. Mass Spectrum (LCMS, ESI pos.): Calcd. for $C_{26}H_{26}BrFN_2O_4$: 529.1 (M+H)$^+$; found: 529.2.

D. (S)-3-Cyclopropyl-3-(3-((5-(2-fluoro-5-methoxyphenyl)-6-(m-tolyl)pyrazin-2-yl)methoxy)phenyl)propanoic acid, Cpd 20

The title compound 20 was prepared from ethyl (3S)-3-(3-[[6-bromo-5-(2-fluoro-5-methoxyphenyl)pyrazin-2-yl]methoxy]phenyl)-3-cyclopropylpropanoate (14c) and 3-methyl-phenyl boronic acid following the procedure described in Example 2, steps G-H. $^1$H-NMR (300 MHz, CDCl$_3$) δ (ppm): $^1$H NMR (CDCl$_3$): 8.85 (s, 1H), 7.37 (s, 1H), 7.22-7.29 (m, 2H), 7.12-7.17 (m, 2H), 7.02-7.07 (m, 1H), 6.96 (s, 1H), 6.83-6.93 (m, 4H), 5.35 (s, 2H), 3.78 (s, 3H), 2.77 (m, 2H), 2.29-2.40 (s, 4H), 0.96-1.06 (m, 1H), 0.57 (m, 4.2 Hz, 1H), 0.41 (m, 1H), 0.28 (m, 1H), 0.11-0.19 (m, 1H). Mass Spectrum (LCMS, ESI pos.): Calcd. for $C_{31}H_{29}FN_2O_4$: 513.2 (M+H)$^+$; found: 513.5.

Example 15

(3S)-3-(3-((6-Butyl-5-(2-fluoro-5-methoxyphenyl)pyrazin-2-yl)methoxy)phenyl)-3-cyclopropylpropanoic acid (Cpd. 3)

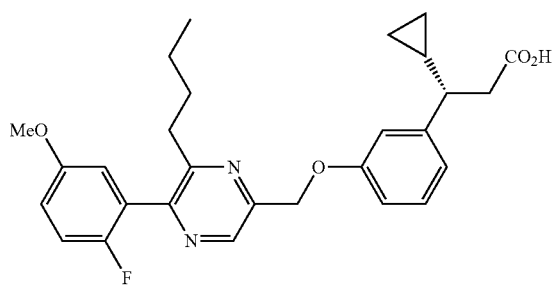 [SMILES: CCCCc1nc(COc2cccc([C@@H](CC(=O)O)C3CC3)c2)cnc1-c1cc(OC)ccc1F]

A. (3S)-Ethyl 3-(3-((6-butyl-5-(2-fluoro-5-methoxyphenyl)pyrazin-2-yl)methoxy)phenyl)-3-cyclopropylpropanoate, 15a

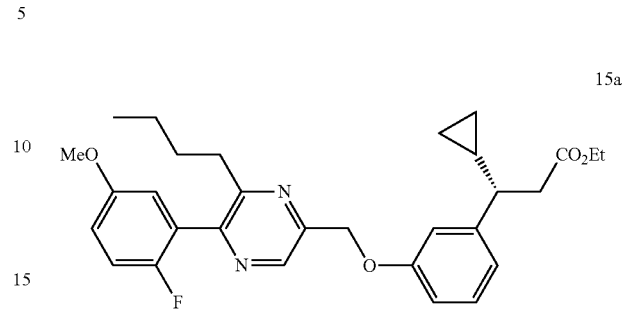

A mixture of ZnCl$_2$ (680 mg, 4.99 mmol), Mg (180 g, 7.50 mol) and 1-bromobutane (1.02 g, 7.44 mmol) in tetrahydrofuran (10 mL) was stirred overnight at 60° C. The reaction mixture was allowed to cool to room temperature to give a gray solution which was used in the next step without further purification.

A mixture of compound 1g (100.0 mg, 0.210 mmol), a solution of the zinc reagent (2 mL, as prepared above) and Pd(dppf)Cl$_2$ (20 mg, 0.03 mmol) in tetrahydrofuran (5 mL) was stirred for 4 h at 60° C. under N$_2$. The reaction was then quenched by the addition of 5 mL of water. The resulting solution was extracted with EtOAc (3×10 mL). The organic layers were combined, dried (Na$_2$SO$_4$) and concentrated. The residue obtained was purified by column chromatography on silica gel (EtOAc/petroleum ether (1:10-1:5 v/v)) to give the title compound 15a. Mass Spectrum (LCMS, ESI pos.): Calcd. for $C_{30}H_{35}FN_2O_4$: 507.3 (M+H)$^+$; found: 507.1.

B. (3S)-3-(3-((6-Butyl-5-(2-fluoro-5-methoxyphenyl)pyrazin-2-yl)methoxy)phenyl)-3-cyclopropylpropanoic acid, 15b

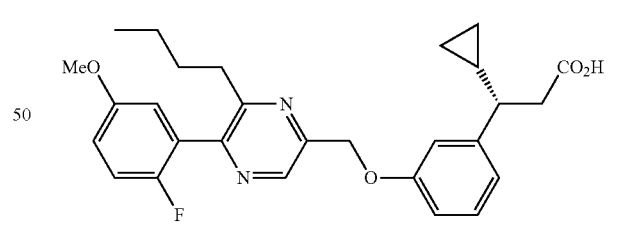

The title compound was prepared from (3S)-3-(3-[[6-butyl-5-(2-fluoro-5-methoxyphenyl)pyrazin-2-yl]methoxy]phenyl)-3-cyclopropylpropanoate (15a) following the procedure described in Example 2, step H. $^1$H-NMR (300 MHz, DMSO-d$_6$) δ (ppm): 8.73 (s, 1H), 7.20-7.33 (m, 2H), 6.87-7.10 (m, 5H), 5.28 (s, 2H), 3.89 (s, 3H), 2.61-2.69 (m, 4H), 2.24-2.30 (m, 1H), 1.53-1.60 (m, 2H), 1.16-1.23 (m, 2H), 0.91-1.00 (m, 1H), 0.76 (t, J=7.2 Hz, 3H), 0.48-0.49 (m, 1H), 0.22-0.31 (m, 2H), 0.10-0.11 (m, 1H). Mass Spectrum (LCMS, ESI pos.): Calcd. for $C_{28}H_{31}FN_2O_4$: 479.2 (M+H)$^+$; found: 479.1.

Example 16

(3S)-3-Cyclopropyl-3-(3-((5-(2-fluoro-5-methoxyphenyl)-6-neopentylpyrazin-2-yl)methoxy)phenyl)propanoic acid (Cpd. 1)

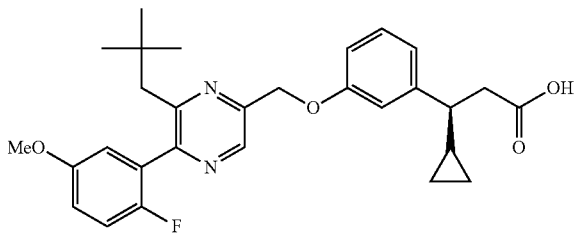 [SMILES: COc1ccc(F)c(-c2ncc(COc3cccc([C@@H](CC(=O)O)C4CC4)c3)nc2CC(C)(C)C)c1]

A. 5-((tert-Butyldimethylsilyloxy)methyl)-3-chloro-2-(2-fluoro-5-methoxyphenyl)pyrazine, 16a

16a

To a solution of [6-chloro-5-(2-fluoro-5-methoxyphenyl)pyrazin-2-yl]methanol (1d) (5.1 g, 19 mmol) and imidazole (2.6 g, 38 mmol) in dichloromethane (200 mL), TBSCl (3 g, 21 mmol) was added in portions at 0° C. The resulting solution was stirred overnight at RT. The reaction was then quenched by the addition of water (100 mL). The resulting solution was extracted with dichloromethane (2×100 mL). The organic layers were combined and concentrated. The residue obtained was purified by column chromatography on silica gel (EtOAc/petroleum ether (1:20-1:10 v/v)) to give the title compound 16a. Mass Spectrum (LCMS, ESI pos.): Calcd. for $C_{18}H_{24}ClFN_2O_2Si$: 383.1 (M+H)$^+$; found: 383.0.

B. 5-((tert-Butyldimethylsilyloxy)methyl)-2-(2-fluoro-5-methoxyphenyl)-3-neopentylpyrazine, 16b

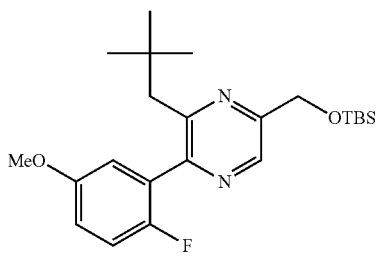

16b

To a mixture of ZnCl$_2$ (680 mg, 4.99 mmol) and Mg (180 mg, 7.50 mmol) in tetrahydrofuran (5 mL) was added a solution of 1-bromo-2,2-dimethylpropane (1.12 g, 7.45 mmol) in tetrahydrofuran (5 mL) dropwise with stirring under N$_2$. The resulting solution was stirred overnight at 50° C. to give 10 mL of a gray liquid which was used in the next step directly without further purification.

A mixture of 5-[[(tert-butyldimethylsilyl)oxy]methyl]-3-chloro-2-(2-fluoro-5-methoxyphenyl)pyrazine (16a) (170 mg, 0.44 mmol), a solution of zinc reagent (6 mL, as prepared above) and Pd(dppf)Cl$_2$ (35 mg, 0.05 mmol) in tetrahydrofuran (3 mL) was stirred for 4 h at 60° C. The reaction was then quenched by the addition of saturated NH$_4$Cl solution (1 mL). The resulting solution was extracted with EtOAc (2×10 mL). The organic layers were combined and concentrated. The residue obtained was purified by column chromatography on silica gel (EtOAc/petroleum ether (1:20 v/v)) to give the title compound. Mass Spectrum (LCMS, ESI pos.): Calcd. for $C_{23}H_{35}FN_2O_2Si$: 419.2 (M+H)$^+$; found: 419.4.

C. (5-(2-Fluoro-5-methoxyphenyl)-6-neopentylpyrazin-2-yl)methanol, 16c

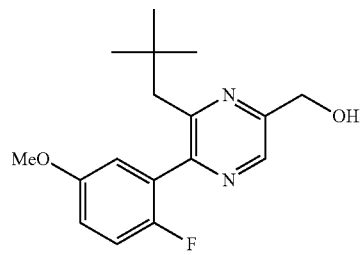

16c

To a solution of 5-[[(tert-Butyldimethylsilyl)oxy]methyl]-3-(2,2-dimethylpropyl)-2-(2-fluoro-5-methoxyphenyl)pyrazine (16b) (210 mg, 0.500 mmol) in tetrahydrofuran (5 mL) was added 1M TBAF solution in THF (1.5 mL, 1.5 mmol). The resulting solution was stirred for 30 min at RT. The reaction was then quenched by the addition of saturated NH$_4$Cl (10 mL). The resulting solution was extracted with EtOAc (3×20 mL). The organic layers were combined and concentrated. The residue obtained was purified by column chromatography on silica gel (EtOAc/petroleum ether (1:5 v/v)) to give the title compound 16c. Mass Spectrum (LCMS, ESI pos.): Calcd. for $C_{17}H_{21}FN_2O_2$: 305.2 (M+H)$^+$; found: 305.1.

D. 5-(Chloromethyl)-2-(2-fluoro-5-methoxyphenyl)-3-neopentylpyrazine, 16d

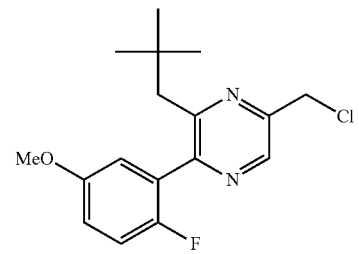

16d

To a solution of [6-(2,2-dimethylpropyl)-5-(2-fluoro-5-methoxyphenyl)pyrazin-2-yl]methanol (16c) (141 mg, 0.460 mmol) in dichloromethane (5 mL) and DMF (0.5 mL) was added thionyl chloride (110 mg, 0.920 mmol). The resulting solution was stirred for 30 min at 0° C. The reaction was then quenched by the addition of 1 mL of saturated NaHCO$_3$ solution. The resulting solution was extracted with dichloromethane (2×10 mL). The organic layers were combined, dried (Na$_2$SO$_4$) and concentrated to give the title compound 16d as a yellow oil. Mass Spectrum (LCMS, ESI pos.): Calcd. for $C_{17}H_{20}ClFN_2O$: 323.1 (M+H)$^+$; found: 323.1.

E. (3S)-Ethyl 3-cyclopropyl-3-(3-((5-(2-fluoro-5-methoxyphenyl)-6-neopentylpyrazin-2-yl)methoxy)phenyl)propanoate, 16e

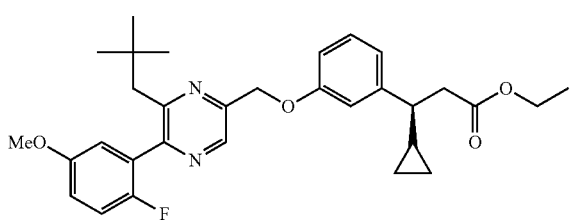

A mixture of 5-(chloromethyl)-3-(2,2-dimethylpropyl)-2-(2-fluoro-5-methoxyphenyl)pyrazine (16d) (149 mg, 0.460 mmol), ethyl (3S)-3-cyclopropyl-3-(3-hydroxyphenyl)propanoate (1f) (112 mg, 0.480 mmol) and $Cs_2CO_3$ (300 mg, 0.920 mmol) in $CH_3CN$ (5 mL) was stirred overnight at RT. The reaction was then quenched by the addition of 10 mL of water. The resulting solution was extracted with EtOAc (3×20 mL). The organic layers were combined and concentrated. The residue obtained was purified by column chromatography on silica gel (EtOAc/petroleum ether (1:20-1:10 v/v)) to give the title compound 16e. Mass Spectrum (LCMS, ESI pos.): Calcd. for $C_{31}H_{37}FN_2O_4$: 521.3 $(M+H)^+$; found: 521.3.

F. (3S)-3-Cyclopropyl-3-(3-((5-(2-fluoro-5-methoxyphenyl)-6-neopentylpyrazin-2-yl)methoxy)phenyl)propanoic acid, Cpd 1

The title compound was prepared from (3S)-ethyl-3-cyclopropyl-3-(3-[[6-(2,2-dimethylpropyl)-5-(2-fluoro-5-methoxyphenyl)pyrazin-2-yl]methoxy]phenyl)propanoate (16e) following the procedure described in Example 2, step H. $^1$H-NMR (300 MHz, DMSO-$d_6$) δ (ppm): 8.74 (s, 1H), 7.18-7.31 (m, 2H), 6.96-7.11 (m, 2H), 6.86-6.92 (m, 3H), 5.29 (s, 2H), 3.77 (s, 3H), 2.72 (s, 2H), 2.50-2.63 (m, 2H), 2.25-2.28 (m, 1H), 0.99-1.00 (m, 1H), 0.75 (s, 9H), 0.47-0.49 (m, 1H), 0.21-0.29 (m, 2H), 0.05-0.11 (m, 1H). Mass Spectrum (LCMS, ESI pos.): Calcd. for $C_{29}H_{33}FN_2O_4$: 493.2 $(M+H)^+$; found: 493.3.

Example 17

(3S)-3-Cyclopropyl-3-(3-((6-(cyclopropylmethoxy)-5-(2-fluoro-5-methoxyphenyl)pyrazin-2-yl)methoxy)phenyl)propanoic acid (Cpd. 21)

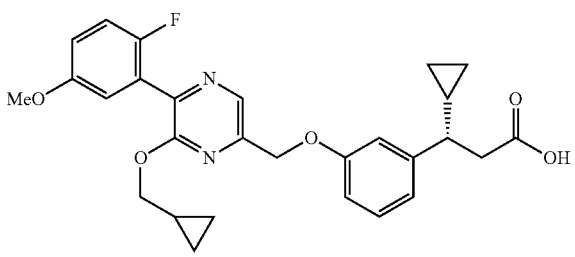 [SMILES: COc1ccc(F)c(-c2ncc(COc3cccc([C@@H](CC(=O)O)C4CC4)c3)nc2OCC2CC2)c1]

The title compound 21 was prepared from compound 1g and cyclopropylmethanol following an adaptation of the procedure described in Example 3 treating the alcohol with NaH at RT for 30 min and heating at 50° C. overnight rather than treating the alcohol with NaH at 0° C. for 10 min. and refluxing overnight. $^1$H-NMR (300 MHz, DMSO-$d_6$) δ (ppm): 12.01 (brs, 1H), 8.45 (s, 1H), 7.20-7.28 (m, 2H), 7.04-7.12 (m, 2H), 6.99 (s, 1H), 6.86-6.93 (m, 2H), 5.20 (s, 2H), 4.20 (d, J=6.9 Hz, 2H), 3.78 (s, 3H), 2.64-2.67 (m, 2H), 2.25-2.28 (m, 1H), 1.12-1.22 (m, 1H), 0.90-1.00 (m, 1H), 0.49-0.53 (m, 3H), 0.22-0.34 (m, 4H), 0.10-0.13 (m, 1H). Mass Spectrum (LCMS, ESI pos.): Calcd. for $C_{28}H_{29}FN_2O_5$: 493.2 $(M+H)^+$; found: 493.1.

Example 18

(3S)-3-Cyclopropyl-3-(3-((5-(2-fluoro-5-methoxyphenyl)-6-(neopentyloxy)pyrazin-2-yl)methoxy)phenyl)propanoic acid (Cpd. 4)

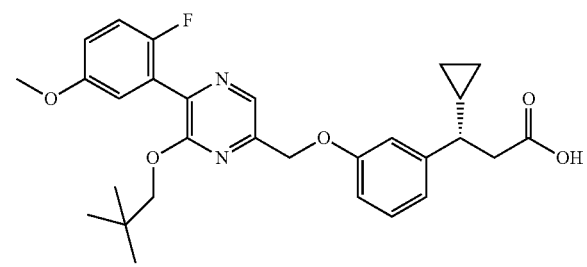 [SMILES: COc1ccc(F)c(-c2ncc(COc3cccc([C@@H](CC(=O)O)C4CC4)c3)nc2OCC(C)(C)C)c1]

The title compound was prepared from compound 1g and 2,2-dimethylpropan-1-ol following an adaptation of the procedure described in Example 3 treating the alcohol with NaH at RT for 30 min and heating at 75° C. for 1 h rather than treating the alcohol with NaH at 0° C. for 10 min. and refluxing overnight. $^1$H-NMR (300 MHz, DMSO-$d_6$) δ (ppm): 8.46 (s, 1H), 7.20-7.29 (m, 2H), 7.05-7.08 (m, 2H), 6.87-6.99 (m, 3H), 5.20 (s, 2H), 4.00 (s, 2H), 3.77 (s, 3H), 2.51-2.68 (m, 2H), 2.25-2.31 (m, 1H), 0.89-1.02 (m, 1H), 0.86 (s, 9H), 0.48-0.51 (m, 1H), 0.18-0.35 (m, 2H), 0.09-0.11 (m, 1H). Mass Spectrum (LCMS, ESI pos.): Calcd. for $C_{29}H_{33}FN_2O_5$: 509.2 $(M+H)^+$; found: 509.4.

Example 19

(3S)-3-(3-((6-(Cyclohexyloxy)-5-(2-fluoro-5-methoxyphenyl)pyrazin-2-yl)methoxy)phenyl)-3-cyclopropylpropanoic acid (Cpd. 7)

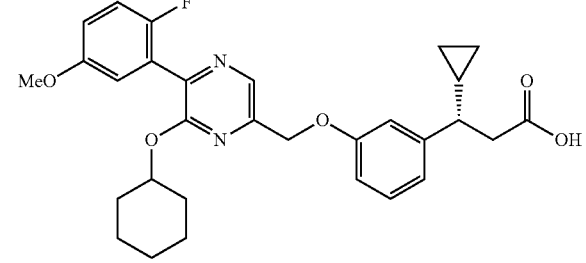

The title compound was prepared from compound 1g and cyclohexanol following an adaptation of the procedure described in Example 3, refluxing for 2 h rather than overnight. $^1$H-NMR (300 MHz, DMSO-$d_6$) δ (ppm): 8.42 (s, 1H), 7.20-7.27 (m, 2H), 7.04-7.10 (m, 2H), 6.88-6.98 (m, 3H), 5.21 (s, 2H), 5.08-5.11 (m, 1H), 3.77 (s, 3H), 2.64-2.67 (m, 2H), 2.25-2.28 (m, 1H), 1.86-1.88 (m, 2H), 1.33-1.60 (m, 8H), 0.90-1.00 (m, 1H), 0.48-0.50 (m, 1H), 0.25-0.30

(m, 2H), 0.07-0.10 (m, 1H). Mass Spectrum (LCMS, ESI pos.): Calcd. for $C_{30}H_{33}FN_2O_5$: 521.2 (M+H)$^+$; found: 521.1.

Example 20

(3S)-3-(3-((6-(Cyclopentyloxy)-5-(2-fluoro-5-methoxyphenyl)pyrazin-2-yl)methoxy)phenyl)-3-cyclopropylpropanoic acid (Cpd. 13)

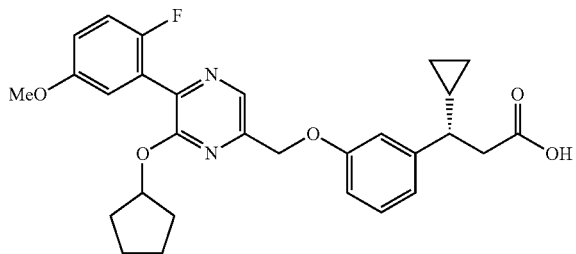

The title compound was prepared from compound 1g and cyclopentanol following an adaptation of the procedure described in Example 3, refluxing for 2 h rather than overnight. $^1$H-NMR (300 MHz, DMSO-d$_6$) δ (ppm): 8.43 (s, 1H), 7.19-7.26 (m, 2H), 7.02-7.06 (m, 2H), 6.94-6.98 (m, 1H), 6.86-6.93 (m, 2H), 5.44-5.46 (m, 1H), 5.21 (s, 2H), 3.77 (s, 3H), 2.64-2.67 (m, 2H), 2.25-2.28 (m, 1H), 1.87-1.91 (m, 2H), 1.58-1.67 (m, 6H), 0.98-1.00 (m, 1H), 0.48-0.50 (m, 1H), 0.25-0.30 (m, 2H), 0.07-0.10 (m, 1H). Mass Spectrum (LCMS, ESI pos.): Calcd. for $C_{29}H_{31}FN_2O_5$: 507.2 (M+H)$^+$; found: 507.1.

Example 21

(3S)-3-Cyclopropyl-3-(3-((6-(dimethylamino)-5-(2-fluoro-5-methoxyphenyl)pyrazin-2-yl)methoxy)phenyl)propanoic acid (Cpd. 38)

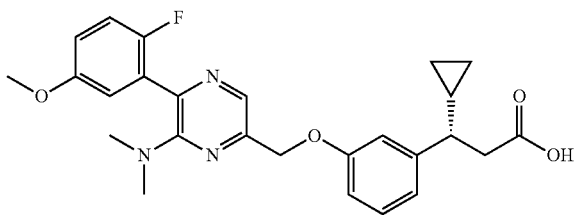 [SMILES: COc1ccc(F)c(-c2ncc(COc3cccc([C@@H](CC(=O)O)C4CC4)c3)nc2N(C)C)c1]

A. (3S)-Ethyl 3-cyclopropyl-3-(3-((6-(dimethylamino)-5-(2-fluoro-5-methoxyphenyl)pyrazin-2-yl)methoxy)phenyl)propanoate (21a) and (3S)-ethyl 3-cyclopropyl-3-(3-[[5-(2-fluoro-5-methoxyphenyl)-6-[methyl(propan-2-yl)amino]pyrazin-2-yl]methoxy]phenyl)propanoate (21b)

(21a)

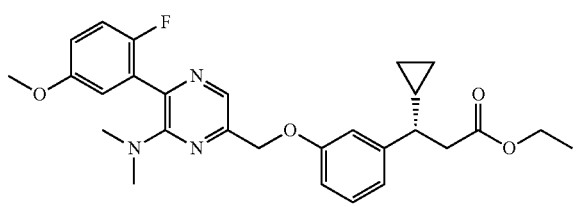

(21b)

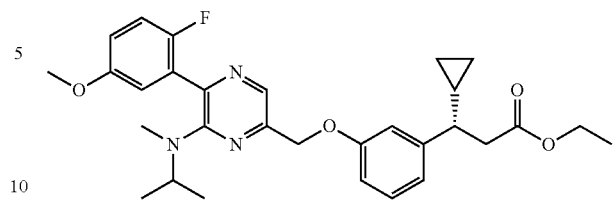

A solution of compound 1g (150 mg, 0.31 mmol) and methyl(propan-2-yl)amine (226 mg, 3.09 mmol) in DMF (1 mL) was stirred overnight at 120° C. in an 8 mL sealed tube. The resulting solution was diluted with 5 mL of water. The pH value of the solution was adjusted to 6 with HCl (6N). The resulting solution was extracted with EtOAc (3×10 mL). The organic layers were combined, dried (Na$_2$SO$_4$) and concentrated under reduced pressure. The residue obtained was a mixture which contained (3S)-ethyl 3-cyclopropyl-3-(3-[[6-(dimethylamino)-5-(2-fluoro-5-methoxyphenyl)pyrazin-2-yl]methoxy]phenyl)propanoate (21a) and (3S)-ethyl 3-cyclopropyl-3-(3-[[5-(2-fluoro-5-methoxyphenyl)-6-[methyl(propan-2-yl)amino]pyrazin-2-yl]methoxy]phenyl)propanoate (21b). Compound (21a): Mass Spectrum (LCMS, ESI pos.): Calcd. for $C_{28}H_{32}FN_3O_4$: 494.2 (M+H)$^+$; found: 494.1; Compound (21b): Mass Spectrum (LCMS, ESI pos.): Calcd. for $C_{30}H_{36}FN_3O_4$: 522.3 (M+H)$^+$; found: 522.2.

B. (3S)-3-Cyclopropyl-3-(3-((6-(dimethylamino)-5-(2-fluoro-5-methoxyphenyl)pyrazin-2-yl)methoxy)phenyl)propanoic acid, Cpd 38

A mixture of (3S)-ethyl 3-cyclopropyl-3-(3-[[6-(dimethylamino)-5-(2-fluoro-5-methoxyphenyl)pyrazin-2-yl]methoxy]phenyl)propanoate (21a) and (3S)-ethyl 3-cyclopropyl-3-(3-[[5-(2-fluoro-5-methoxyphenyl)-6-[methyl(propan-2-yl)amino]pyrazin-2-yl]methoxy]phenyl)propanoate (21b) (120 mg, crude), sodium hydroxide (33 mg, 0.82 mmol) in tetrahydrofuran (2 mL) and water (1 mL) was stirred for 2 days at 40° C. The reaction mixture was allowed to cool to RT and concentrated to remove most of the organic solvents. The resulting solution was diluted with 2 mL of water. The pH value of the solution was adjusted to 6 with HCl (1N). The resulting solution was extracted with EtOAc (2×10 mL) and the organic layers were combined, dried (Na$_2$SO$_4$) and concentrated under reduced pressure. The residue obtained was purified by reverse phase Prep-HPLC using water and CH$_3$CN as the mobile phase to give the title compound 38. $^1$H-NMR (300 MHz, DMSO-d$_6$) δ (ppm): 8.09 (s, 1H), 7.22-7.27 (m, 1H), 7.11-7.18 (m, 2H), 6.89-7.10 (m, 4H), 5.19 (s, 2H), 3.85 (s, 3H), 2.29 (s, 6H), 2.66-2.78 (m, 2H), 2.34-2.37 (m, 1H), 1.05-1.08 (m, 1H), 0.58-0.62 (m, 1H), 0.25-0.41 (m, 2H), 0.06-0.14 (m, 1H). Mass Spectrum (LCMS, ESI pos.): Calcd. for $C_{26}H_{28}FN_3O_4$: 466.2 (M+H)$^+$; found: 466.2.

Example 22

((3S)-3-Cyclopropyl-3-(3-((5-(2-fluoro-5-methoxyphenyl)-6-(2-methylprop-1-enyl)pyrazin-2-yl)methoxy)phenyl)propanoic acid (Cpd. 8)

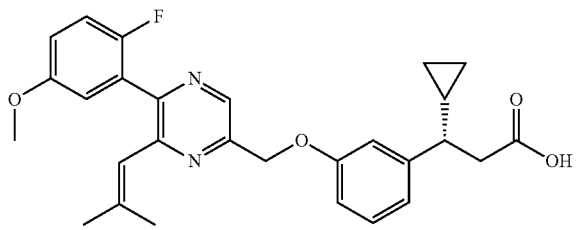 [SMILES: COc1ccc(F)c(-c2ncc(COc3cccc([C@@H](CC(=O)O)C4CC4)c3)nc2C=C(C)C)c1]

The title compound 8 was prepared from compound 1g and 4,4,5,5-tetramethyl-2-(2-methylprop-1-en-1-yl)-1,3,2-dioxaborolane, following the procedure described in Example 2, Steps G-H. $^1$H-NMR (300 MHz, DMSO-d$_6$) δ (ppm): 8.67 (s, 1H), 7.22-7.29 (m, 2H), 6.84-7.19 (m, 5H), 6.07 (s, 1H), 5.28 (s, 2H), 3.77 (s, 3H), 2.58-2.62 (m, 1H), 2.41-2.46 (m, 1H), 2.27-2.31 (m, 1H), 2.03 (s, 3H), 1.82 (s, 3H), 0.90-1.01 (m, 1H), 0.40-0.48 (m, 1H), 0.20-0.32 (m, 2H), 0.01-0.12 (m, 1H). Mass Spectrum (LCMS, ESI pos.): Calcd. for $C_{28}H_{29}FN_2O_4$: 477.2 (M+H)$^+$; found: 477.2.

Example 23

(3S)-3-Cyclopropyl-3-(3-((5-(2-fluoro-5-methoxyphenyl)-6-(1,1,1-trifluoropropan-2-yl)pyrazin-2-yl)methoxy)phenyl)propanoic acid (Cpd. 40)

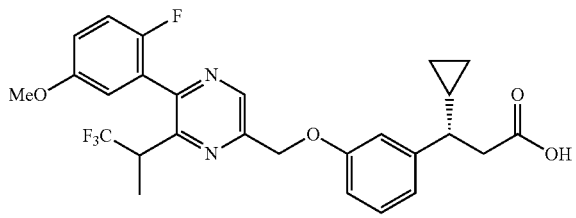 [SMILES: COc1ccc(F)c(-c2ncc(COc3cccc([C@@H](CC(=O)O)C4CC4)c3)nc2C(C)C(F)(F)F)c1]

A. (3S)-Ethyl 3-cyclopropyl-3-(3-((5-(2-fluoro-5-methoxyphenyl)-6-(3,3,3-trifluoroprop-1-en-2-yl)pyrazin-2-yl)methoxy)phenyl)propanoate, 23a

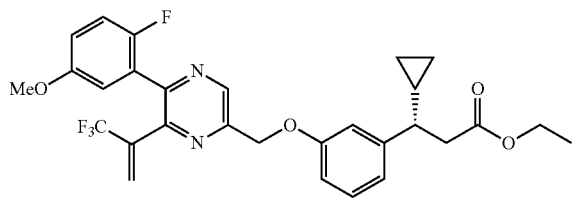

The title compound 23a was prepared from compound 1g and (3,3,3-trifluoroprop-1-en-2-yl)boronic acid following the procedure described in Example 2, Step G. Mass Spectrum (LCMS, ESI pos.): Calcd. for $C_{29}H_{28}F_4N_2O_4$: 545.2 (M+H)$^+$; found: 545.2.

B. (3S)-Ethyl 3-cyclopropyl-3-(3-((5-(2-fluoro-5-methoxyphenyl)-6-(1,1,1-trifluoropropan-2-yl)pyrazin-2-yl)methoxy)phenyl)propanoate, 23b

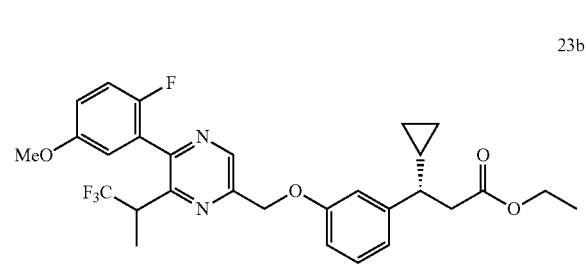 [SMILES: CCOC(=O)C[C@H](c1cccc(OCc2cnc(-c3cc(OC)ccc3F)c(C(C)C(F)(F)F)n2)c1)C1CC1]

(3S)-Ethyl 3-cyclopropyl-3-(3-((5-(2-fluoro-5-methoxyphenyl)-6-(3,3,3-trifluoroprop-1-en-2-yl)pyrazin-2-yl)methoxy)phenyl)propanoate (23a) (180 mg, 0.33 mmol) in methanol (10 mL) was hydrogenated over 5% Pd/C (0.1 g) at 30° C. at 1 atm H$_2$ pressure. The reaction mixture was filtered through a pad of diatomaceous earth and the filtrate was concentrated to give the title compound 23b. Mass Spectrum (LCMS, ESI pos.): Calcd. for $C_{29}H_{30}F_4N_2O_4$: 547.2 (M+H)$^+$; found: 547.2.

C. (3S)-3-cyclopropyl-3-(3-((5-(2-fluoro-5-methoxyphenyl)-6-(1,1,1-trifluoropropan-2-yl)pyrazin-2-yl)methoxy)phenyl)propanoic acid, Cpd 40

The title compound 40 was prepared from (3S)-ethyl-3-cyclopropyl-3-(3-((5-(2-fluoro-5-methoxyphenyl)-6-(1,1,1-trifluoropropan-2-yl)pyrazin-2-yl)methoxy)phenyl)propanoate (23b) following the procedure described in Example 2, Step H. $^1$H-NMR (300 MHz, DMSO-d$_6$) δ (ppm): 8.84 (s, 1H), 7.19-7.27 (m, 2H), 7.10-7.15 (m, 1H), 6.98-7.00 (m, 2H), 6.89-6.95 (m, 2H), 5.36 (s, 2H), 3.84 (s, 3H), 3.77-3.83 (m, 1H), 2.64-2.69 (m, 2H), 2.39-2.42 (m, 1H), 1.59 (d, J=6.9 Hz, 3H), 0.87-1.03 (m, 1H), 0.54-0.57 (m, 1H), 0.29-0.39 (m, 2H), 0.12-0.14 (m, 1H). Mass Spectrum (LCMS, ESI pos.): Calcd. for $C_{27}H_{26}F_4N_2O_4$: 519.2 (M+H)$^+$; found: 519.2.

Example 24

(3S)-3-Cyclopropyl-3-(3-((5-(2-fluoro-5-methoxyphenyl)-6-(piperidin-1-yl)pyrazin-2-yl)methoxy)phenyl)propanoic acid (Cpd. 22)

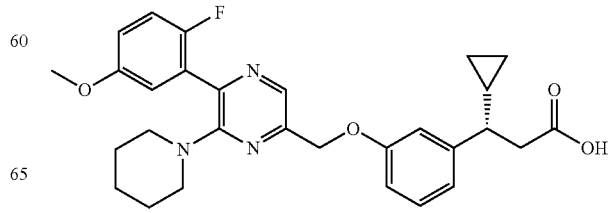

A. (3S)-Ethyl 3-cyclopropyl-3-(3-((5-(2-fluoro-5-methoxyphenyl)-6-(piperidin-1-yl)pyrazin-2-yl)methoxy)phenyl)propanoate, 24a

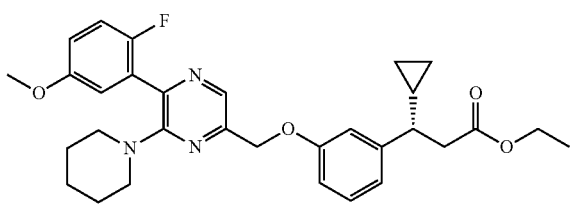

A solution of compound 1g (150 mg, 0.31 mmol), piperidine (263 mg, 3.09 mmol) in DMF (0.4 mL) was stirred overnight at 120° C. in a sealed tube. The reaction mixture was allowed to cool to RT and was treated with saturated aqueous NH₄Cl (10 mL). The resulting solution was extracted with EtOAc (3×10 mL). The organic layers were combined and concentrated. The residue obtained was purified by column chromatography on silica gel (EtOAc/petroleum ether (1:3 v/v)) to give the title compound 24a. Mass Spectrum (LCMS, ESI pos.): Calcd. for $C_{31}H_{36}FN_3O_4$: 534.3 (M+H)⁺; found: 534.3.

B. (3S)-3-Cyclopropyl-3-(3-((5-(2-fluoro-5-methoxyphenyl)-6-(piperidin-1-yl)pyrazin-2-yl)methoxy)phenyl)propanoic acid, Cpd 22

The title compound 22 was prepared from (3S)-3-cyclopropyl-3-(3-[[5-(2-fluoro-5-methoxyphenyl)-6-(piperidin-1-yl)pyrazin-2-yl]methoxy]phenyl)propanoate (24a) following the procedure described in Example 21, Step B. ¹H-NMR (300 MHz, DMSO-d₆) δ (ppm): 8.23 (s, 1H), 7.12-7.28 (m, 3H), 6.85-7.04 (m, 4H), 5.12 (s, 2H), 3.78 (s, 3H), 3.13-3.15 (m, 4H), 2.62-2.66 (m, 2H), 2.25-2.31 (m, 1H), 1.39-1.48 (m, 6H), 0.98-1.02 (m, 1H), 0.48-0.52 (m, 1H), 0.22-0.32 (m, 2H), 0.09-0.14 (m, 1H). Mass Spectrum (LCMS, ESI pos.): Calcd. for $C_{29}H_{32}FN_3O_4$: 506.2 (M+H)⁺; found: 506.1.

Example 25

(3S)-3-Cyclopropyl-3-(3-((5-(2-fluoro-5-methoxyphenyl)-6-(isopropyl(methyl)amino)pyrazin-2-yl)methoxy)phenyl)propanoic acid (Cpd. 34)

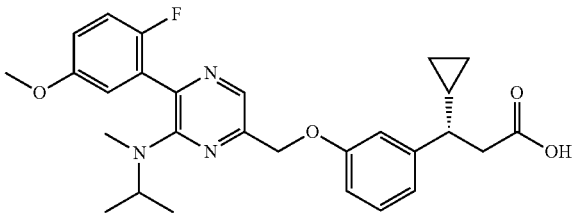 [SMILES: COc1ccc(F)c(-c2ncc(COc3cccc([C@@H](CC(=O)O)C4CC4)c3)nc2N(C)C(C)C)c1]

The title compound was prepared from a mixture of (3S)-ethyl 3-cyclopropyl-3-(3-((6-(dimethylamino)-5-(2-fluoro-5-methoxyphenyl)pyrazin-2-yl)methoxy)phenyl)propanoate (21a) and (3S)-ethyl 3-cyclopropyl-3-(3-[[5-(2-fluoro-5-methoxyphenyl)-6-[methyl(propan-2-yl)amino] pyrazin-2-yl]methoxy]phenyl)propanoate (21b) (as prepared in Example 21, Step A) following the procedure described in Example 21, Step B. ¹H-NMR (300 MHz, DMSO-d₆) δ (ppm): 12.00 (br, 1H), 8.15 (s, 1H), 7.10-7.24 (m, 3H), 6.85-7.02 (m, 4H), 5.12 (s, 2H), 4.28-4.33 (m, 1H), 3.77 (s, 3H), 2.62-2.66 (m, 2H), 2.51 (s, 3H), 2.24-2.30 (m, 1H), 1.01-1.03 (m, 7H), 0.47-0.50 (m, 1H), 0.11-0.30 (m, 2H), 0.03-0.09 (m, 1H). Mass Spectrum (LCMS, ESI pos.): Calcd. for $C_{28}H_{32}FN_3O_4$: 494.2 (M+H)⁺; found: 494.2.

Example 26

(3S)-3-Cyclopropyl-3-(3-((5-(2-fluoro-5-methoxyphenyl)-6-(3-methylthiophen-2-yl)pyrazin-2-yl)methoxy)phenyl)propanoic acid (Cpd. 38)

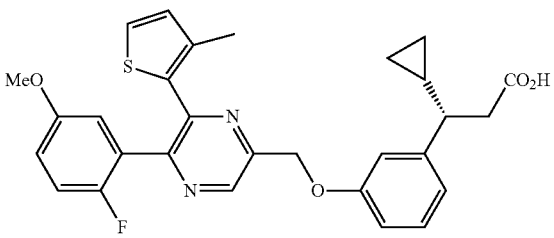 [SMILES: COc1ccc(F)c(-c2ncc(COc3cccc([C@@H](CC(=O)O)C4CC4)c3)nc2-c2sccc2C)c1]

The title compound was prepared from compound 1g and (3-methylthiophen-2-yl)boronic acid following the procedure described in Example 2, Steps G-H. ¹H-NMR (300 MHz, DMSO-d₆) δ (ppm): 8.88 (s, 1H), 7.55 (d, J=5.1 Hz, 1H), 7.23 (t, J=7.8 Hz, 1H), 7.08-7.14 (m, 1H), 6.84-7.01 (m, 6H), 5.35 (s, 2H), 3.69 (s, 3H), 2.61-2.63 (m, 2H), 2.24-2.32 (m, 1H), 1.87 (s, 3H), 0.85-0.99 (m, 1H), 0.44-0.49 (m, 1H), 0.21-0.29 (m, 2H), 0.08-0.11 (m, 1H). Mass Spectrum (LCMS, ESI pos.): Calcd. for $C_{29}H_{27}FN_2O_4S$: 519.2 (M+H)⁺; found: 519.2.

Example 27

(3S)-3-cyclopropyl-3-(3-((5-(2-fluoro-5-methoxyphenyl)-6-(5-methylthiophen-2-yl)pyrazin-2-yl)methoxy)phenyl)propanoic acid (Cpd. 39)

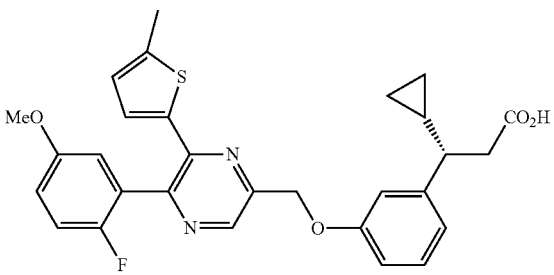 [SMILES: COc1ccc(F)c(-c2ncc(COc3cccc([C@@H](CC(=O)O)C4CC4)c3)nc2-c2ccc(C)s2)c1]

The title compound was prepared from compound 1g and (3-methylthiophen-2-yl)boronic acid following the procedure described in Example 2, Steps G-H. ¹H-NMR (300 MHz, DMSO-d₆) δ (ppm): 12.00 (br, 1H), 8.73 (s, 1H), 7.21-7.29 (m, 2H), 7.11-7.16 (m, 2H), 6.88-7.03 (m, 3H), 6.68-6.69 (m, 1H), 6.59 (d, J=3.6 Hz, 1H), 5.30 (s, 2H), 3.78 (s, 3H), 2.63-2.67 (m, 2H), 2.32 (s, 3H), 2.27-2.30 (m, 1H), 0.99-1.02 (m, 1H), 0.47-0.50 (m, 1H), 0.22-0.31 (m, 2H), 0.07-0.12 (m, 1H). Mass Spectrum (LCMS, ESI pos.): Calcd. for $C_{29}H_{27}FN_2O_4S$: 519.2 (M+H)⁺; found: 519.2.

Example 28

(3S)-3-Cyclopropyl-3-(3-((5-(2-fluoro-5-methoxy-phenyl)-6-isobutoxypyrazin-2-yl)methoxy)phenyl)propanoic acid (Cpd. 14)

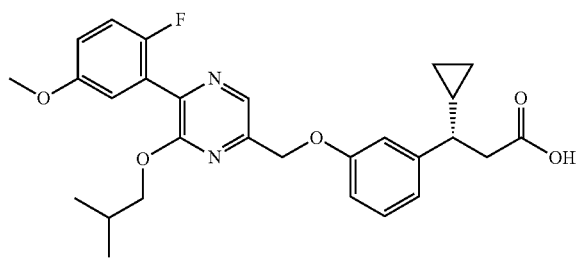 [SMILES: COc1ccc(F)c(-c2ncc(COc3cccc([C@@H](CC(=O)O)C4CC4)c3)nc2OCC(C)C)c1]

The title compound was prepared from compound 1g and 2-methylpropan-1-ol following an adaptation of the procedure described in Example 1, Step H, using neat alcohol as the solvent. $^1$H-NMR (400 MHz, DMSO-$d_6$) δ (ppm): 8.45 (s, 1H), 7.21-7.27 (m, 2H), 7.05-7.08 (m, 2H), 6.87-6.99 (m, 3H), 5.20 (s, 2H), 4.11 (d, J=6.4 Hz, 2H), 3.77 (s, 3H), 2.64-2.67 (m, 2H), 2.26-2.30 (m, 1H), 1.95-1.98 (m, 1H), 0.99-1.01 (m, 1H), 0.90 (d, J=6.8 Hz, 6H), 0.48-0.51 (m, 1H), 0.22-0.32 (m, 2H), 0.09-0.13 (m, 1H). Mass Spectrum (LCMS, ESI pos.): Calcd. for $C_{28}H_{31}FN_2O_5$: 495.2 (M+H)$^+$; found: 495.2.

Example 29

(S)-3-Cyclopropyl-3-(3-((6-(5,5-dimethylcyclopent-1-enyl)-5-(2-methoxypyridin-4-yl)pyrazin-2-yl)methoxy)phenyl)propanoic acid (Cpd. 31)

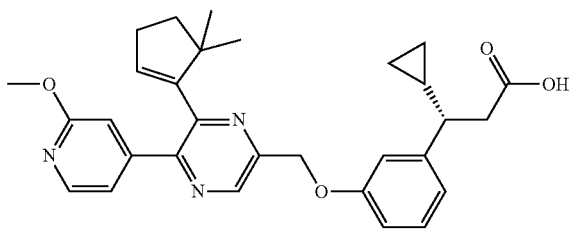 [SMILES: COc1cc(-c2ncc(COc3cccc([C@@H](CC(=O)O)C4CC4)c3)nc2C2=CCCC2(C)C)ccn1]

A. (S)-Ethyl 3-cyclopropyl-3-(3-((6-(5,5-dimethyl-cyclopent-1-enyl)-5-(2-methoxypyridin-4-yl)pyrazin-2-yl)methoxy)phenyl)propanoate, 29a

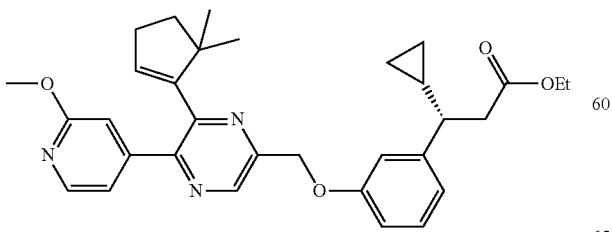

A mixture of ethyl (3S)-3-(3-[[5-chloro-6-(5,5-dimethyl-cyclopent-1-en-1-yl)pyrazin-2-yl]methoxy]phenyl)-3-cyclopropylpropanoate (30f) (100 mg, 0.200 mmol), (2-methoxypyridin-4-yl)boronic acid (60.0 mg, 0.390 mmol), Pd(dppf)Cl$_2$ (8.00 mg, 0.0100 mmol) and Cs$_2$CO$_3$ (179 mg, 0.550 mmol) in dioxane (0.8 mL), and water (0.2 mL) was stirred for 2 h at 90° C. under N$_2$. The reaction mixture was allowed to cool to room temperature and treated with 15 mL of water. The resulting solution was extracted with EtOAc (3×10 mL). The organic layers were combined, dried (Na$_2$SO$_4$) and concentrated. The residue was purified by column chromatography on silica gel (EtOAc/petroleum ether (1:100-1:10 v/v)) to give the title compound 29a. Mass Spectrum (LCMS, ESI pos.): Calcd. for $C_{32}H_{37}N_3O_4$: 528.3 (M+H)$^+$; found: 528.2.

B. (S)-3-Cyclopropyl-3-(3-((6-(5,5-dimethylcyclopent-1-enyl)-5-(2-methoxypyridin-4-yl)pyrazin-2-yl)methoxy)phenyl)propanoic acid, Cpd 31

The title compound was prepared from (3S)-3-cyclopropyl-3-(3-[[6-(5,5-dimethylcyclopent-1-en-1-yl)-5-(2-methoxypyridin-4-yl)pyrazin-2-yl]methoxy]phenyl)propanoate (29a) following the procedure described in Example 2, Step H. $^1$H-NMR (400 MHz, DMSO-$d_6$) δ (ppm): 8.72 (s, 1H), 8.22 (s, 1H), 7.21 (t, J=8.0 Hz, 1H), 7.08-7.09 (m, 1H), 6.86-6.96 (m, 4H), 5.50 (s, 1H), 5.30 (s, 2H), 3.86 (s, 3H), 2.58-2.69 (m, 2H), 2.22-2.33 (m, 3H), 1.73-1.76 (m, 2H), 1.23 (s, 6H), 0.90-1.05 (m, 1H), 0.44-0.54 (m, 1H), 0.21-0.27 (m, 2H), 0.08-0.09 (m, 1H). Mass Spectrum (LCMS, ESI neg.): Calcd. for $C_{30}H_{33}N_3O_4$: 498.2 (M−H)$^−$; found: 498.1.

Example 30

(3S)-3-Cyclopropyl-3-(3-((6-(5,5-dimethylcyclopent-1-enyl)-5-(5-fluoro-2-methoxypyridin-4-yl)pyrazin-2-yl)methoxy)phenyl)propanoic acid (Cpd. 15)

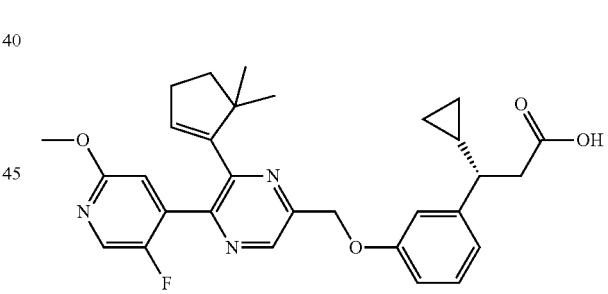

A. 5-Bromo-3-(5,5-dimethylcyclopent-1-enyl)pyrazin-2-amine, 30a

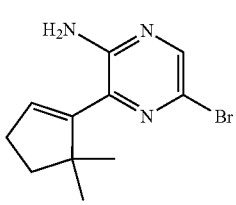

A mixture of 3,5-dibromopyrazin-2-amine (15.0 g, 59.3 mmol), 2-(5,5-dimethylcyclopent-1-en-1-yl)-4,4,5,5-tetramethyl-1,3,2-dioxaborolane (15.0 g, 67.5 mmol), Pd(dppf)Cl$_2$ (2.21 g, 3.02 mmol) and Cs₂CO₃ (37.6 g, 115 mmol) in water (16 mL) and 1,4-dioxane (64 mL) was stirred overnight at 90° C. under N₂. The reaction mixture was allowed to cool to room temperature and treated with 300 mL of water. The resulting solution was extracted with EtOAc (3×300 mL). The organic layers were combined and concentrated. The residue obtained was purified by column chromatography on silica gel (EtOAc/petroleum ether 1:4 v/v) to give the title compound 30a. Mass Spectrum (LCMS, ESI pos.): Calcd. for $C_{11}H_{14}BrN_3$: 268.0 (M+H)⁺; found: 268.0.

B. Methyl 5-amino-6-(5,5-dimethylcyclopent-1-enyl)pyrazine-2-carboxylate, 30b

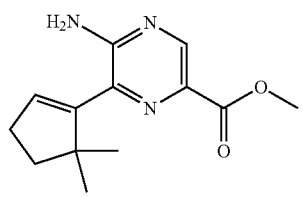

30b

A mixture of 5-bromo-3-(5,5-dimethylcyclopent-1-en-1-yl)pyrazin-2-amine (30a) (24.0 g, 89.5 mmol), Pd(dppf)Cl₂ (3.25 g, 4.44 mmol) and triethylamine (18.0 g, 178 mmol) in methanol (500 mL) was stirred overnight at 110° C. under a $CO_{(g)}$ (60 atm) atmosphere. The resulting mixture was allowed to cool to room temperature and concentrated. The residue obtained was purified by column chromatography on silica gel (EtOAc/petroleum ether 1:5-1:3 v/v) to give title compound 30b. Mass Spectrum (LCMS, ESI pos.): Calcd. for $C_{13}H_{17}N_3O_2$: 248.1 (M+H)⁺; found: 248.1.

C. (5-Amino-6-(5,5-dimethylcyclopent-1-enyl)pyrazin-2-yl)methanol, 30c

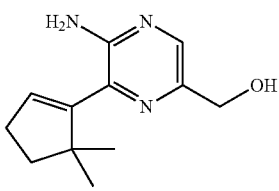

30c

The title compound was prepared from 5-amino-6-(5,5-dimethylcyclopent-1-en-1-yl)pyrazine-2-carboxylate (30b) following the procedure described in Example 14, Step B. Mass Spectrum (LCMS, ESI pos.): Calcd. for $C_{12}H_{17}N_3O$: 220.1 (M+H)⁺; found: 220.1.

D. (6-(5,5-Dimethylcyclopent-1-enyl)-5-iodopyrazin-2-yl)methanol, 30d

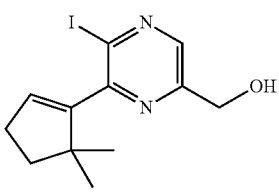

30d

To a mixture of [5-amino-6-(5,5-dimethylcyclopent-1-en-1-yl)pyrazin-2-yl]methanol (30c) (5.90 g, 26.9 mmol) and I₂ (8.00 g, 31.5 mmol) in CH₂I₂ (20 mL), t-BuONO (11.0 g, 106 mmol) was added. The resulting solution was stirred overnight at room temperature and treated with 10% aq. Na₂S₂O₃ (50 mL). The resulting solution was extracted with dichloromethane (3×50 mL). The organic layers were combined and concentrated. The residue obtained was purified by column chromatography on silica gel (EtOAc/petroleum ether (1:3 v/v)) to give the title compound 30d. Mass Spectrum (LCMS, ESI pos.): Calcd. for $C_{12}H_{15}IN_2O$: 331.0 (M+H)⁺; found: 331.0.

E. 2-Chloro-5-(chloromethyl)-3-(5,5-dimethylcyclopent-1-enyl)pyrazine, 30e

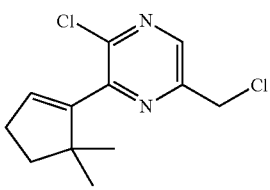

30e

To a solution of [6-(5,5-dimethylcyclopent-1-en-1-yl)-5-iodopyrazin-2-yl]methanol (30d) (2.8 g, 8.5 mmol) in dichloromethane (50 mL), and N,N-dimethylformamide (0.5 mL), thionyl chloride (2.0 g, 17 mmol) was added dropwise with stirring at 0° C. The resulting solution was stirred for 30 min at room temperature. The reaction was then quenched by the addition of 50 mL of saturated NaHCO₃. The resulting solution was extracted with dichloromethane (3×100 mL). The organic layers were combined and concentrated to give the title compound 30e.

F. (S)-Ethyl 3-(3-((5-chloro-6-(5,5-dimethylcyclopent-1-enyl)pyrazin-2-yl)methoxy)phenyl)-3-cyclopropylpropanoate, 30f

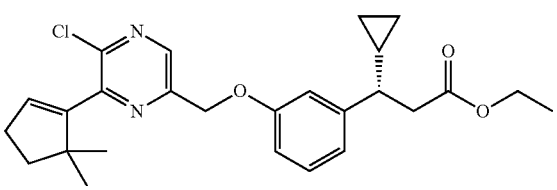

30f

The title compound 30f was prepared from 2-chloro-5-(chloromethyl)-3-(5,5-dimethylcyclopent-1-en-1-yl)pyrazine (30e) and ethyl (3S)-3-cyclopropyl-3-(3-hydroxyphenyl)propanoate (1f) (as prepared in the Example 1, Step F) following the procedure described in Example 1, Step G. Mass Spectrum (LCMS, ESI pos.): Calcd. for $C_{26}H_{31}ClN_2O_3$: 455.2 (M+H)⁺; found: 455.2.

G. (3S)-Ethyl 3-cyclopropyl-3-(3-((6-(5,5-dimethyl-cyclopent-1-enyl)-5-(5-fluoro-2-methoxypyridin-4-yl)pyrazin-2-yl)methoxy)phenyl)propanoate, 30g

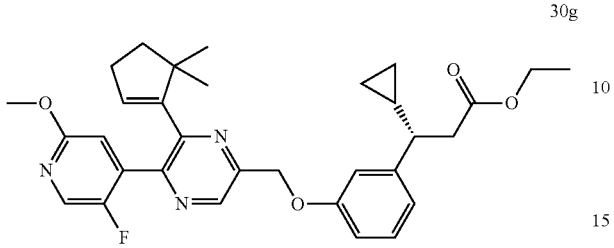

30g

The title compound 30g was prepared from methyl (S)-ethyl 3-(3-((5-chloro-6-(5,5-dimethylcyclopent-1-enyl)pyrazin-2-yl)methoxy)phenyl)-3-cyclopropylpropanoate (30f) (71 mg, 0.16 mmol), and (5-fluoro-2-methoxypyridin-4-yl)boronic acid following the procedure described in Example 2, Step G. Mass Spectrum (LCMS, ESI pos.): Calcd. for $C_{32}H_{36}FN_3O_4$: 546.3 $(M+H)^+$; found: 546.3.

H. (3S)-3-Cyclopropyl-3-(3-((6-(5,5-dimethylcyclopent-1-enyl)-5-(5-fluoro-2-methoxypyridin-4-yl)pyrazin-2-yl)methoxy)phenyl)propanoic acid, Cpd 15

The title compound 15 was prepared from (3S)-ethyl 3-cyclopropyl-3-(3-((6-(5,5-dimethylcyclopent-1-enyl)-5-(5-fluoro-2-methoxypyridin-4-yl)pyrazin-2-yl)methoxy)phenyl)propanoate (30g) following the procedure described in Example 2, Step H. $^1$H-NMR (300 MHz, DMSO-$d_6$) δ (ppm): 8.76 (s, 1H), 8.19 (s, 1H), 7.18 (t, J=7.8 Hz, 1H), 7.04 (d, J=4.8 Hz, 1H), 6.89-6.94 (m, 1H), 6.84-6.87 (m, 2H), 5.55 (s, 1H), 5.31 (s, 2H), 3.88 (s, 3H), 2.49-2.55 (m, 2H), 2.17-2.34 (m, 3H), 1.69-1.79 (m, 2H), 1.23-1.31 (m, 6H), 0.85-0.96 (m, 1H), 0.40-0.46 (m, 1H), 0.20-0.29 (m, 2H), 0.02-0.07 (m, 1H). Mass Spectrum (LCMS, ESI pos.): Calcd. for $C_{30}H_{32}FN_3O_4$: 518.2 $(M+H)^+$; found: 518.2.

Example 31

(S)-3-Cyclopropyl-3-(3-((6-(5,5-dimethylcyclopent-1-enyl)-5-(3-methoxyphenyl)pyrazin-2-yl)methoxy)phenyl)propanoic acid (Cpd. 35)

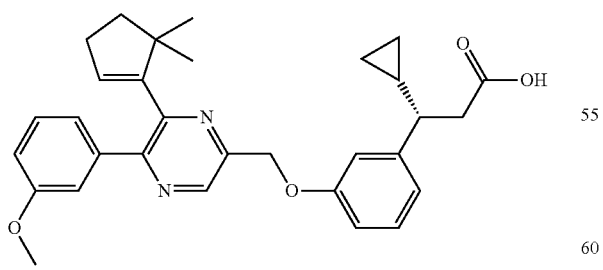

The title compound 35 was prepared from ethyl (3S)-3-(3-[[5-chloro-6-(5,5-dimethylcyclopent-1-en-1-yl)pyrazin-2-yl]methoxy]phenyl)-3-cyclopropylpropanoate (30f), and (3-methoxyphenyl)boronic acid following the procedure described in Example 30, Steps G-H. $^1$H-NMR (400 MHz, DMSO-$d_6$) δ (ppm): 8.67 (s, 1H), 7.34 (t, J=8.0 Hz, 1H), 7.20 (t, J=8.0 Hz, 1H), 7.08-7.11 (m, 2H), 6.87-6.95 (m, 4H), 5.49 (s, 1H), 5.27 (s, 2H), 3.81 (s, 3H), 2.62-2.66 (m, 2H), 2.19-2.32 (m, 3H), 1.73 (t, J=6.8 Hz, 1H), 1.28 (s, 6H), 0.98 (s, 1H), 0.48 (s, 1H), 0.22-0.28 (m, 2H), 0.10 (s, 1H). Mass spectrum (LCMS, ESI pos): Calcd. for $C_{31}H_{34}N_2O_4$: 499.3 $(M+H)^+$; found: 499.1.

Example 32

(3S)-3-Cyclopropyl-3-(3-((6-(5,5-dimethylcyclopent-1-enyl)-5-(2-fluoro-5-methoxyphenyl)pyrazin-2-yl)methoxy)phenyl)propanoic acid (Cpd. 30)

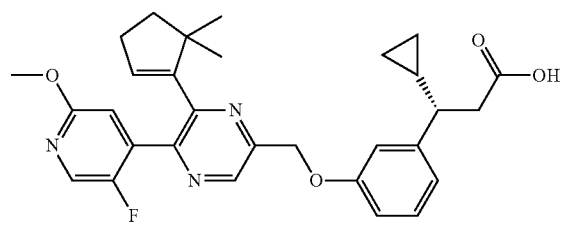 [SMILES: COc1cc(-c2ncc(COc3cccc([C@@H](CC(=O)O)C4CC4)c3)nc2C2=CCCC2(C)C)c(F)cn1]

A. 5-(Chloromethyl)-3-(5,5-dimethylcyclopent-1-enyl)-2-iodopyrazine, 32a

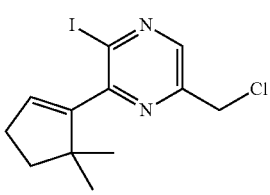

32a

To a solution of [6-(5,5-dimethylcyclopent-1-en-1-yl)-5-iodopyrazin-2-yl]methanol (30d) (700.0 mg, 2.12 mmol) in dichloromethane (20 mL) and DMF (2 mL) was added thionyl chloride (504 mg, 4.24 mmol). The resulting solution was stirred for 30 min at 0° C. and concentrated. The obtained residue was purified by column chromatography on silica gel (EtOAc/petroleum ether (1:5 v/v)) to give the title compound 32a. Mass Spectrum (LCMS, ESI pos.): Calcd. for $C_{12}H_{14}ClIN_2$: 349.0 $(M+H)^+$; found: 348.9.

B. (S)-Ethyl 3-cyclopropyl-3-(3-((6-(5,5-dimethylcyclopent-1-enyl)-5-iodopyrazin-2-yl)methoxy)phenyl)propanoate, 32b

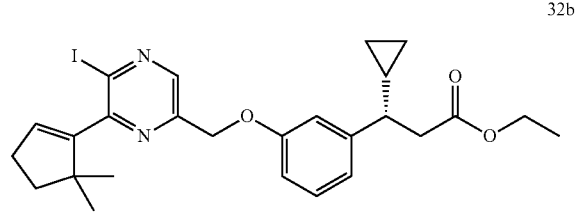 [SMILES: CCOC(=O)C[C@H](c1cccc(OCc2cnc(I)c(C3=CCCC3(C)C)n2)c1)C1CC1]

32b

The title compound 32b was prepared from 5-(chloromethyl)-3-(5,5-dimethylcyclopent-1-en-1-yl)-2-iodopyrazine (32a) and (S)-ethyl 3-cyclopropyl-3-(3-hydroxyphenyl)propanoate (1f), following the procedure described in Example 1, Step G. Mass Spectrum (LCMS, ESI pos.): Calcd. for $C_{26}H_{31}IN_2O_3$: 547.1 (M+H)$^+$; found: 547.2.

C. (3S)-Ethyl 3-cyclopropyl-3-(3-((6-(5,5-dimethyl-cyclopent-1-enyl)-5-(2-fluoro-5-methoxyphenyl)pyrazin-2-yl)methoxy)phenyl)propanoate, 32c

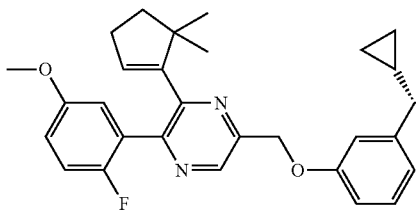

32c

The title compound was prepared from (S)-ethyl 3-cyclopropyl-3-(3-((6-(5,5-dimethylcyclopent-1-enyl)-5-iodopyrazin-2-yl)methoxy)phenyl)propanoate (32b) and (2-fluoro-5-methoxyphenyl)boronic acid, following the procedure described in Example 2, Step G. Mass Spectrum (LCMS, ESI pos.): Calcd. for $C_{33}H_{37}FN_2O_4$: 545.3 (M+H)$^+$; found: 545.3.

D. (3S)-3-Cyclopropyl-3-(3-((6-(5,5-dimethylcyclopent-1-enyl)-5-(2-fluoro-5-methoxyphenyl)pyrazin-2-yl)methoxy)phenyl)propanoate, Cpd 30

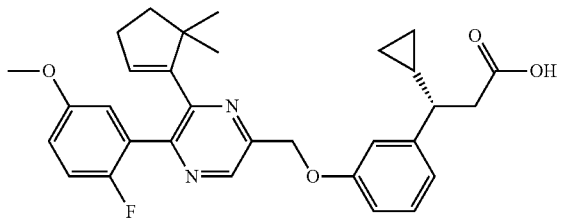 [SMILES: COc1ccc(F)c(-c2ncc(COc3cccc([C@@H](CC(=O)O)C4CC4)c3)nc2C2=CCCC2(C)C)c1]

To a solution of (3S)-ethyl 3-cyclopropyl-3-(3-((6-(5,5-dimethylcyclopent-1-enyl)-5-(2-fluoro-5-methoxyphenyl)pyrazin-2-yl)methoxy)phenyl)propanoate (32c) (360 mg, 0.66 mmol) in THF (5 mL), a solution of sodium hydroxide (265 mg, 6.62 mmol) in water (3 mL) and ethanol (1 mL) were added. The resulting solution was stirred overnight at RT. The resulting mixture was concentrated to remove most of the organic solvent. The pH value of the solution was adjusted to 3-4 with 1 N HCl. The solids formed were collected by filtration, dried under reduced pressure to give the title compound 30. $^1$H-NMR (300 MHz, DMSO-d$_6$) δ (ppm): 12.06 (br, 1H), 8.70 (s, 1H), 7.13-7.20 (m, 2H), 6.94-7.00 (m, 2H), 6.84-6.89 (m, 3H), 5.45 (s, 1H), 5.28 (s, 2H), 3.76 (s, 3H), 2.39-2.49 (m, 2H), 2.20-2.35 (m, 1H), 2.14-2.18 (m, 2H), 1.69 (t, J=6.9 Hz, 2H), 1.24 (s, 6H), 0.92-0.95 (m, 1H), 0.39-0.45 (m, 1H), 0.21-0.25 (m, 2H), 0.03-0.06 (m, 1H). Mass Spectrum (LCMS, ESI pos.): Calcd. for $C_{31}H_{33}FN_2O_4$: 517.2 (M+H)$^+$; found: 517.2.

Example 33

(3S)-3-cyclopropyl-3-(3-((5-(2-fluoro-5-methoxyphenyl)-6-isopropylpyrazin-2-yl)methoxy)phenyl)propanoic acid (Cpd. 37)

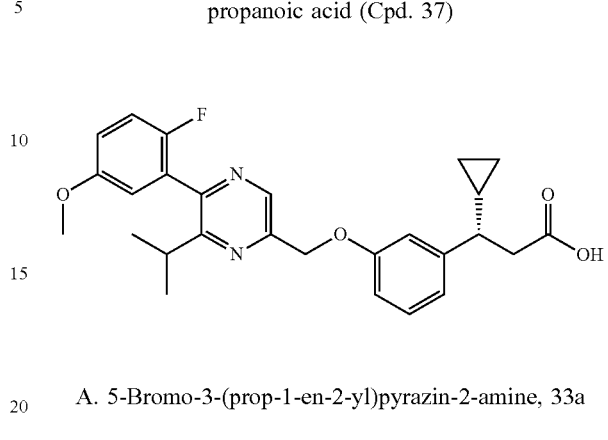

A. 5-Bromo-3-(prop-1-en-2-yl)pyrazin-2-amine, 33a

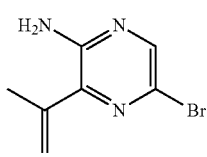

33a

A mixture of 3,5-dibromopyrazin-2-amine (6.5 g, 26 mmol), 4,4,5,5-tetramethyl-2-(prop-1-en-2-yl)-1,3,2-dioxaborolane (4.8 g, 28 mmol), Pd(dppf)Cl$_2$ (1.0 g, 1.2 mmol), Cs$_2$CO$_3$ (20 g, 63 mmol) in dioxane (60 mL) and water (15 mL) was stirred overnight at 85° C. under N$_2$. The reaction was allowed to cool to RT and then quenched by the addition of 50 mL of saturated aqueous NH$_4$Cl (aq). The resulting solution was extracted with EtOAc (3×100 mL). The organic layers were combined, dried (Na$_2$SO$_4$) and concentrated. The residue obtained was purified by flash column chromatography (EtOAc/petroleum ether 1:9, v/v) on silica gel to obtain the title compound 33a. Mass Spectrum (LCMS, ESI pos.): Calcd. for $C_7H_8BrN_3$: 214.0 (M+H)$^+$; found: 214.1.

B. Methyl 5-amino-6-(prop-1-en-2-yl)pyrazine-2-carboxylate, 33b

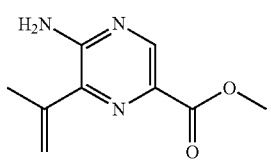

33b

A mixture of 5-bromo-3-(prop-1-en-2-yl)pyrazin-2-amine (33a) (5.6 g, 26 mmol), Pd(dppf)Cl$_2$ (1.07 g, 1.31 mmol) and triethylamine (5.2 g, 51 mmol) in methanol (60 mL) was stirred overnight at 110° C. under a CO$_{(g)}$ (60 atm) atmosphere. The resulting mixture was allowed to cool to RT, depressurized and concentrated. The residue obtained was purified by flash column chromatography (EtOAc/petroleum ether 2:8, v/v) on silica gel to obtain the title compound 33b as a light yellow solid. Mass Spectrum (LCMS, ESI pos.): Calcd. for $C_9H_{11}N_3O_2$: 194.1 (M+H)$^+$; found: 194.1.

C. Methyl 5-amino-6-isopropylpyrazine-2-carboxylate, 33c

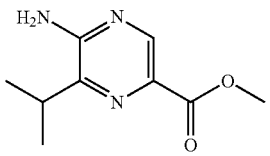

A mixture of methyl 5-amino-6-(prop-1-en-2-yl)pyrazine-2-carboxylate (33b) (1.7 g, 8.8 mmol) and 10% Pd/C (1.7 g) in methanol (20 mL) and ethyl acetate (20 mL) was stirred overnight at room temperature under a $H_2$ (3 atm) atmosphere. The reaction mixture was filtered through a pad of diatomaceous earth and the filtrate was concentrated. The residue obtained was purified by flash column chromatography (EtOAc/petroleum ether, 2:8, v/v) on silica gel to obtain the title compound 33c as a yellow solid. Mass Spectrum (LCMS, ESI pos.): Calcd. for $C_9H_{13}N_3O_2$: 196.1 $(M+H)^+$; found: 196.1.

D. Methyl 5-bromo-6-isopropylpyrazine-2-carboxylate, 33d

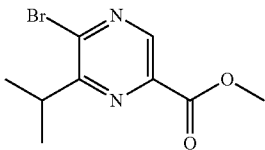

To a mixture of t-BuONO (526 mg, 5.11 mmol) and $CuBr_2$ (1.14 g, 5.10 mmol) in $CH_3CN$ (5 mL) was added a solution of methyl 5-amino-6-(propan-2-yl)pyrazine-2-carboxylate (33c) (500 mg, 2.56 mmol) in $CH_3CN$ (2 mL) at 0° C. The resulting mixture was stirred overnight at room temperature. The reaction was then quenched by the addition of 10 mL of saturated $NH_4Cl$ (aq). The resulting solution was extracted with EtOAc (3×20 mL). The organic layers were combined and concentrated. The residue obtained was purified by flash column chromatography (EtOAc/petroleum ether 6:94, v/v) on silica gel to obtain the title compound 33d. Mass Spectrum (LCMS, ESI pos.): Calcd. for $C_9H_{11}BrN_2O_2$: 259.0 $(M+H)^+$; found: 259.0.

E. Methyl 5-(2-fluoro-5-methoxyphenyl)-6-isopropylpyrazine-2-carboxylate, 33e

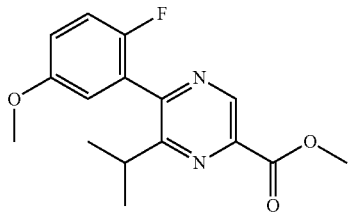

A mixture of methyl 5-bromo-6-(propan-2-yl)pyrazine-2-carboxylate (33d) (300 mg, 1.16 mmol), (2-fluoro-5-methoxyphenyl)boronic acid (345 mg, 2.03 mmol), Pd(dppf)Cl$_2$ (78 mg, 0.07 mmol) and potassium carbonate (466 mg, 3.38 mmol) in N,N-dimethylformamide (2 mL) was stirred for 4 h at 90° C. under $N_2$ in a sealed tube. The reaction mixture was allowed to cool to RT and quenched by the addition of 5 mL of saturated $NH_4Cl$ (aq). The resulting solution was extracted with EtOAc (3×10 mL). The organic layers were combined and concentrated. The residue obtained was purified by flash column chromatography (EtOAc/petroleum ether 1:9 v/v) on silica gel to obtain the title compound 33e. Mass Spectrum (LCMS, ESI pos.): Calcd. for $C_{16}H_{17}FN_2O_3$: 305.1 $(M+H)^+$; found: 305.0.

F. (5-(2-Fluoro-5-methoxyphenyl)-6-isopropylpyrazin-2-yl)methanol, 33f

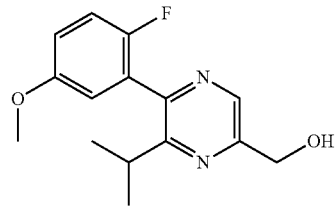

To a solution of methyl 5-(2-fluoro-5-methoxyphenyl)-6-(propan-2-yl)pyrazine-2-carboxylate (33e) (250 mg, 0.82 mmol) in tetrahydrofuran (5 mL), LAH (75 mg, 2.0 mmol) was added at 0° C. The resulting solution was stirred for 30 min at 0° C. and then treated with 1 g of $Na_2SO_4.10\ H_2O$. The reaction mixture was filtered and the filtrate was concentrated. The residue obtained was purified by flash column chromatography (EtOAc/petroleum ether 2:8 v/v) on silica gel to obtain the title compound 33f. Mass Spectrum (LCMS, ESI pos.): Calcd. for $C_{15}H_{17}FN_2O_2$: 277.1 $(M+H)^+$; found: 277.1.

G. 5-(Chloromethyl)-2-(2-fluoro-5-methoxyphenyl)-3-isopropylpyrazine, 33g

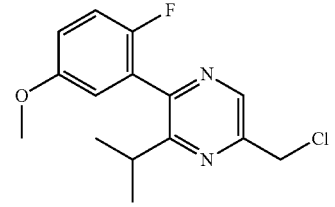

To a solution of [5-(2-fluoro-5-methoxyphenyl)-6-(propan-2-yl)pyrazin-2-yl]methanol (33f) (110 mg, 0.40 mmol) in dichloromethane (2 mL) and N,N-dimethylformamide (0.1 mL), thionyl chloride (95 mg, 0.80 mmol) was added at 0° C. The resulting solution was stirred for 1 h at room temperature. The reaction was then quenched by the addition of 5 mL of water. The resulting mixture was extracted with dichloromethane (3×10 mL). The organic layers were combined, dried ($Na_2SO_4$) and concentrated to obtain the title compound 33g as a light yellow oil. Mass Spectrum (LCMS, ESI pos.): Calcd. for $C_{15}H_{16}ClFN_2O$: 295.1 $(M+H)^+$; found: 295.1.

H. (3S)-Methyl 3-cyclopropyl-3-(3-((5-(2-fluoro-5-methoxyphenyl)-6-isopropylpyrazin-2-yl)methoxy)phenyl)propanoate, 33h

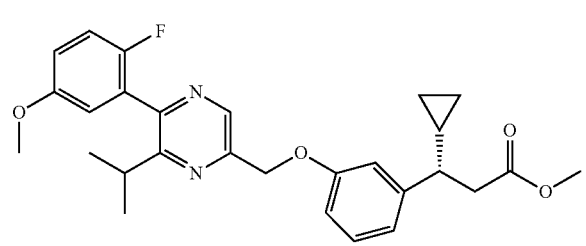

A mixture of 5-(chloromethyl)-2-(2-fluoro-5-methoxyphenyl)-3-(propan-2-yl)pyrazine (33g) (130 mg, 0.44 mmol), methyl (3S)-3-cyclopropyl-3-(3-hydroxyphenyl)propanoate (97 mg, 0.44 mmol) and Cs$_2$CO$_3$ (287 mg, 0.88 mmol) in CH$_3$CN (1 mL) was stirred overnight at 50° C. The reaction was allowed to cool to RT and quenched by the addition of 5 mL of water. The resulting solution was extracted with EtOAc (3×10 mL). The organic layers were combined and concentrated. The residue obtained was purified by flash column chromatography (EtOAc/petroleum ether 8:92 v/v) on silica gel to obtain the title compound 33h. Mass Spectrum (LCMS, ESI pos.): Calcd. for C$_{28}$H$_{31}$FN$_2$O$_4$: 479.2 (M+H)$^+$; found: 479.3.

I. (3S)-3-cyclopropyl-3-(3-((5-(2-fluoro-5-methoxyphenyl)-6-isopropylpyrazin-2-yl)methoxy)phenyl) propanoic acid, Cpd 37

The title compound 37 was prepared from (3S)-methyl 3-cyclopropyl-3-(3-((5-(2-fluoro-5-methoxyphenyl)-6-isopropylpyrazin-2-yl)methoxy)phenyl)propanoate (33h) following the procedure described in Example 2, Step H. $^1$H-NMR (300 MHz, DMSO-d$_6$) δ (ppm): 11.99 (br, 1H), 8.73 (s, 1H), 7.20-7.33 (m, 2H), 6.87-7.12 (m, 5H), 5.29 (s, 2H), 3.78 (s, 3H), 2.98-3.02 (m, 1H), 2.63-2.67 (m, 2H), 2.25-2.28 (m, 1H), 1.16 (d, J=6.6 Hz, 6H), 0.89-1.00 (m, 1H), 0.45-0.50 (m, 1H), 0.22-0.31 (m, 2H), 0.09-0.11 (s, 1H). Mass Spectrum (LCMS, ESI pos.): Calcd. for C$_{27}$H$_{29}$FN$_2$O$_4$: 465.2 (M+H)$^+$; found: 465.2.

Following the procedures described in Example 33 above, and substituting suitably selected reagents, starting materials and conditions as would be readily apparent to those skilled in the art, the following representative compound of the present invention was prepared.

Example 34

(3S)-3-Cyclopropyl-3-(3-((5-(2-fluoro-5-methoxyphenyl)-6-isopropoxypyrazin-2-yl)methoxy)phenyl) propanoate (Cpd. 29)

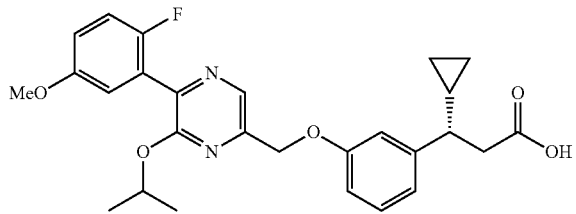 [SMILES: COc1ccc(F)c(-c2ncc(COc3cccc([C@@H](CC(=O)O)C4CC4)c3)nc2OC(C)C)c1]

To a solution of propan-2-ol (242 mg, 4.03 mmol) in tetrahydrofuran (4 mL), sodium hydride (8.7 mg, 0.36 mmol) was added. The resulting solution was stirred for 30 min at RT and treated with a solution of compound 1g (200 mg, 0.42 mmol) in tetrahydrofuran (1 mL). The resulting solution was stirred for 1 h at 75° C. The reaction mixture was allowed to cool to RT and quenched by the addition of 5 mL of saturated aqueous NH$_4$Cl solution. The resulting solution was extracted with EtOAc (3×5 mL). The organic layers were combined and washed with water (2×10 mL). The organic layer was concentrated. The residue obtained was purified by reverse phase Prep-HPLC using water and CH$_3$CN as the mobile phase to obtain the title compound 29. $^1$H-NMR (300 MHz, DMSO-d$_6$) δ (ppm): 8.42 (s, 1H),

| Cpd No. | Structure | Characterization |
|---|---|---|
| 5 | (structure) | (3S)-3-Cyclopropyl-3-(3-((5-(2-fluoro-5-methoxyphenyl)-6-isobutylpyrazin-2-yl)methoxy)phenyl)propanoic acid. $^1$H-NMR (300 MHz, DMSO-d$_6$) δ (ppm): 8.60 (s, 1H), 7.04-7.14 (m, 2H), 6.93-6.99 (m, 1H), 6.76-6.88 (m, 4H), 5.21 (s, 2H), 3.72 (s, 3H), 2.50-2.60 (m, 4H), 2.20-2.30 (m, 1H), 1.90-2.05 (m, 1H), 0.80-0.95 (m, 1H), 0.69 (s, 3H), 0.67 (s, 3H), 0.40-0.50 (m, 1H), 0.20-0.30 (m, 2H), −0.05-0.05 (m, 1H). Mass Spectrum (LCMS, ESI pos.): Calcd. for C$_{28}$H$_{31}$FN$_2$O$_4$: 479.2 (M + H)$^+$; found: 479.0. |

7.13-7.26 (m, 2H), 7.02-7.07 (m, 2H), 6.93 (s, 1H), 6.83-6.86 (m, 2H), 5.23-5.36 (m, 1H), 5.18 (s, 2H), 3.83 (s, 3H), 2.20-2.36 (m, 3H), 1.27 (d, J=6.3 Hz, 6H), 0.85-0.95 (m, 1H), 0.32-0.38 (m, 1H), 0.15-0.23 (m, 2H), 0.00-0.10 (m, 1H). Mass Spectrum (LCMS, ESI pos.): Calcd. for $C_{27}H_{29}FN_2O_5$: 481.2 $(M+H)^+$; found: 481.5.

Example 35

(3S)-3-Cyclopropyl-3-(3-((5-(2-fluoro-5-methoxyphenyl)-6-(5-methylthiophen-2-yl)pyrazin-2-yl)methoxy)phenyl)propanoic acid (Cpd. 36)

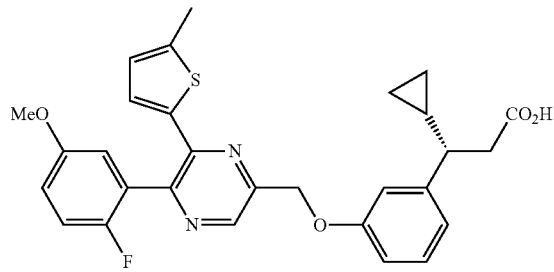 [SMILES: COc1ccc(F)c(-c2ncc(COc3cccc([C@@H](CC(=O)O)C4CC4)c3)nc2-c2ccc(C)s2)c1]

A. (3S)-Ethyl 3-cyclopropyl-3-(3-((5-(2-fluoro-5-methoxyphenyl)-6-(5-methylthiophen-2-yl)pyrazin-2-yl)methoxy)phenyl)propanoate, 35a

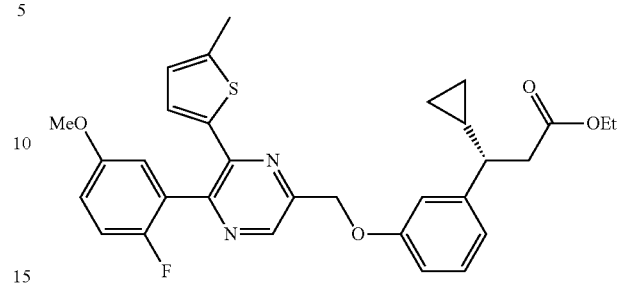

35a

A mixture of compound 1g (120 mg, 0.25 mmol), (5-methylthiophen-2-yl)boronic acid (52 mg, 0.37 mmol), Pd(dppf)Cl$_2$ (10 mg, 0.01 mmol) and Cs$_2$CO$_3$ (200 mg, 0.61 mmol) in 1,4-dioxane (2 mL) and water (0.6 mL) was stirred overnight at 85° C. under N$_2$. The reaction mixture was allowed to cool to RT and treated with 10 mL of water. The resulting solution was extracted with EtOAc (3×10 mL). The organic layers were combined and concentrated. The residue obtained was purified by flash column chromatography (EtOAc/petroleum ether 1:10 v/v) on silica gel to obtain the title compound 35a. Mass Spectrum (LCMS, ESI pos.): Calcd. for $C_{31}H_{31}FN_2O_4S$: 547.2 $(M+H)^+$; found: 547.2. Following the procedures described in example 35 above, and substituting suitably selected reagents, starting materials and conditions as would be readily apparent to those skilled in the art, the following representative compounds of the present invention were prepared.

| Cpd No. | Structure | Characterization |
|---|---|---|
| 23 | 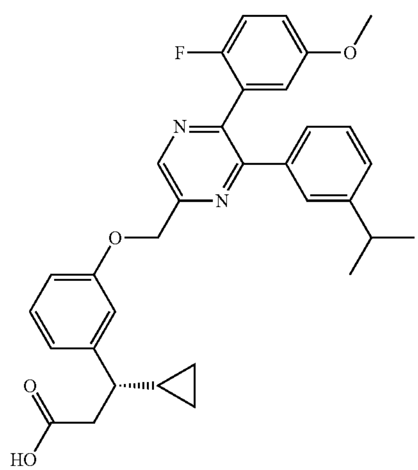 [SMILES: COc1ccc(F)c(-c2ncc(COc3cccc([C@@H](CC(=O)O)C4CC4)c3)nc2-c2cccc(C(C)C)c2)c1] | (3S)-3-Cyclopropyl-3-(3-((5-(2-fluoro-5-methoxyphenyl)-6-(3-isopropylphenyl)pyrazin-2-yl)methoxy)phenyl)propanoic acid $^1$H-NMR (300 MHz, DMSO-d6) δ (ppm): 12.03 (s, 1H), 8.88 (s, 1H), 7.21-7.37 (m, 6H), 6.87-7.07 (m, 4H), 5.37 (s, 2H), 3.77 (s, 3H), 2.64-2.79 (m, 3H), 2.25-2.28 (m, 1H), 1.00-1.03 (m, 7H), 0.47-0.49 (m, 1H), 0.21-0.29 (m, 2H), 0.09-1.12 (m, 1H). Mass Spectrum (LCMS, ESI pos.): Calcd. for $C_{33}H_{33}FN_2O_4$: 541.2 $(M + H)^+$; found: 541.6. |

| Cpd No. | Structure | Characterization |
|---|---|---|
| 43 | 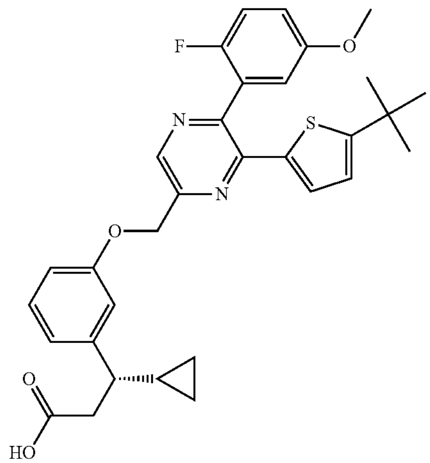 [SMILES: COc1ccc(F)c(-c2ncc(COc3cccc([C@@H](CC(=O)O)C4CC4)c3)nc2-c2ccc(C(C)(C)C)s2)c1] | (3S)-3-(3-((6-(5-tert-Butylthiophen-2-yl)-5-(2-fluoro-5-methoxyphenyl)pyrazin-2-yl)methoxy)phenyl)-3-cyclopropylpropanoic acid $^1$H-NMR (300 MHz, DMSO-d$_6$) δ (ppm): 8.79 (s, 1H), 7.30 (s, 1H), 7.15-7.26 (m, 2H), 7.08-7.10 (m, 2H), 7.03-7.06 (m, 1H), 6.94-6.96 (m, 1H), 6.87-6.90 (m, 1H), 6.79-6.80 (m, 1H), 5.34 (s, 2H), 3.76 (s, 3H), 2.64-2.66 (m, 2H), 2.26-2.29 (m, 1H), 1.24 (s, 9H), 0.99-1.02 (m, 1H), 0.47-0.50 (m, 1H), 0.27-0.31 (m, 2H), 0.07-0.12 (m, 1H). Mass Spectrum (LCMS, ESI pos.): Calcd. for $C_{32}H_{33}FN_2O_4S$: 561.2 (M + H)$^+$; found: 561.3. |
| 46 | 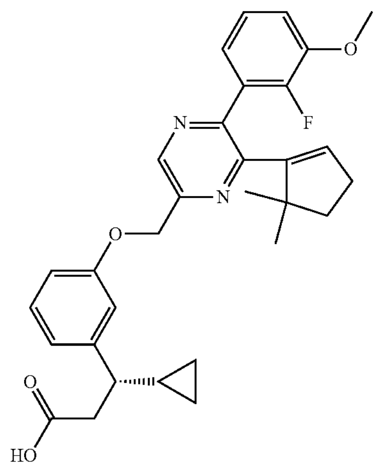 [SMILES: COc1cccc(-c2ncc(COc3cccc([C@@H](CC(=O)O)C4CC4)c3)nc2C2=CCCC2(C)C)c1F] | (3S)-3-Cyclopropyl-3-(3-((6-(5,5-dimethylcyclopent-1-enyl)-5-(2-fluoro-3-methoxyphenyl)pyrazin-2-yl)methoxy)phenyl)propanoic acid $^1$H-NMR (300 MHz, DMSO-d$_6$) δ (ppm): 8.69 (s, 1H), 7.19-7.24 (m, 3H), 6.85-7.02 (m, 4H), 6.84-6.95 (m, 3H), 5.40-5.41 (t, 1H), 5.30 (s, 2H), 3.86 (s, 3H), 2.62-2.66 (m, 2H), 2.24-2.27 (m, 1H), 2.14-2.16 (m, 2H), 1.65-1.70 (m, 2H), 1.25 (s, 6H), 0.98-1.01 (m, 1H), 0.47-0.51 (m, 1H), 0.21-0.35 (m, 2H), 0.02-0.18 (m, 1H). Mass Spectrum (LCMS, ESI pos.): Calcd. for $C_{31}H_{33}FN_2O_4$: 517.2 (M + H)$^+$; found: 517.2. |

B. (3S)-3-Cyclopropyl-3-(3-((5-(2-fluoro-5-methoxyphenyl)-6-(5-methylthiophen-2-yl)pyrazin-2-yl)methoxy)phenyl)propanoic acid, Cpd 36

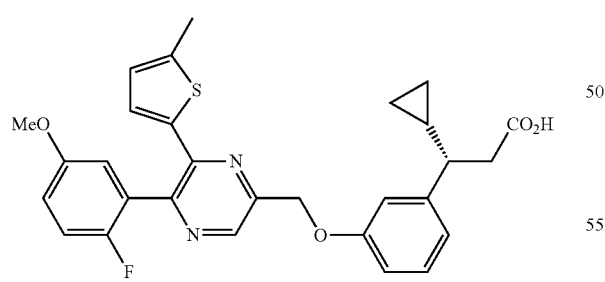

A mixture of (3S)-ethyl 3-cyclopropyl-3-(3-((5-(2-fluoro-5-methoxyphenyl)-6-(5-methylthiophen-2-yl)pyrazin-2-yl)methoxy)phenyl)propanoate (35a) (78 mg, 0.14 mmol) and sodium hydroxide (60 mg, 1.50 mmol) in tetrahydrofuran (5 mL), water (2 mL) and ethanol (1 mL) was stirred overnight at RT. The resulting mixture was concentrated to remove most of the organic solvents. The pH value of the solution was adjusted to 3-4 with 1N HCl. The solids formed were collected by filtration and dried to obtain the title compound 36. $^1$H-NMR (300 MHz, DMSO-d$_6$) δ (ppm): 12.00 (br, 1H), 8.73 (s, 1H), 7.21-7.29 (m, 2H), 7.11-7.16 (m, 2H), 6.88-7.03 (m, 3H), 6.68-6.69 (m, 1H), 6.59 (d, J=3.6 Hz, 1H), 5.30 (s, 2H), 3.78 (s, 3H), 2.63-2.67 (m, 2H), 2.32 (s, 3H), 2.27-2.30 (m, 1H), 0.99-1.02 (m, 1H), 0.47-0.50 (m, 1H), 0.22-0.31 (m, 2H), 0.07-0.12 (m, 1H). Mass Spectrum (LCMS, ESI pos.): Calcd. for $C_{29}H_{27}FN_2O_4S$: 519.2 (M+H)$^+$; found: 519.2.

Example 36

(3S)-3-Cyclopropyl-3-(3-((5-(5-fluoro-2-methoxy-pyridin-4-yl)-6-(2-methylprop-1-enyl)pyrazin-2-yl)methoxy)phenyl)propanoic acid (Cpd. 11)

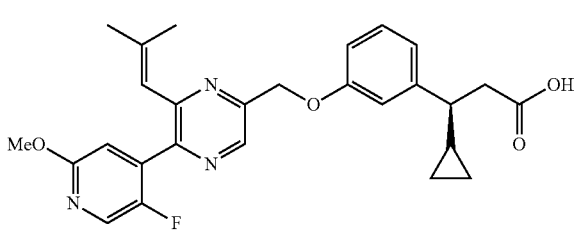 [SMILES: COc1cc(-c2ncc(COc3cccc([C@@H](CC(=O)O)C4CC4)c3)nc2C=C(C)C)c(F)cn1]

A. (3S)-Ethyl 3-(3-((6-chloro-5-(5-fluoro-2-methoxypyridin-4-yl)pyrazin-2-yl)methoxy)phenyl)-3-cyclopropylpropanoate, 36a

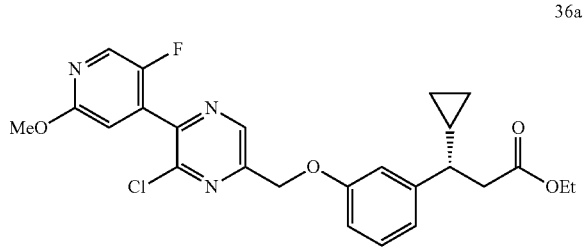 [SMILES: CCOC(=O)C[C@H](c1cccc(OCc2cnc(-c3cc(OC)ncc3F)c(Cl)n2)c1)C1CC1]

A mixture of 3-chloro-5-(chloromethyl)-2-(5-fluoro-2-methoxypyridin-4-yl)pyrazine (2e) (152 mg, 0.53 mmol), ethyl (3S)-3-cyclopropyl-3-(3-hydroxyphenyl)propanoate (1f) (130 mg, 0.55 mmol) and Cs$_2$CO$_3$ (300 mg, 0.92 mmol) in ACN (5 mL) was stirred overnight at RT. The resulting mixture was treated with 15 mL of water and extracted with EtOAc (3×10 mL). The organic layers were combined and concentrated. The residue obtained was purified by flash column chromatography (EtOAc/petroleum ether 1:9 v/v) on silica gel to obtain the title compound 36a. Mass Spectrum (LCMS, ESI pos.): Calcd. for C$_{25}$H$_{25}$ClFN$_3$O$_4$: 486.2 (M+H)$^+$; found: 486.2.

B. (3S)-Ethyl 3-cyclopropyl-3-(3-((5-(5-fluoro-2-methoxypyridin-4-yl)-6-(2-methylprop-1-enyl)pyrazin-2-yl)methoxy)phenyl)propanoate, 36b

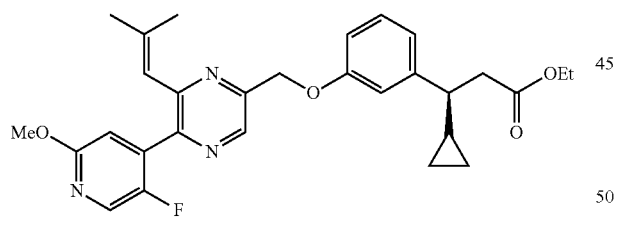

A mixture of (3S)-ethyl 3-(3-((6-chloro-5-(5-fluoro-2-methoxypyridin-4-yl)pyrazin-2-yl)methoxy)phenyl)-3-cyclopropylpropanoate (36a) (182 mg, 0.37 mmol), 4,4,5,5-tetramethyl-2-(2-methylprop-1-en-1-yl)-1,3,2-dioxaborolane (137 mg, 0.75 mmol), Pd(dppf)Cl$_2$ (14 mg, 0.02 mmol), Cs$_2$CO$_3$ (306 mg, 0.94 mmol), 1,4-dioxane (8 mL) and water (2 mL) was stirred for 1 h at 80° C. in a sealed tube under N$_2$. The resulting mixture was allowed to cool to RT and concentrated. The obtained residue was purified by flash column chromatography (EtOAc/petroleum ether 1:10-1:5 v/v) on silica gel to obtain the title compound 36b as a colorless oil. Mass Spectrum (LCMS, ESI pos.): Calcd. for C$_{29}$H$_{32}$FN$_3$O$_4$: 506.2 (M+H)$^+$; found: 506.2.

C. (3S)-3-Cyclopropyl-3-(3-((5-(5-fluoro-2-methoxypyridin-4-yl)-6-(2-methylprop-1-enyl)pyrazin-2-yl)methoxy)phenyl)propanoic acid, Cpd 11

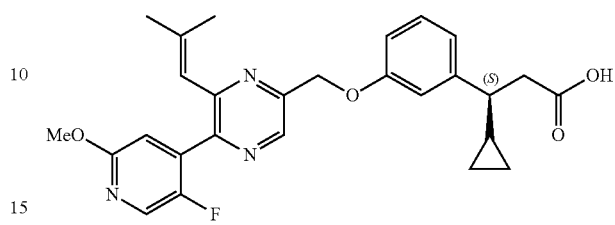

A mixture of (3S)-ethyl 3-cyclopropyl-3-(3-((5-(5-fluoro-2-methoxypyridin-4-yl)-6-(2-methylprop-1-enyl)pyrazin-2-yl)methoxy)phenyl)propanoate (36b) (135 mg, 0.27 mmol), LiOH (70 mg, 2.92 mmol), THF (5 mL), water (1 mL) and ethanol (0.5 mL) was stirred overnight at RT. The resulting mixture was concentrated to remove most of the organic solvents. The pH value of the resulting solution was then adjusted to 4-5 with 1N HCl. The solids formed were collected by filtration and dried to obtain the title compound 11 as a white solid. $^1$H-NMR (300 MHz, DMSO-d$_6$) δ (ppm): 11.99 (br, 1H), 8.71 (s, 1H), 8.30 (s, 1H), 7.23 (t, J=7.8 Hz, 1H), 6.90-6.98 (m, 2H), 6.86-6.89 (m, 2H), 6.08 (s, 1H), 5.32 (s, 2H), 3.89 (s, 3H), 2.63-2.67 (m, 2H), 2.25-2.30 (m, 1H), 2.00 (s, 3H), 1.84 (s, 3H), 0.98-1.03 (m, 1H), 0.48-0.52 (m, 1H), 0.14-0.30 (m, 2H), 0.08-0.11 (m, 1H). Mass Spectrum (LCMS, ESI pos.): Calcd. for C$_{27}$H$_{28}$FN$_3$O$_4$: 478.2 (M+H)$^+$; found: 478.1.

Example 37

(3S)-3-Cyclopropyl-3-(3-((5-(5-fluoro-2-methoxypyridin-4-yl)-6-isobutylpyrazin-2-yl)methoxy)phenyl)propanoic acid (Cpd. 2)

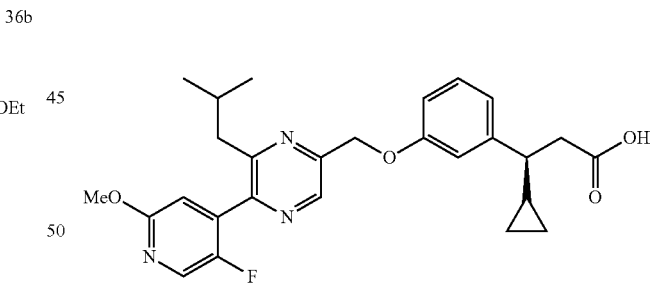

A. 5-Chloro-3-(2-methylprop-1-en-1-yl)pyrazin-2-amine, 37a

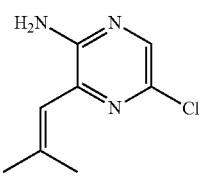

A mixture of 3-bromo-5-chloropyrazin-2-amine (41 g, 0.20 mol), 4,4,5,5-tetramethyl-2-(2-methylprop-1-en-1-yl)-1,3,2-dioxaborolane (34 g, 0.19 mol), Pd(dppf)Cl$_2$ (3.0 g, 4.1 mmol), K$_2$CO$_3$ (85 g, 0.62 mol) in dioxane (600 mL) and water (100 mL) was stirred for 24 h at 80° C. under N$_2$. The reaction was allowed to cool to RT and then quenched by the addition of 1 L of water/ice. The resulting solution was extracted with EtOAc (2×2 L). The organic layers were combined, dried (Na$_2$SO$_4$) and concentrated. The resulting black oil was used in the next step without further purification. Mass Spectrum (LCMS, ESI pos.): Calcd. for C$_8$H$_{10}$ClN$_3$: 184.1 (M+H)$^+$; found: 184.1.

B. Methyl 5-amino-6-(2-methylprop-1-en-1-yl)pyrazine-2-carboxylate, 37b

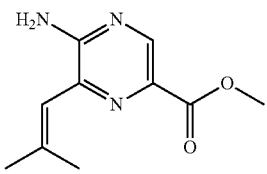

37b

A mixture of 5-chloro-3-(2-methylprop-1-en-1-yl)pyrazin-2-amine (37a) (51 g, 0.28 mol), Pd(dppf)Cl$_2$ (4.0 g, 5.5 mmol) and triethylamine (100 mL) in methanol (1500 mL) was stirred overnight at 110° C. under a CO$_{(g)}$ (60 atm) atmosphere. The resulting mixture was allowed to cool to RT, depressurized and concentrated. The residue obtained was purified by flash column chromatography (50% EtOAc/petroleum ether) on silica gel to obtain the title compound 37b. Mass Spectrum (LCMS, ESI pos.): Calcd. for C$_{10}$H$_{13}$N$_3$O$_2$: 208.1 (M+H)$^+$; found: 208.1.

C. Methyl 5-amino-6-isobutylpyrazine-2-carboxylate, 37c

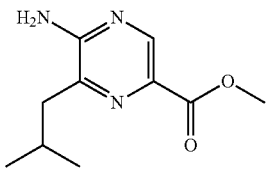

37c

A mixture of methyl 5-amino-6-(2-methylprop-1-en-1-yl)pyrazine-2-carboxylate (37b) (20 g, 96 mmol) and 10% Pd/C (20 g) in methanol (500 mL) was stirred for 10 h at 30° C. under a H$_2$ (3 atm) atmosphere. The reaction mixture was filtered through a pad of diatomaceous earth and the filtrate was concentrated to yield the title compound 37c. Mass Spectrum (LCMS, ESI pos.): Calcd. for C$_{10}$H$_{15}$N$_3$O$_2$: 210.1 (M+H)$^+$; found: 210.1.

D. Methyl 5-bromo-6-isobutylpyrazine-2-carboxylate, 37d

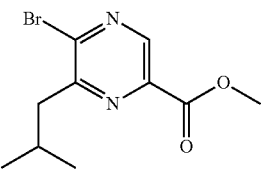

37d

The mixture of isoamyl nitrite (100 mL) and methyl 5-amino-6-isobutylpyrazine-2-carboxylate (37c) (20 g, 96 mmol) in dibromomethane (200 mL) was stirred for 0.5 h at 0° C., followed by the addition of bromotrimethylsilane (70 mL) dropwise for 20 min. The resulting mixture was stirred for 5 h at 30° C. The reaction was then quenched by the addition of water/ice (500 mL). The pH of the mixture was adjusted to 7 using K$_2$CO$_3$. The resulting solution was extracted with DCM (2×1 L). The organic layers were combined and dried (Na$_2$SO$_4$). The mixture was filtered and concentrated. The residue obtained was purified by flash column chromatography (0-10% EtOAc/petroleum ether) on silica gel to obtain the title compound 37d. $^1$H-NMR (400 MHz, CDCl$_3$) δ (ppm): 8.58 (s, 1H); 4.02 (s, 3H); 2.96-2.98 (m, J=8.0 Hz, 2H); 2.31-2.33 (m, J=8.0 Hz, 1H); 0.98 (m, 6H). Mass Spectrum (LCMS, ESI pos.): Calcd. for C$_{10}$H$_{13}$BrN$_2$O$_2$: 273.0 (M+H)$^+$; found: 272.9.

E. (5-Bromo-6-isobutylpyrazin-2-yl)methanol, 37e

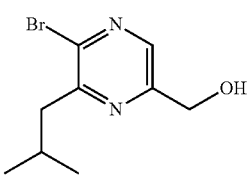

37e

To a solution of methyl 5-bromo-6-isobutylpyrazine-2-carboxylate (37d) (29 g, 0.11 mol) in tetrahydrofuran (300 mL) was added DIBALH (300 mL, 1 M in THF) dropwise at −70° C. for 30 min. The resulting solution was stirred for 30 min at −70° C. and for 30 min at RT. The pH of the mixture was adjusted to 6 with aqueous HCl solution (3N). The resulting solution was extracted with EtOAc (2×2 L). The organic layers were combined and dried (Na$_2$SO$_4$). The mixture was filtered and the filtrate was concentrated. The residue was purified by flash column chromatography (EtOAc/petroleum ether 1:10 v/v) on silica gel to obtain the title compound 37e. Mass Spectrum (LCMS, ESI pos.): Calcd. for C$_9$H$_{13}$BrN$_2$O: 245.0 (M); found: 245.0.

F. (5-(5-Fluoro-2-methoxypyridin-4-yl)-6-isobutylpyrazin-2-yl)methanol, 37f

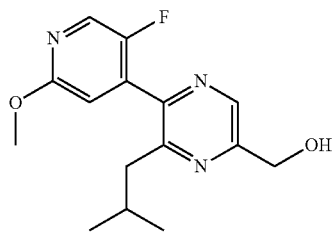

37f

A mixture of methyl 5-bromo-6-(propan-2-yl)pyrazine-2-carboxylate (37e) (24 g, 98 mmol), (2-fluoro-5-methoxyphenyl)boronic acid (34 g, 0.20 mol), Pd(dppf)Cl$_2$ (1.0 g, 1.3 mmol) and triethylamine (50 g, 0.49 mol) in methanol (500 mL) was stirred for 8 h at 70° C. The reaction mixture was allowed to cool to RT and concentrated under reduced pressure. The residue obtained was purified by flash column chromatography (EtOAc/petroleum ether 1:10 v/v) on silica gel to obtain the title compound 37f. Mass Spectrum (LCMS, ESI pos.): Calcd. for $C_{15}H_{18}FN_3O_2$: 292.1 (M+H)$^+$; found: 292.1.

G. 5-(Chloromethyl)-2-(5-fluoro-2-methoxypyridin-4-yl)-3-isobutylpyrazine, 37g

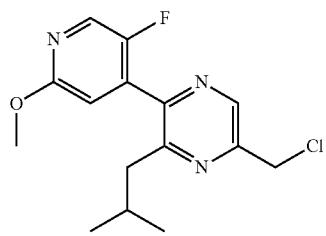

37g

To a solution of [5-(2-fluoro-5-methoxyphenyl)-6-(propan-2-yl)pyrazin-2-yl]methanol (37f) (20 g, 69 mmol) in dichloromethane (200 mL) was added thionyl chloride (30 mL) at 0° C. dropwise within 30 min under N$_2$. The resulting solution was stirred for 3 h at 10° C. The reaction was then quenched by the addition of 1 L of water/ice. The resulting mixture was extracted with dichloromethane (2×1 L). The organic layers were combined, dried (Na$_2$SO$_4$) and concentrated to obtain the title compound 37g. Mass Spectrum (LCMS, ESI pos.): Calcd. for $C_{15}H_{17}ClFN_3O$: 310.8 (M+H)$^+$; found: 310.0.

H. (S)-Methyl 3-cyclopropyl-3-(3-((5-(5-fluoro-2-methoxypyridin-4-yl)-6-isobutylpyrazin-2-yl)methoxy)phenyl)propanoate, 37h

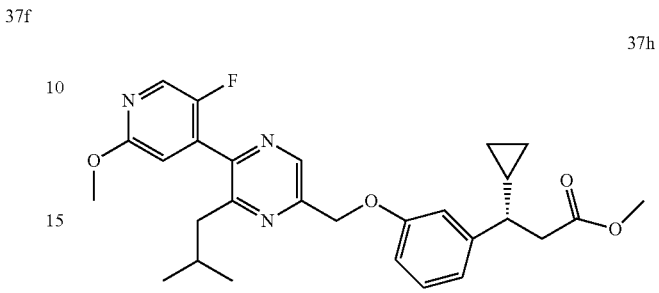

37h

A mixture of 5-(chloromethyl)-2-(5-fluoro-2-methoxypyridin-4-yl)-3-isobutylpyrazine (37g) (24 g, 77 mmol), methyl (3S)-3-cyclopropyl-3-(3-hydroxyphenyl)propanoate (18 g, 82 mmol) and K$_2$CO$_3$ (50 g, 0.36 mol) in CH$_3$CN (600 mL) was stirred overnight at 70° C. The reaction was allowed to cool to RT and quenched by the addition of 1 L of water/ice. The resulting solution was extracted with EtOAc (1.5 L). The organic layers were combined, dried (Na$_2$SO$_4$) and concentrated. The residue obtained was purified by flash column chromatography (EtOAc/petroleum ether 1:10 v/v) on silica gel to obtain the title compound 37h. Mass Spectrum (LCMS, ESI pos.): Calcd. for $C_{28}H_{32}FN_3O_4$: 494.2 (M+H)$^+$; found: 494.2.

I. (3S)-3-Cyclopropyl-3-(3-((5-(5-fluoro-2-methoxypyridin-4-yl)-6-isobutylpyrazin-2-yl)methoxy)phenyl)propanoic acid, Cpd 2

A mixture of (S)-methyl 3-cyclopropyl-3-(3-((5-(5-fluoro-2-methoxypyridin-4-yl)-6-isobutylpyrazin-2-yl)methoxy)phenyl)propanoate (37h, 6.0 g, 12 mmol), LiOH.H$_2$O (6.0 g, 0.14 mol) in THF (60 mL) and water (60 mL) was stirred overnight at RT. The reaction mixture was concentrated, and pH of the solution was adjusted to 4 using 3 N HCl solution. The resulting mixture was extracted with EtOAc (2×500 mL). The combined organic layers were dried over anhydrous Na$_2$SO$_4$ and concentrated under vacuum. The residue was re-crystallized from n-hexane to obtain the title compound 2. $^1$H-NMR (400 MHz, DMSO-d$_6$) δ (ppm): 12.00 (s, 1H), 8.76 (s, 1H), 8.32 (s, 1H), 7.23 (t, J=8.0 Hz, 1H), 7.03 (d, J=4.8 Hz, 1H), 6.99 (s, 1H), 6.87-6.94 (m, 2H), 5.30 (s, 2H), 3.90 (s, 3H), 2.59-2.61 (m, 2H), 2.44-2.53 (m, 2H), 2.26-2.39 (m, 1H), 1.98-2.07 (m, 1H), 0.90-0.96 (m, 1H), 0.75 (d, J=6.4 Hz, 6H), 0.40-0.48 (m, 1H), 0.20-0.29 (m, 2H), 0.02-0.09 (m, 1H). Mass Spectrum (LCMS, ESI pos.): Calcd. for $C_{27}H_{30}FN_3O_4$: 480.2 (M+H)$^+$; found: 480.2.

Example 38

(3S)-3-Cyclopropyl-3-(3-((5-(2-fluoro-5-methoxyphenyl)-6-(oxetan-3-yloxy)pyrazin-2-yl)methoxy)phenyl)propanoic acid (Cpd. 41)

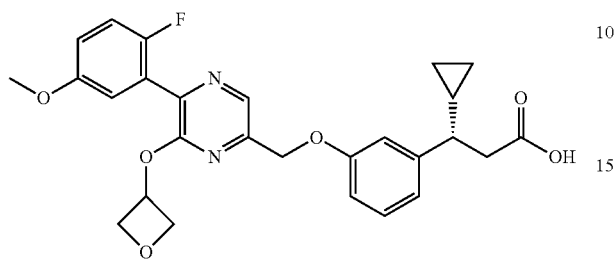

The title compound 41 was prepared from ethyl (3S)-3-(3-[[6-chloro-5-(2-fluoro-5-methoxyphenyl)pyrazin-2-yl]methoxy]phenyl)-3-cyclopropylpropanoate (1g) and oxetan-3-ol following an adaptation of the procedure described in Example 3 treating the alcohol with NaH at RT for 30 min and heating at 75° C. for 2 h rather than treating the alcohol with NaH at 0° C. for 10 min. and refluxing overnight. $^1$H-NMR (300 MHz, DMSO-$d_6$) δ (ppm): 8.53 (s, 1H), 7.10-7.28 (m, 4H), 6.90-6.95 (m, 1H), 6.86-6.95 (m, 2H), 5.61-5.62 (m, 1H), 5.19 (s, 2H), 4.81-4.85 (m, 2H), 4.47 (t, J=6.3 Hz, 2H), 3.79 (s, 3H), 2.51-2.60 (m, 2H), 2.19-2.24 (m, 1H), 0.96-1.01 (m, 1H), 0.44-0.50 (m, 1H), 0.24-0.29 (m, 2H), 0.07-0.09 (m, 1H). Mass Spectrum (LCMS, ESI pos.): Calcd. for $C_{27}H_{27}FN_2O_6$: 495.2 (M+H)$^+$; found: 495.3.

Example 39

(3S)-3-(3-((6-(Cyclohexyloxy)-5-(5-fluoro-2-methoxypyridin-4-yl)pyrazin-2-yl)methoxy)phenyl)-3-cyclopropylpropanoic acid (Cpd. 9)

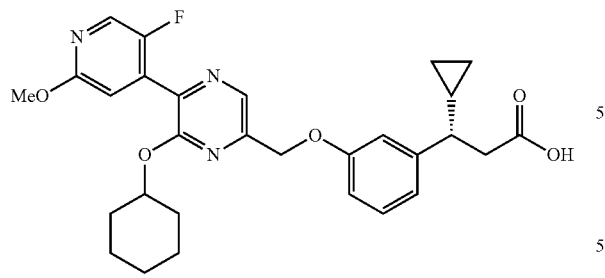

The title compound 9 was prepared from (3S)-methyl 3-(3-((6-chloro-5-(5-fluoro-2-methoxypyridin-4-yl)pyrazin-2-yl)methoxy)phenyl)-3-cyclopropylpropanoate (2f) and cyclohexanol following the procedure described in Example 3 treating the alcohol with NaH at RT for 30 min and heating at 75° C. for 3 h rather than treating the alcohol with NaH at 0° C. for 10 min. and refluxing overnight. $^1$H-NMR (300 MHz, DMSO-$d_6$) δ (ppm): 8.47 (s, 1H), 8.28 (s, 1H), 7.18-7.24 (m, 1H), 6.85-6.96 (m, 4H), 5.23 (s, 2H), 5.09-5.12 (m, 1H), 3.88 (s, 3H), 2.50-2.60 (m, 2H), 2.26-2.28 (m, 1H), 1.86-1.90 (m, 2H), 1.24-1.60 (m, 8H), 0.98-1.00 (m, 1H), 0.46-0.50 (m, 1H), 0.24-0.26 (m, 2H), 0.07-0.09 (m, 1H). Mass Spectrum (LCMS, ESI pos.): Calcd. for $C_{29}H_{32}FN_3O_5$: 522.2 (M+H)$^+$; found: 522.2.

Example 40

(3S)-3-(3-((6-(Cyclopentyloxy)-5-(5-fluoro-2-methoxypyridin-4-yl)pyrazin-2-yl)methoxy)phenyl)-3-cyclopropylpropanoic acid (Cpd. 16)

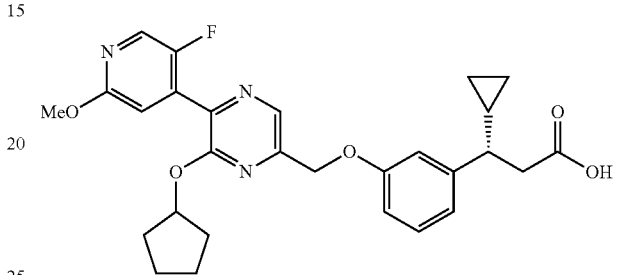

The title compound 16 was prepared from (3S)-methyl 3-(3-((6-chloro-5-(5-fluoro-2-methoxypyridin-4-yl)pyrazin-2-yl)methoxy)phenyl)-3-cyclopropylpropanoate (2f) and cyclopentanol following the procedure described in Example 3 treating the alcohol with NaH at RT for 30 min and heating at 75° C. for 3 h rather than treating the alcohol with NaH at 0° C. for 10 min. and refluxing overnight. $^1$H-NMR (300 MHz, DMSO-$d_6$) δ (ppm): 8.47 (s, 1H), 8.27 (s, 1H), 7.23 (t, J=7.8 Hz, 1H), 6.86-6.99 (m, 4H), 5.44-5.48 (m, 1H), 5.24 (s, 2H), 3.88 (s, 3H), 2.63-2.67 (m, 2H), 2.22-2.28 (m, 1H), 1.87-1.91 (m, 2H), 1.58-1.67 (m, 6H), 0.99-1.03 (m, 1H), 0.48-0.51 (m, 1H), 0.27-0.30 (m, 2H), 0.08-0.13 (m, 1H). Mass Spectrum (LCMS, ESI pos.): Calcd. for $C_{28}H_{30}FN_3O_5$: 508.2 (M+H)$^+$; found: 508.2.

Example 41

(3S)-3-Cyclopropyl-3-(3-((6-(cyclopropylmethoxy)-5-(5-fluoro-2-methoxypyridin-4-yl)pyrazin-2-yl)methoxy)phenyl)propanoic acid (Cpd. 48)

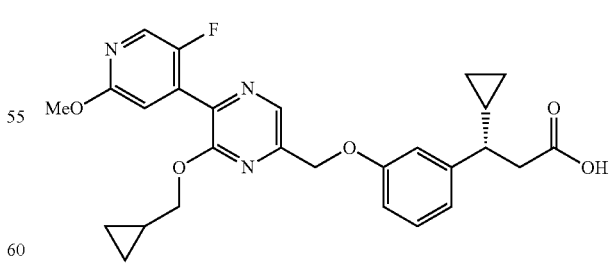

The title compound was prepared from (3S)-methyl 3-(3-((6-chloro-5-(5-fluoro-2-methoxypyridin-4-yl)pyrazin-2-yl)methoxy)phenyl)-3-cyclopropylpropanoate (2f) and cyclopropylmethanol following the procedure described in Example 3 treating the alcohol with NaH at RT for 30 min and heating at reflux for 1 h rather than treating the alcohol with NaH at 0° C. for 10 min. and refluxing overnight. ¹H-NMR (300 MHz, DMSO-d₆) δ (ppm): 8.49 (s, 1H), 8.28 (s, 1H), 7.20 (t, J=7.8 Hz, 1H), 7.05 (d, J=4.8 Hz, 1H), 6.85-6.94 (m, 3H), 5.21 (s, 2H), 4.22 (d, J=6.9 Hz, 2H), 3.89 (s, 3H), 2.38-2.52 (m, 3H), 1.19-1.23 (m, 1H), 0.91-0.93 (m, 1H), 0.48-0.53 (m, 3H), 0.24-0.30 (m, 4H), 0.01-0.09 (m, 1H). Mass Spectrum (LCMS, ESI pos.): Calcd. for C₂₇H₂₈FN₃O₅: 494.2 (M+H)⁺; found: 494.2.

Example 42

(3S)-3-Cyclopropyl-3-(3-((5-(5-fluoro-2-methoxy-pyridin-4-yl)-6-(neopentyloxy)pyrazin-2-yl)methoxy)phenyl)propanoic acid (Cpd. 47)

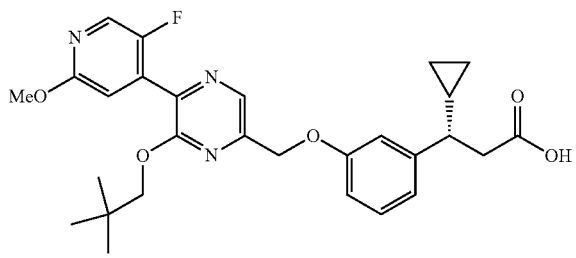 [SMILES: COc1cc(-c2ncc(COc3cccc([C@@H](CC(=O)O)C4CC4)c3)nc2OCC(C)(C)C)c(F)cn1]

The title compound was prepared from (3S)-methyl 3-(3-((6-chloro-5-(5-fluoro-2-methoxypyridin-4-yl)pyrazin-2-yl)methoxy)phenyl)-3-cyclopropylpropanoate (2f) and 2,2-dimethylpropan-1-ol following the procedure described in Example 3 treating the alcohol with NaH at RT for 30 min and heating at 75° C. for 2 h rather than treating the alcohol with NaH at 0° C. for 10 min. and refluxing overnight. ¹H-NMR (300 MHz, DMSO-d₆) δ (ppm): 8.50 (s, 1H), 8.30 (s, 1H), 7.19-7.24 (m, 1H), 7.04 (d, J=4.5 Hz, 1H), 6.86-6.96 (m, 3H), 5.22 (s, 2H), 4.03 (s, 2H), 3.89 (s, 3H), 2.52-2.58 (m, 2H), 2.29-2.34 (m, 1H), 0.95-0.98 (m, 1H), 0.90 (s, 9H), 0.45-0.47 (m, 1H), 0.22-0.29 (m, 2H), 0.06-0.08 (m, 1H). Mass Spectrum (LCMS, ESI pos.): Calcd. for C₂₈H₃₂FN₃O₅: 510.2 (M+H)⁺; found: 510.1.

Example 43

(3S)-3-Cyclopropyl-3-(3-((5-(2-fluoro-5-methoxy-phenyl)-6-morpholinopyrazin-2-yl)methoxy)phenyl)propanoic acid (Cpd. 45)

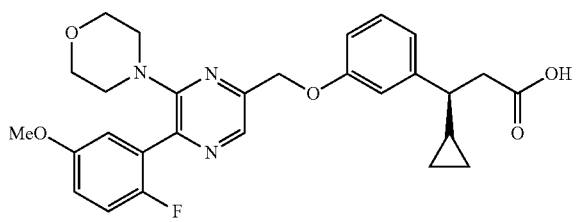

A. (3S)-Methyl 3-cyclopropyl-3-(3-((5-(2-fluoro-5-methoxyphenyl)-6-morpholinopyrazin-2-yl)methoxy)phenyl)propanoate, 43a

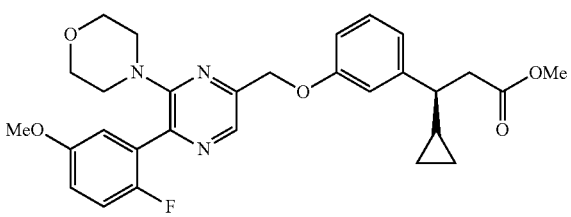

A mixture of (3S)-methyl 3-(3-((6-chloro-5-(2-fluoro-5-methoxyphenyl)pyrazin-2-yl)methoxy)phenyl)-3-cyclopropylpropanoate (110 mg, 0.23 mmol, prepared following the procedure described in Example 1, Step G) and morpholine (260 mg, 2.98 mmol) in DMSO (3 mL) was stirred overnight at 120° C. The resulting mixture was allowed to cool to RT and concentrated. The residue obtained was purified by flash column chromatography (EtOAc/petroleum ether 1:10-1:5 v/v) on silica gel to obtain the title compound 43a. Mass Spectrum (LCMS, ESI pos.): Calcd. for C₂₉H₃₂FN₃O₅: 522.2 (M+H)⁺; found: 522.3.

B. (3S)-3-Cyclopropyl-3-(3-((5-(2-fluoro-5-methoxyphenyl)-6-morpholinopyrazin-2-yl)methoxy)phenyl)propanoic acid, 43b

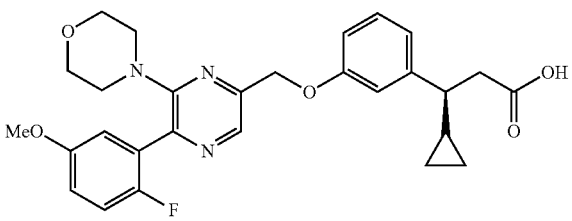 [SMILES: COc1ccc(F)c(-c2ncc(COc3cccc([C@@H](CC(=O)O)C4CC4)c3)nc2N2CCOCC2)c1]

A mixture of (3S)-methyl 3-cyclopropyl-3-(3-((5-(2-fluoro-5-methoxyphenyl)-6-morpholinopyrazin-2-yl)methoxy)phenyl)propanoate (43a) (95 mg, 0.18 mmol), THF (5 mL), LiOH (49 mg, 2.05 mmol), water (2 mL) and methanol (1 mL) was stirred overnight at RT. The reaction mixture was then concentrated to remove most of the organic solvent. The pH value of the resulting solution was adjusted to 3-4 with 1N HCl. The solids formed were collected by filtration and dried in a vacuum oven to obtain the title compound 43b. ¹H-NMR (300 MHz, DMSO-d₆) δ (ppm): 8.31 (s, 1H), 7.14-7.29 (m, 3H), 7.02-7.06 (m, 1H), 7.00 (s, 1H), 6.85-6.96 (m, 2H), 5.15 (s, 2H), 3.78 (s, 3H), 3.50-3.53 (m, 4H), 3.11-3.14 (m, 4H), 2.50-2.57 (m, 2H), 2.27-2.33 (m, 1H), 0.96-0.99 (m, 1H), 0.45-0.48 (m, 1H), 0.23-0.29 (m, 2H), 0.01-0.09 (m, 1H). Mass Spectrum (LCMS, ESI pos.): Calcd. for C₂₈H₃₀FN₃O₅: 508.2 (M+H)⁺; found: 508.2.

Example 44

(3S)-3-Cyclopropyl-3-(3-((5-(2-fluoro-5-methoxy-phenyl)-6-(neopentylamino)pyrazin-2-yl)methoxy)phenyl)propanoic acid (Cpd. 44)

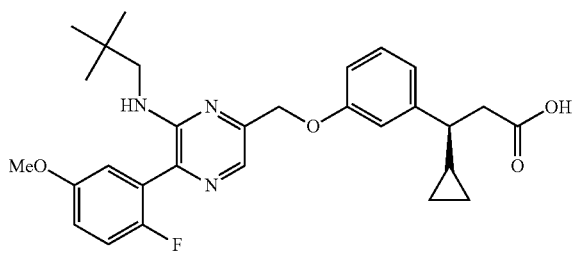 [SMILES: COc1ccc(F)c(-c2ncc(COc3cccc([C@@H](CC(=O)O)C4CC4)c3)nc2NCC(C)(C)C)c1]

The title compound 44 was prepared from (3S)-methyl 3-(3-((6-chloro-5-(2-fluoro-5-methoxyphenyl)pyrazin-2-yl)methoxy)phenyl)-3-cyclopropylpropanoate (4a) and 2,2-dimethylpropan-1-amine following the procedure described in Example 43, Steps A-B. $^1$H-NMR (300 MHz, DMSO-d$_6$) δ (ppm): 7.91 (s, 1H), 7.16-7.30 (m, 2H), 6.83-7.08 (m, 5H), 5.97-6.01 (m, 1H), 5.04 (s, 2H), 3.77 (s, 3H), 3.21 (d, J=6.3 Hz, 2H), 2.58-2.62 (m, 2H), 2.26-2.31 (m, 1H), 0.97-1.01 (m, 1H), 0.85 (s, 9H), 0.46-0.48 (m, 1H), 0.27-0.31 (m, 2H), 0.01-0.10 (m, 1H). Mass Spectrum (LCMS, ESI pos.): Calcd. for $C_{29}H_{34}FN_3O_4$: 508.3 (M+H)$^+$; found: 508.3.

Example 45

(3S)-3-Cyclopropyl-3-(3-((6-((3,3-dimethylcyclobu-tyl)methoxy)-5-(2-fluoro-5-methoxyphenyl)pyrazin-2-yl)methoxy)phenyl)propanoic acid (Cpd. 42)

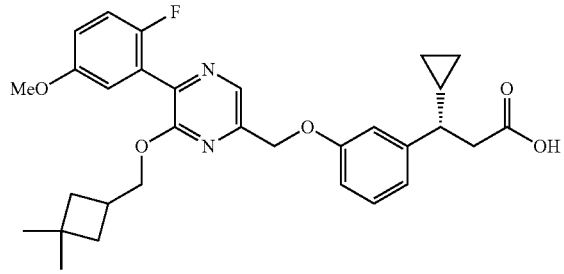 [SMILES: COc1ccc(F)c(-c2ncc(COc3cccc([C@@H](CC(=O)O)C4CC4)c3)nc2OCC2CC(C)(C)C2)c1]

A. (3,3-Dimethylcyclobutyl)methanol, 45a

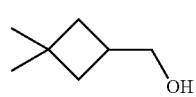

45a

To a solution of 3,3-dimethylcyclobutane-1-carboxylic acid (870 mg, 6.79 mmol) in THF (10 mL) was added LiAlH$_4$ (516 mg, 13.60 mmol) in portions at 0° C. The resulting solution was stirred for 3 h at RT. The reaction was then quenched by the addition of 0.5 mL of water. The solids were filtered and the filter cake was washed with EtOAc (3×100 mL). The combined EtOAc layers were concentrated and the residue obtained was purified by flash column chromatography (EtOAc/petroleum ether 1:2 v/v) on silica gel to obtain the title compound 45a. $^1$H-NMR (300 MHz, CDCl$_3$) δ (ppm): 3.58 (d, J=6.9 Hz, 2H), 2.37-2.48 (m, 1H), 1.78-1.85 (m, 2H), 1.48-1.55 (m, 2H), 1.34 (s, 3H), 1.28 (s, 3H).

B. (3S)-3-Cyclopropyl-3-(3-((6-((3,3-dimethylcy-clobutyl)methoxy)-5-(2-fluoro-5-methoxyphenyl)pyrazin-2-yl)methoxy)phenyl)propanoic acid, 45b The title compound 45b was prepared from methyl (3S)-3-(3-[[6-chloro-5-(2-fluoro-5-methoxyphenyl)pyrazin-2-yl]methoxy]phenyl)-3-cyclopropylpropanoate (4a) and (3,3-dimethylcyclobutyl)methanol (45a) following the procedure described in Example 3. $^1$H-NMR (300 MHz, DMSO-d$_6$) δ (ppm): 8.45 (s, 1H), 7.19-7.24 (m, 2H), 7.06-7.08 (m, 2H), 6.86-6.98 (m, 3H), 5.19 (s, 2H), 4.26 (d, J=5.7 Hz, 2H), 3.77 (s, 3H), 2.59-2.61 (m, 3H), 2.20-2.26 (m, 1H), 1.61-1.69 (m, 4H), 1.10 (s, 3H), 0.93-1.09 (m, 1H), 0.92 (s, 3H), 0.47-0.50 (m, 1H), 0.27-0.31 (m, 2H), 0.07-0.12 (m, 1H). Mass Spectrum (LCMS, ESI pos.): Calcd. for $C_{31}H_{35}FN_2O_5$: 535.3 (M+H)$^+$; found: 535.1.

Biological Examples

In Vitro Assays

Example 1

GPR40 Calcium Flux Assay

Compounds were tested in a calcium flux assay using transfected HEK293 cells stably expressing either human GPR40 or rat GPR40. Human GPR40 expressing cells were cultured in DMEM-High Glucose media supplemented with 10% fetal bovine serum, 1×L-Glutamine, 1× Penicillin/Streptomycin and 500 μg/mL G418. Rat GPR40 expressing cells were cultured in DMEM-High Glucose media supplemented with 10% fetal bovine serum and 1 μg/mL puromycin. Cells were plated into poly-D-lysine coated 384-well plates and cultured overnight in a 37° C. humidified tissue culture incubator under 5% CO$_2$/90% O$_2$ atmosphere. On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (I) were loaded into a fluorescent plate reader that added compounds onto the cells while measuring the fluorescence intensity of each well. The plate reader recorded fluorescence intensity at 1 second intervals for 8 min and provided the data for analysis in an Excel format. EC50 values were calculated using Prism (GraphPad) software. Resultant data are shown in Table 2.

TABLE 2

| Cpd | hGPR40 Ca$^{2+}$ Assay EC50 (μM) | rGPR40 Ca$^{2+}$ Assay EC50 (μM) |
|---|---|---|
| 1 | 0.002, 0.002 | 0.039, 0.025 |
| 2 | 0.002, 0.001, 0.003, 0.002 | 0.007, 0.008, 0.012, 0.007 |

TABLE 2-continued

| Cpd | hGPR40 Ca$^{2+}$ Assay EC50 (μM) | rGPR40 Ca$^{2+}$ Assay EC50 (μM) |
|---|---|---|
| 3 | 0.003, 0.002 | 0.033, 0.026 |
| 4 | 0.009, 0.003, 0.002 | 0.013, 0.013, 0.009 |
| 5 | 0.003, 0.002 | 0.012, 0.010 |
| 6 | 0.005, 0.004 | 0.017, 0.014 |
| 7 | 0.007, 0.006 | 0.029, 0.027 |
| 8 | 0.010, 0.009, 0.014, 0.008, 0.006 | 0.039, 0.029, 0.076, 0.050 |
| 9 | 0.007, 0.007 | 0.020, 0.016 |
| 10 | 0.008, 0.007 | 0.033, 0.029 |
| 11 | 0.011, 0.007 | 0.029, 0.023 |
| 12 | 0.011, 0.008 | 0.024, 0.021 |
| 13 | 0.019, 0.019, 0.020, 0.010, 0.008 | 0.031, 0.030, 0.030, 0.053, 0.033 |
| 14 | 0.010, 0.010, 0.009 | 0.016, 0.032, 0.031, 0.021, 0.018 |
| 15 | 0.015, 0.007 | 0.021, 0.015 |
| 16 | 0.011, 0.010 | 0.038, 0.036 |
| 17 | 0.011, 0.010 | 0.029, 0.028 |
| 18 | 0.013, 0.010 | 0.105, 0.067 |
| 19 | 0.014, 0.011 | 0.070, 0.049 |
| 20 | 0.015, 0.011 | 0.090, 0.078 |
| 21 | 0.017, 0.012 | 0.065, 0.057 |
| 22 | 0.018, 0.012 | 0.053, 0.046, 0.043, 0.031, |
| 23 | 0.023, 0.014 | 0.058, 0.050 |
| 24 | 0.024, 0.016, 0.040 | 0.187, 0.178, 0.183 |
| 25 | 0.023, 0.018 | 0.045, 0.040 |
| 26 | 0.021, 0.021 | 0.111, 0.108 |
| 27 | 0.028, 0.021 | 0.048, 0.034 |
| 28 | 0.026, 0.023 | 0.057, 0.054 |
| 29 | 0.039, 0.030, 0.021, 0.026, 0.023 | 0.073, 0.056, 0.098, 0.073, 0.062 |
| 30 | 0.037, 0.035, 0.014, 0.014, 0.011, 0.008, 0.096, 0.081 | 0.126, 0.120, 0.112, 0.099, 0.063, 0.044, 0.038, 0.028, 0.745, 0.632 |
| 31 | 0.032, 0.026 | 0.102, 0.066 |
| 32 | 0.030, 0.028 | 0.119, 0.094 |
| 33 | 0.034, 0.027 | 0.120, 0.110, 0.100, 0.082 |
| 34 | 0.033, 0.030 | 0.112, 0.104, 0.088, 0.086 |
| 35 | 0.050, 0.025 | 0.356, 0.242 |
| 36 | 0.040, 0.038 | 0.118, 0.109, 0.105, 0.086 |
| 37 | 0.045, 0.044 | 0.141, 0.109 |
| 38 | 0.055, 0.042 | 0.399, 0.395 |
| 39 | 0.130, 0.098, 0.064, 0.050 | 0.395, 0.358, 0.247, 0.208 |
| 40 | 0.064, 0.052 | 0.253, 0.249, 0.236, 0.227 |
| 41 | 0.079, 0.069 | 0.553, 0.416 |
| 42 | 0.017, 0.014 | 0.032, 0.029 |
| 43 | 0.015, 0.012 | 0.081, 0.055 |
| 44 | 0.017, 0.011 | 0.059, 0.069 |
| 45 | 0.034, 0.034 | 0.138, 0.134 |
| 46 | 0.130, 0.127 | 0.637, 0.788 |
| 47 | 0.003, 0.003 | 0.013, 0.014 |
| 48 | 0.035, 0.032 | 0.138, 0.152 |

In-Vivo Assay

Oral Glucose Tolerance Test

Male SD rats (200-250 g) were housed 2 per cage in a temperature-controlled room with a 12-hour light/dark cycle. They were allowed ad libitum access to water and fed with normal rodent chow. The night before the oral glucose tolerance test (oGTT), the rats were transferred to clean cages and fasted overnight. On the morning of the oGTT, the rats were weighed and randomized into groups based on fasted blood glucose and body weight. Rats were dosed with vehicle (0.5% methocel) or compounds thirty min prior to the oGTT (glucose, 2 g/kg, po). Blood was collected from the tail vein at 0, 10, 30, 60 and 120 minutes after glucose challenge to measure blood glucose; plasma was used to determine insulin levels. The area under the curve for blood glucose excursion was calculated from t=0 to t=120 minutes, Percent lowering of glucose was calculated from the AUC data with respect to the vehicle-treated group. Resultant data are shown in Table 3.

TABLE 3

| Cpd No. | Percent Lowering of Glucose (AUC compound vs. AUC Vehicle) |
|---|---|
| 2 | 87 |
| 8 | 91 |
| 13 | 84 |
| 30 | 87 |

Note:
AUC = Integrated area under the glucose excursion curve from t = 0 to t = 120 minutes.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

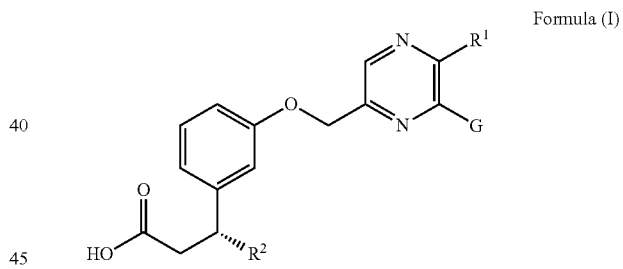

Formula (I)

wherein

R$^1$ is selected from the group consisting of phenyl, pyridin-4-yl, and thiophenyl; wherein R$^1$ is optionally and independently substituted with one or two substituents selected from the group consisting of C$_{1-4}$alkyl, methoxy, fluoro, cyano, and trifluoromethyl; provided that phenyl of R$^1$ is substituted with no more than one methoxy substituent;

G is selected from the group consisting of C$_{1-6}$alkyl; C$_{1-6}$alkoxy; C$_{3-7}$cycloalkyl; 2,2,6,6-tetramethyltetrahydro-2H-pyran-4-yloxy; oxetan-3-yloxy; C$_{2-6}$alk-1-en-1-yl; 3,3,3-trifluoropropyloxy; 1,1,1-trifluoroprop-2-yl; (C$_{1-6}$alkyl)thiophen-2-yl; phenyl optionally substituted with one or two C$_{1-4}$alkyl substituents; (C$_{1-6}$alkyl)amino; di(C$_{1-6}$alkyl)amino; N-containing heterocyclyl wherein said N-containing heterocyclyl is attached to the core pyrazine ring via a nitrogen atom and said N-containing heterocyclyl is optionally spiro-fused to a C$_{3-7}$cycloalkyl group; ring g1

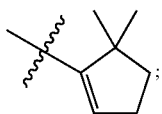

C$_{3-7}$cycloalkyloxy; and C$_{3-7}$cycloalkyl-methoxy;
wherein C$_{3-7}$cycloalkyloxy and the C$_{3-7}$cycloalkyl portion of C$_{3-7}$cycloalkyl-methoxy are optionally substituted with one to four methyl substituents; and
R$^2$ is C$_{3-5}$cycloalkyl, C$_{1-6}$alkyl, or cyano;
or an enantiomer, diastereomer, or pharmaceutically acceptable salt thereof.

2. The compound of claim 1, wherein G is selected from the group consisting of C$_{1-6}$alkyl; C$_{1-6}$alkoxy; 2,2,6,6-tetramethyltetrahydro-2H-pyran-4-yloxy; C$_{2-6}$alk-1-en-1-yl; 3,3,3-trifluoropropyloxy; (C$_{1-6}$alkyl)thiophen-2-yl; phenyl optionally substituted with one or two C$_{1-4}$alkyl substituents; N-containing heterocyclyl wherein said N-containing heterocyclyl is attached to the core pyrazine ring via a nitrogen atom and said N-containing heterocyclyl is optionally spirofused to a C$_{3-7}$cycloalkyl group; ring g1

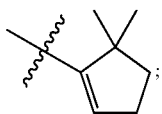

C$_{3-7}$cycloalkyloxy; and C$_{3-7}$cycloalkyl-methoxy;
wherein said C$_{3-7}$cycloalkyloxy and the C$_{3-7}$cycloalkyl portion of C$_{3-7}$cycloalkyl-methoxy are optionally substituted with one to four methyl substituents.

3. The compound of claim 2, wherein G is selected from the group consisting of C$_{1-6}$alkyl; C$_{1-6}$alkoxy; 2,2,6,6-tetramethyltetrahydro-2H-pyran-4-yloxy; C$_{2-4}$alk-1-en-1-yl; 3,3,3-trifluoropropyloxy; (methyl)thiophen-2-yl; phenyl optionally substituted with one or two C$_{1-4}$alkyl substituents; N-containing heterocyclyl wherein said N-containing heterocyclyl is selected from the group consisting of piperidin-1-yl and azetidin-1-yl and said N-containing heterocyclyl is optionally spirofused to a C$_{3-7}$cycloalkyl; ring g1

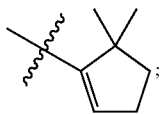

C$_{3-7}$cycloalkyloxy; and C$_{3-7}$cycloalkyl-methoxy;
wherein said C$_{3-7}$cycloalkyloxy and the C$_{3-7}$cycloalkyl portion of C$_{3-7}$cycloalkyl-methoxy are optionally substituted with one to four methyl substituents.

4. The compound of claim 1, wherein R$^1$ is selected from the group consisting of phenyl and pyridin-4-yl; wherein R$^1$ is independently substituted with one or two substituents selected from the group consisting of methoxy and fluoro; provided that phenyl of R$^1$ is substituted with no more than one methoxy substituent.

5. The compound of claim 4, wherein R$^1$ is 2-fluoro-5-methoxyphenyl or 5-fluoro-2-methoxypyridin-4-yl.

6. The compound of claim 1, wherein R$^2$ is C$_{3-5}$cycloalkyl.

7. The compound of claim 6, wherein R$^2$ is cyclopropyl.

8. A compound selected from the group consisting of:
Cpd 1, (3S)-3-cyclopropyl-3-[3-[[6-(2,2-dimethylpropyl)-5-(2-fluoro-5-methoxy-phenyl)pyrazin-2-yl]methoxy]phenyl]propanoic acid;
Cpd 2, (3S)-3-cyclopropyl-3-[3-[[5-(5-fluoro-2-methoxy-4-pyridyl)-6-isobutyl-pyrazin-2-yl]methoxy]phenyl]propanoic acid;
Cpd 3, (3S)-3-[3-[[6-butyl-5-(2-fluoro-5-methoxy-phenyl)pyrazin-2-yl]methoxy]phenyl]-3-cyclopropyl-propanoic acid;
Cpd 4, (3S)-3-cyclopropyl-3-[3-[[6-(2,2-dimethyl-propoxy)-5-(2-fluoro-5-methoxy-phenyl)pyrazin-2-yl]methoxy]phenyl]propanoic acid;
Cpd 5, (3S)-3-cyclopropyl-3-[3-[[5-(2-fluoro-5-methoxy-phenyl)-6-isobutyl-pyrazin-2-yl]methoxy]phenyl]propanoic acid;
Cpd 6, (3S)-3-[3-[(6-[2-azaspiro[3.3]heptan-2-yl]-5-(2-fluoro-5-methoxyphenyl)pyrazin-2-yl)methoxy]phenyl]-3-cyclopropylpropanoic acid;
Cpd 7, (3S)-3-[3-[[6-(cyclohexoxy)-5-(2-fluoro-5-methoxy-phenyl)pyrazin-2-yl]methoxy]phenyl]-3-cyclopropyl-propanoic acid;
Cpd 8, (3S)-3-cyclopropyl-3-[3-[[5-(2-fluoro-5-methoxy-phenyl)-6-(2-methylprop-1-enyl)pyrazin-2-yl]methoxy]phenyl]propanoic acid;
Cpd 9, (3S)-3-[3-[[6-(cyclohexoxy)-5-(5-fluoro-2-methoxy-4-pyridyl)pyrazin-2-yl]methoxy]phenyl]-3-cyclopropyl-propanoic acid;
Cpd 10, (3S)-3-cyclopropyl-3-[3-[[6-(3,5-dimethylphenyl)-5-(2-fluoro-5-methoxy-phenyl)pyrazin-2-yl]methoxy]phenyl]propanoic acid;
Cpd 11, (3S)-3-cyclopropyl-3-[3-[[5-(5-fluoro-2-methoxy-4-pyridyl)-6-(2-methylprop-1-enyl)pyrazin-2-yl]methoxy]phenyl]propanoic acid;
Cpd 12, (3S)-3-cyclopropyl-3-[3-[[5-(5-fluoro-2-methoxy-4-pyridyl)-6-isobutoxy-pyrazin-2-yl]methoxy]phenyl]propanoic acid;
Cpd 13, (3S)-3-[3-[[6-(cyclopentoxy)-5-(2-fluoro-5-methoxy-phenyl)pyrazin-2-yl]methoxy]phenyl]-3-cyclopropyl-propanoic acid;
Cpd 14, (3S)-3-cyclopropyl-3-[3-[[5-(2-fluoro-5-methoxy-phenyl)-6-isobutoxy-pyrazin-2-yl]methoxy]phenyl]propanoic acid;
Cpd 15, (3S)-3-cyclopropyl-3-[3-[[6-(5,5-dimethylcyclopenten-1-yl)-5-(5-fluoro-2-methoxy-4-pyridyl)pyrazin-2-yl]methoxy]phenyl]propanoic acid;
Cpd 16, (3S)-3-[3-[[6-(cyclopentoxy)-5-(5-fluoro-2-methoxy-4-pyridyl)pyrazin-2-yl]methoxy]phenyl]-3-cyclopropyl-propanoic acid;
Cpd 17, (3S)-3-cyclopropyl-3-[3-[[5-(2-fluoro-5-methoxy-phenyl)-6-[(2,2,3,3-tetramethylcyclopropyl)methoxy]pyrazin-2-yl]methoxy]phenyl]propanoic acid;
Cpd 18, (3S)-3-cyclopropyl-3-[3-[[5-(2-fluoro-5-methoxy-phenyl)-6-phenyl-pyrazin-2-yl]methoxy]phenyl]propanoic acid;
Cpd 19, (3S)-3-[3-[[6-(cyclobutoxy)-5-(2-fluoro-5-methoxy-phenyl)pyrazin-2-yl]methoxy]phenyl]-3-cyclopropyl-propanoic acid;
Cpd 20, (3S)-3-cyclopropyl-3-[3-[[5-(2-fluoro-5-methoxy-phenyl)-6-(m-tolyl)pyrazin-2-yl]methoxy]phenyl]propanoic acid;

Cpd 21, (3S)-3-cyclopropyl-3-[3-[[6-(cyclopropylmethoxy)-5-(2-fluoro-5-methoxy-phenyl)pyrazin-2-yl]methoxy]phenyl]propanoic acid;

Cpd 22, (3S)-3-cyclopropyl-3-[3-[[5-(2-fluoro-5-methoxy-phenyl)-6-(1-piperidyl)pyrazin-2-yl]methoxy]phenyl]propanoic acid;

Cpd 23, (3S)-3-cyclopropyl-3-[3-[[5-(2-fluoro-5-methoxy-phenyl)-6-(3-isopropylphenyl)pyrazin-2-yl]methoxy]phenyl]propanoic acid;

Cpd 24, (3S)-3-cyclopropyl-3-[3-[[5-(2-fluoro-5-methoxy-phenyl)-6-(3,3,5,5-tetramethylcyclohexoxy)pyrazin-2-yl]methoxy]phenyl]propanoic acid;

Cpd 25, (3S)-3-cyclopropyl-3-[3-[[5-(2-fluoro-5-methoxy-phenyl)-6-(4-isopropylphenyl)pyrazin-2-yl]methoxy]phenyl]propanoic acid;

Cpd 26, (3S)-3-cyclopropyl-3-[3-[[5-(2-fluoro-5-methoxy-phenyl)-6-(2,2,6,6-tetramethyltetrahydropyran-4-yl)oxy-pyrazin-2-yl]methoxy]phenyl]propanoic acid;

Cpd 27, (3S)-3-[3-[[6-(cycloheptoxy)-5-(2-fluoro-5-methoxy-phenyl)pyrazin-2-yl]methoxy]phenyl]-3-cyclopropyl-propanoic acid;

Cpd 28, (3S)-3-cyclopropyl-3-[3-[[5-(5-fluoro-2-methoxy-4-pyridyl)-6-(5-methyl-2-thienyl)pyrazin-2-yl]methoxy]phenyl]propanoic acid;

Cpd 29, (3S)-3-cyclopropyl-3-[3-[[5-(2-fluoro-5-methoxy-phenyl)-6-isopropoxy-pyrazin-2-yl]methoxy]phenyl]propanoic acid;

Cpd 30, (3S)-3-cyclopropyl-3-[3-[[6-(5,5-dimethylcyclopenten-1-yl)-5-(2-fluoro-5-methoxy-phenyl)pyrazin-2-yl]methoxy]phenyl]propanoic acid;

Cpd 31, (3S)-3-cyclopropyl-3-[3-[[6-(5,5-dimethylcyclopenten-1-yl)-5-(2-methoxy-4-pyridyl)pyrazin-2-yl]methoxy]phenyl]propanoic acid;

Cpd 32, (3S)-3-cyclopropyl-3-[3-[[5-(2-fluoro-5-methoxy-phenyl)-6-(3,3,3-trifluoropropoxy)pyrazin-2-yl]methoxy]phenyl]propanoic acid;

Cpd 33, (3S)-3-cyclopropyl-3-[3-[[5-(2-fluoro-5-methoxy-phenyl)-6-(3-methyl-2-thienyl)pyrazin-2-yl]methoxy]phenyl]propanoic acid;

Cpd 34, (3S)-3-cyclopropyl-3-[3-[[5-(2-fluoro-5-methoxy-phenyl)-6-[isopropyl(methyl)amino]pyrazin-2-yl]methoxy]phenyl]propanoic acid;

Cpd 35, (3S)-3-cyclopropyl-3-[3-[[6-(5,5-dimethylcyclopenten-1-yl)-5-(3-methoxyphenyl)pyrazin-2-yl]methoxy]phenyl]propanoic acid;

Cpd 36, (3S)-3-cyclopropyl-3-[3-[[5-(2-fluoro-5-methoxy-phenyl)-6-(5-methyl-2-thienyl)pyrazin-2-yl]methoxy]phenyl]propanoic acid;

Cpd 37, (3S)-3-cyclopropyl-3-[3-[[5-(2-fluoro-5-methoxy-phenyl)-6-isopropyl-pyrazin-2-yl]methoxy]phenyl]propanoic acid;

Cpd 38, (3S)-3-cyclopropyl-3-[3-[[6-(dimethylamino)-5-(2-fluoro-5-methoxy-phenyl)pyrazin-2-yl]methoxy]phenyl]propanoic acid;

Cpd 39, (3S)-3-cyclopropyl-3-[3-[[6-cyclopropyl-5-(2-fluoro-5-methoxy-phenyl)pyrazin-2-yl]methoxy]phenyl]propanoic acid;

Cpd 40, (3S)-3-cyclopropyl-3-[3-[[5-(2-fluoro-5-methoxy-phenyl)-6-(2,2,2-trifluoro-1-methyl-ethyl)pyrazin-2-yl]methoxy]phenyl]propanoic acid;

Cpd 41, (3S)-3-cyclopropyl-3-[3-[[5-(2-fluoro-5-methoxy-phenyl)-6-(oxetan-3-yloxy)pyrazin-2-yl]methoxy]phenyl]propanoic acid;

Cpd 42, (3S)-3-cyclopropyl-3-[3-[[6-[(3,3-dimethylcyclobutyl)methoxy]-5-(2-fluoro-5-methoxy-phenyl)pyrazin-2-yl]methoxy]phenyl]propanoic acid;

Cpd 43, (3S)-3-[3-[[6-(5-tert-butyl-2-thienyl)-5-(2-fluoro-5-methoxy-phenyl)pyrazin-2-yl]methoxy]phenyl]-3-cyclopropyl-propanoic acid;

Cpd 44, (3S)-3-cyclopropyl-3-[3-[[6-(2,2-dimethylpropylamino)-5-(2-fluoro-5-methoxy-phenyl)pyrazin-2-yl]methoxy]phenyl]propanoic acid;

Cpd 45, (3S)-3-cyclopropyl-3-[3-[[5-(2-fluoro-5-methoxy-phenyl)-6-morpholinopyrazin-2-yl]methoxy]phenyl]propanoic acid;

Cpd 46, (3S)-3-cyclopropyl-3-[3-[[6-(5,5-dimethylcyclopenten-1-yl)-5-(2-fluoro-3-methoxy-phenyl)pyrazin-2-yl]methoxy]phenyl]propanoic acid;

Cpd 47, (3S)-3-cyclopropyl-3-[3-[[6-(2,2-dimethylpropoxy)-5-(5-fluoro-2-methoxy-4-pyridyl)pyrazin-2-yl]methoxy]phenyl]propanoic acid; and Cpd 48, (3S)-3-cyclopropyl-3-[3-[[6-(cyclopropylmethoxy)-5-(5-fluoro-2-methoxy-4-pyridyl)pyrazin-2-yl]methoxy]phenyl]propanoic acid;

or a pharmaceutically acceptable salt thereof.

9. A pharmaceutical composition comprising a compound of claim 1 or 8 and at least one of a pharmaceutically acceptable carrier, a pharmaceutically acceptable excipient, and a pharmaceutically acceptable diluent.

10. The pharmaceutical composition of claim 9, wherein the composition is a solid oral dosage form.

11. The pharmaceutical composition of claim 9, wherein the composition is a syrup, an elixir or a suspension.

12. A method for modulating G protein-coupled receptor 40 activity in a subject, comprising administering to a subject in need thereof a therapeutically effective amount of the compound of claim 1.

13. The method of claim 12, wherein the subject suffers from a disorder selected from the group consisting of type II diabetes mellitus, obesity, an obesity-related disorder, impaired glucose tolerance, insulin resistance, metabolic syndrome, hypertension, osteoporosis, inflammation, eczema and a cardiovascular factor related to unmanaged cholesterol and/or lipid levels.

14. A method for modulating G protein-coupled receptor 40 activity in a subject, comprising administering to a subject in need thereof a therapeutically effective amount of the pharmaceutical composition of claim 9.

15. The method of claim 14, wherein the subject suffers from a disorder selected from the group consisting of type II diabetes mellitus, obesity, an obesity-related disorder, impaired glucose tolerance, insulin resistance, metabolic syndrome, hypertension, osteoporosis, inflammation, eczema and a cardiovascular factor related to unmanaged cholesterol and/or lipid levels.

16. A compound of Formula (I)

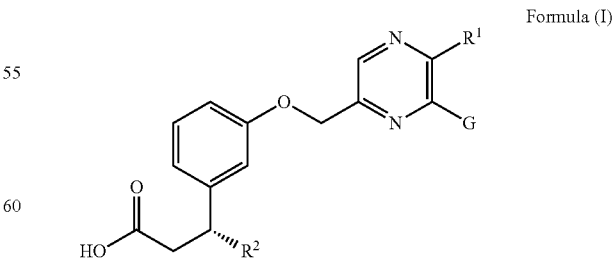

Formula (I)

wherein $R^1$ is selected from the group consisting of phenyl and pyridin-4-yl; wherein $R^1$ is independently substituted with one or two substituents selected from the group consisting of methoxy and fluoro; provided that phenyl of R₁ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-6}$alk-1-en-1-yl; 3,3,3-trifluoropropyloxy; ($C_{1-6}$alkyl)thiophen-2-yl; phenyl optionally substituted with one or two $C_{1-4}$alkyl substituents; N-containing heterocyclyl wherein said N-containing heterocyclyl is attached to the core pyrazine ring via a nitrogen atom and said N-containing heterocyclyl is optionally spiro-fused to a $C_{3-7}$cycloalkyl group; ring g1

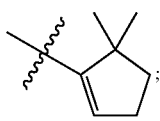

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents; and $R^2$ is $C_{3-5}$cycloalkyl;

or an enantiomer, diastereomer, or pharmaceutically acceptable salt thereof.

17. A compound of Formula (I)

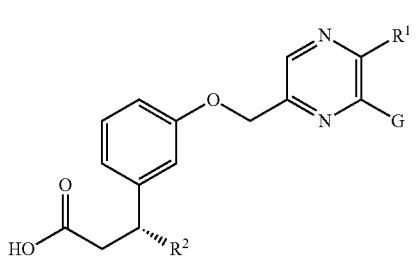

wherein $R^1$ is selected from the group consisting of phenyl and pyridin-4-yl; wherein $R^1$ is independently substituted with one or two substituents selected from the group consisting of methoxy and fluoro; provided that phenyl of $R^1$ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)thiophen-2-yl; phenyl optionally substituted with one or two $C_{1-4}$alkyl substituents; N-containing heterocyclyl wherein said N-containing heterocyclyl is selected from the group consisting of piperidin-1-yl and azetidin-1-yl and said N-containing heterocyclyl is optionally spirofused to a $C_{3-7}$cycloalkyl; ring g1

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents; and $R^2$ is $C_{3-5}$cycloalkyl;

or an enantiomer, diastereomer, or pharmaceutically acceptable salt form thereof.

18. A compound of Formula (I)

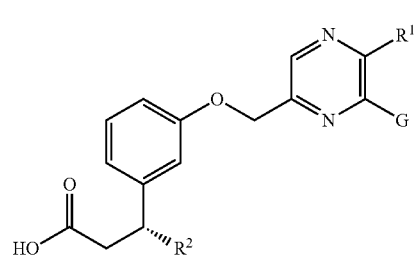

wherein $R^1$ is selected from the group consisting of phenyl and pyridin-4-yl; wherein $R^1$ is independently substituted with one or two substituents selected from the group consisting of methoxy and fluoro; provided that phenyl of $R_1$ is substituted with no more than one methoxy substituent;

G is selected from the group consisting of $C_{1-6}$alkyl; $C_{1-6}$alkoxy; 2,2,6,6-tetramethyltetrahydro-2H-pyran-4-yloxy; $C_{2-4}$alk-1-en-1-yl; 3,3,3-trifluoropropyloxy; (methyl)thiophen-2-yl; phenyl optionally substituted with one or two $C_{1-4}$alkyl substituents; N-containing heterocyclyl wherein said N-containing heterocyclyl is azetidinyl and said azetidinyl is optionally spirofused to a $C_{3-7}$cycloalkyl group to form 2-azaspiro[3.3]heptan-2-yl; ring g1

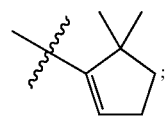

$C_{3-7}$cycloalkyloxy; and $C_{3-7}$cycloalkyl-methoxy;

wherein said $C_{3-7}$cycloalkyloxy and the $C_{3-7}$cycloalkyl portion of $C_{3-7}$cycloalkyl-methoxy are optionally substituted with one to four methyl substituents; and $R^2$ is cyclopropyl;

or an enantiomer, diastereomer, or pharmaceutically acceptable salt thereof.

19. A compound of Formula (I)

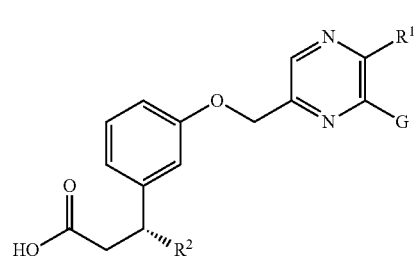

wherein $R^1$ is 2-fluoro-5-methoxyphenyl or 5-fluoro-2-methoxypyridin-4-yl;

G is selected from the group consisting of 2,2-dimethylpropyl, isobutyl, n-butyl, 2,2-dimethylpropyloxy, 2-azaspiro[3.3]heptan-2-yl, cyclohexyloxy, 2-methyl prop-1-enyl, 3,5-dimethylphenyl, isobutyloxy, cyclopentyloxy, 5,5-dimethyl cyclopenten-1-yl, (2,2,3,3-tetramethyl cyclopropyl)methoxy, phenyl, cyclobutyloxy, 3-methylphenyl, cyclopropylmethoxy, 3-isopropylphenyl, 4-isopropylphenyl, (2,2,6,6-tetramethyl tetrahydropyran-4-yl)oxy, cycloheptyloxy, 5-methylthien-2-yl, isopropyloxy, 3,3,3-trifluoropropyloxy, 3-methylthien-2-yl, isopropyl(methyl)amino, isopropyl, dimethylamino, cyclopropyl, 2,2,2-trifluoro-1-methyl-ethyl, oxetan-3-yloxy, (3,3-dimethylcyclobutyl)methoxy, 5-(t-butyl)thien-2-yl, 2,2-dimethylpropylamino, morpholin-4-yl, and cyclopropylmethoxy; and $R^2$ is cyclopropyl;

or an enantiomer, diastereomer, or pharmaceutically acceptable salt thereof.

* * * * *